US010131704B2

(12) United States Patent
Marasco et al.

(10) Patent No.: US 10,131,704 B2
(45) Date of Patent: Nov. 20, 2018

(54) MIDDLE EAST RESPIRATORY SYNDROME CORONAVIRUS NEUTRALIZING ANTIBODIES AND METHODS OF USE THEREOF

(71) Applicant: DANA-FARBER CANCER INSTITUTE, INC., Boston, MA (US)

(72) Inventors: Wayne A. Marasco, Wellesley, MA (US); Xiangchun Tang, West Roxbury, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 15/306,617

(22) PCT Filed: Apr. 27, 2015

(86) PCT No.: PCT/US2015/027785
§ 371 (c)(1),
(2) Date: Oct. 25, 2016

(87) PCT Pub. No.: WO2015/164865
PCT Pub. Date: Oct. 29, 2015

(65) Prior Publication Data

US 2017/0158752 A1 Jun. 8, 2017

Related U.S. Application Data

(60) Provisional application No. 61/984,243, filed on Apr. 25, 2014.

(51) Int. Cl.

| | |
|---|---|
| *C07K 16/10* | (2006.01) |
| *G01N 33/577* | (2006.01) |
| *G01N 33/569* | (2006.01) |
| *A61K 39/00* | (2006.01) |

(52) U.S. Cl.
CPC ....... *C07K 16/10* (2013.01); *G01N 33/56983* (2013.01); *G01N 33/577* (2013.01); *A61K 2039/507* (2013.01); *C07K 2317/13* (2013.01); *C07K 2317/21* (2013.01); *C07K 2317/34* (2013.01); *C07K 2317/52* (2013.01); *C07K 2317/56* (2013.01); *C07K 2317/622* (2013.01); *C07K 2317/76* (2013.01); *C07K 2317/92* (2013.01); *C07K 2319/40* (2013.01); *C07K 2319/43* (2013.01); *C12N 2740/16043* (2013.01); *C12N 2770/20022* (2013.01); *C12N 2810/609* (2013.01); *G01N 2333/165* (2013.01); *G01N 2469/10* (2013.01)

(58) Field of Classification Search
None
See application file for complete search history.

(56) References Cited

U.S. PATENT DOCUMENTS

| | | |
|---|---|---|
| 3,773,919 A | 11/1973 | Bowell et al. |
| 4,485,045 A | 11/1984 | Regen |
| 4,522,811 A | 6/1985 | Eppstein et al. |
| 4,544,545 A | 10/1985 | Ryan et al. |
| 4,676,980 A | 6/1987 | Segal et al. |
| 4,816,567 A | 3/1989 | Cabilly et al. |
| 5,013,556 A | 5/1991 | Woodle et al. |
| 5,030,719 A | 7/1991 | Umemoto et al. |
| 5,233,409 A | 8/1993 | Schwab |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,916,771 A | 6/1999 | Hori et al. |
| 5,939,598 A | 8/1999 | Kucherlapati et al. |

FOREIGN PATENT DOCUMENTS

| | | |
|---|---|---|
| WO | 1994/002602 | 2/1994 |
| WO | 1994/011026 | 5/1994 |
| WO | 1995/022618 | 8/1995 |
| WO | 1996/033735 | 10/1996 |
| WO | 1996/034096 | 10/1996 |
| WO | 1999/053049 | 10/1999 |
| WO | WO 2014/045254 | 3/2014 |
| WO | WO 2015/057942 | 4/2015 |

OTHER PUBLICATIONS

International Search Report and Written Opinion for International Application No. PCT/US2015/027785, dated Sep. 9, 2015, 11 pages.
Zhao, G. et al., "A safe and convenient pseudovirus-based inhibition assay to detect neutralizing antibodies and screen for viral entry inhibitors against the novel human coronavirus MERS-CoV," Virol. J. Jan. 2013; 10:266, 8 pages. Published online Aug. 26, 2013. doi: 10.1186/1743-422X-10-266.
van Boheemen, S. et al., "Genomic characterization of a newly discovered coronavirus associated with acute respiratory distress syndrome in humans," MBio., Nov. 20, 2012;3(6). pii: e00473-12, 9 pages. doi: 10.1128/mBio.00473-12.
Zaki, A. M. et al. (2012) "Isolation of a novel coronavirus from a man with pneumonia in Saudi Arabia," N. Engl. J. Med. 367(19):1814-1820.
Breban, R. et al. (2013) "Interhuman transmissibility of Middle East respiratory syndrome coronavirus: estimation of pandemic risk," Lancet, 382(9893):694-699.
The Health Protection Agency (HPA) UK Novel Coronavirus Investigation team. "Evidence of person-to-person transmission within a family cluster of novel coronavirus infections, United Kingdom, Feb. 2013," Euro Surveill. 2013;18(11):pii=20427. Available online: http://www.eurosurveillance.org/ViewArticle.aspx?ArticleId=20427.

(Continued)

*Primary Examiner* — Benjamin P Blumel
(74) *Attorney, Agent, or Firm* — Baker Donelson

(57) ABSTRACT

The present invention provides antibodies that neutralize MERS-CoV and methods of use thereof. The invented antibody is used to treat MERS-CoV infections and symptoms thereof.

19 Claims, 13 Drawing Sheets

Specification includes a Sequence Listing.

(56) References Cited

OTHER PUBLICATIONS

Cotten, M. et al. (2014) Spread, circulation, and evolution of the middle East respiratory syndrome coronavirus, mBio 5(1):e01062-13. doi:10.1128/mBio.01062-13.
Li, W. et al. (2005) "Receptor and viral determinants of SARS-coronavirus adaptation to human ACE2," The EMBO Journal, 24(8):1634-1643.
The Chinese SARS Molecular Epidemiology Consortium, Reports (2004) "Molecular evolution of the SARS coronavirus during the course of the SARS epidemic in China," Science 303(5664):1666-1669.
Annan, A. et al. (2013) "Human betacoronavirus 2c EMC/2012-related viruses in bats, Ghana and Europe," Emerg Infect Dis 19(3):456-459.
Anthony, S. J. et al. (2013) "Coronaviruses in bats from Mexico," J. Gen Virol., 94(Pt 5):1028-1038.
Woo, P. C. Y. et al. (2006) "Molecular diversity of coronaviruses in bats," Virology 351(1):180-187.
Memish, Z. A. et al. (2013) "Middle East respiratory syndrome coronavirus in bats, Saudi Arabia," Emerg Infect Dis 19(11):1819-1823.
Perera, R. A. et al. (2013) "Seroepidemiology for MERS coronavirus using microneutralisation and pseudoparticle virus neutralisation assays reveal a high prevalence of antibody in dromedary camels in Egypt, Jun. 2013," Euro Surveill, 18(36):pii=20574. Available online: http://www.eurosurveillance.org/ViewArticle.aspx?ArticleId=20574.
Reusken, C. B. E. M. et al. (2013) "Middle East respiratory syndrome coronavirus neutralising serum antibodies in dromedary camels: a comparative serological study," Lancet Infect. Dis. 13(10):859-866. Published online Aug. 9, 2013 http://dx.doi.org/10.1016/S1473-3099(13)70164-6.
Haagmans, B. L. et al. (2014) "Middle East respiratory syndrome coronavirus in dromedary camels: an outbreak investigation," Lancet Infect Dis 14(2):140-145.
Meyer, B. et al. (2014) "Antibodies against MERS coronavirus in dromedaries, United Arab Emirates, 2003 and 2013," Emerg. Infect. Dis. 20(4):552-559. doi: http://dx.doi.org/10.3201/eid2004.131746.
Alagaili, A. N. et al. (2014) "Middle East respiratory syndrome coronavirus infection in dromedary camels in Saudi Arabia," MBio 5(2):e00884-00914. doi:10.1128/mBio.00884-14.
Eckerle, I. et al. (2014) "Replicative capacity of MERS coronavirus in livestock cell lines," Emerg. Infect. Dis. 20(2):276-279.
Muller, M. A. et al. (2012) "Human coronavirus EMC does not require the SARS-coronavirus receptor and maintains broad replicative capability in mammalian cell lines," mBio 3(6):e00515-12. doi:10.1128/mBio.00515-12.
Hofmann, H. et al. (2004) "S protein of severe acute respiratory syndrome-associated coronavirus mediates entry into hepatoma cell lines and is targeted by neutralizing antibodies in infected patients," J. Virol. 78(12):6134-6142.
Chan, K-H et al. (2013) "Cross-reactive antibodies in convalescent SARS patients' sera against the emerging novel human coronavirus EMC (2012) by both immunofluorescent and neutralizing antibody tests," J. Infect 67(2):130-140.
Gierer S. et al. (2013) "The spike protein of the emerging betacoronavirus EMC uses a novel coronavirus receptor for entry, can be activated by TMPRSS2, and is targeted by neutralizing antibodies," J. Virol. 87(10):5502-5511.
Raj, V. S. et al. (2013) "Dipeptidyl peptidase 4 is a functional receptor for the emerging human coronavirus—EMC," Nature 495(7440):251-254.
Lu, G. et al. (2013) "Molecular basis of binding between novel human coronavirus MERS-CoV and its receptor CD26," Nature, 500(7461):227-231.
Wang, N. et al. (2013) "Structure of MERS-CoV spike receptor-binding domain complexed with human receptor DPP4," Cell Research, 23(8):986-993.

Falzarano, D. et al. (2013) "Treatment with interferon-α2b and ribavirin improves outcome in MERS-CoV-infected rhesus macaques," Nature Medicine, 19(10):1313-1317. Published online Sep. 8, 2013; doi:10.1038/nm.3362.
Agnihothram, S. et al. (2014) "Evaluation of serologic and antigenic relationships between Middle Eastern respiratory syndrome coronavirus and other coronaviruses to develop vaccine platforms for the rapid response to emerging coronaviruses," J. Infect Dis., 209:995-1006. Electronically published Nov. 18, 2013.
Du, L. et al. (2013) "A truncated receptor-binding domain of MERS-CoV spike protein potently inhibits MERS-CoV infection and induces strong neutralizing antibody responses: Implication for developing therapeutics and vaccines," PLoS ONE 8(12):e81587. doi:10.1371/journal.pone.0081587.
Song, F. et al. (2013) "Middle East respiratory syndrome coronavirus spike protein delivered by modified vaccinia virus Ankara efficiently induces virus-neutralizing antibodies," J. Virol. 87(21):11950-11954.
Marasco, W. A. et al. (2007) "The growth and potential of human antiviral monoclonal antibody therapeutics," Nat Biotech. 25(12):1421-1434. Published online Dec. 8, 2007; doi:10.1038/nbt1363.
Gould, L. H. et al. (2005) "Protective and therapeutic capacity of human single-chain Fv-Fc fusion proteins against West Nile virus," J. Virol. 79(23):14606-14613.
Kashyap, A. K. et al. (2008) "Combinatorial antibody libraries from survivors of the Turkish H5N1 avian influenza outbreak reveal virus neutralization strategies," PNAS USA, 105(16):5986-5991.
Traggiai, E. et al. (2004) "An efficient method to make human monoclonal antibodies from memory B cells: potent neutralization of SARS coronavirus," Nat Med. 10(8):871-875. Published online Jul. 11, 2004; doi:10/1038/nm1080.
Corti, D. et al. (2011) "A neutralizing antibody selected from plasma cells that binds to group 1 and group 2 influenza A hemagglutinins," Science, 333(6044):850-856.
Throsby, M. et al. (2008) "Heterosubtypic neutralizing monoclonal antibodies cross-protective against H5N1 and H1N1 recovered from human IgM+ memory B cells," PLoS One 3(12):e3942. doi:10.1371/journal.pone.0003942.
Sui, J. et al. (2009) "Structural and functional bases for broad-spectrum neutralization of avian and human influenza A viruses," Nat. Struct. Mol. Biol., 16(3):265-273. Published online Feb. 22, 2009; doi:10.1038/nsmb.1566.
Sui, J. et al. (2004) "Potent neutralization of severe acute respiratory syndrome (SARS) coronavirus by a human mAb to S1 protein that blocks receptor association," PNAS USA, 101(8):2536-2541.
Mou, H. et al. (2013) "The receptor binding domain of the new Middle East respiratory syndrome coronavirus maps to a 231-residue region in the spike protein that efficiently elicits neutralizing antibodies," J. Virol. 87(16):9379-9383.
Sui, J. et al. (2008) "Broadening of neutralization activity to directly block a dominant antibody-driven SARS-coronavirus evolution pathway," PLoS Pathog 4(11):e1000197. doi:10.1371/journal.ppat.1000197.
Wrammert, J. et al. (2008) "Rapid cloning of high-affinity human monoclonal antibodies against influenza virus," Nature, 453(7195):667-671.
Corti, D. et al. (2013) "Broadly neutralizing antiviral antibodies," Annu Rev. Immunol., 31:705-742. doi: 10.1146/annurev-immunol-032712-095916. Epub Jan. 16, 2013.
Wu, X. et al. (2011) "Focused evolution of HIV-1 neutralizing antibodies revealed by structures and deep sequencing," Science, 333(6049):1593-1602. doi:10.1126/science.1207532.
Chan, C. H. et al. (2001) "$V_H1$-69 gene is preferentially used by hepatitis C virus-associated B cell lymphomas and by normal B cells responding to the E2 viral antigen," Blood 97(4):1023-1026.
Huang, C. C. et al. (2004) "Structural basis of tyrosine sulfation and VH-gene usage in antibodies that recognize the HIV type 1 coreceptor-binding site on gp120," PNAS USA, 101(9):2706-2711.
Boyd, S. D. et al. (2010) "Individual variation in the germline Ig gene repertoire inferred from variable region gene rearrangements," J. Immunol. 184(12):6986-6992. Prepublished online May 21, 2010; doi: 10.4049/jimmunol.1000445.

(56) References Cited

OTHER PUBLICATIONS

Watson, C. T. et al. (2012) "The immunoglobulin heavy chain locus: genetic variation, missing data, and implications for human disease," Genes and Immunity, 13(5):363-373.
Farci, P. et al. (2010) "B cell gene signature with massive intrahepatic production of antibodies to hepatitis B core antigen in hepatitis B virus-associated acute liver failure," PNAS USA, 107(19):8766-8771.
Assiri, A. et al. (2013) "Hospital outbreak of Middle East respiratory syndrome coronavirus," N. Eng. J. Med. 369(5):407-416.
Memish, Z. A. et al. (2013) "Family cluster of Middle East respiratory syndrome coronavirus infections," N. Engl. J. Med., 368(26):2487-2494.
Rani, M. et al. (2012) "Increased antibody affinity confers broad in vitro protection against escape mutants of severe acute respiratory syndrome coronavirus," J. Virol., 86(17):9113-9121.
Rockx, B. et al. (2010) "Escape from human monoclonal antibody neutralization affects in vitro and in vivo fitness of severe acute respiratory syndrome coronavirus," J. Infect Dis., 201(6):946-955.
Cotten, M. et al. (2013) "Transmission and evolution of the Middle East respiratory syndrome coronavirus in Saudi Arabia: a descriptive genomic study," Lancet, 382(9909):1993-2002. Published online Sep. 20, 2013, http://dx.doi.org/10.1016/S0140-6736(13)61887-5.
Bermingham, A. et al. (2012) "Severe respiratory illness caused by a novel coronavirus, in a patient transferred to the United Kingdom from the Middle East," Sep. 2012. Euro Surveill. 2012;17(40):pii=20290. Available online: http://www.eurosurveillance.org/ViewArticle.aspx?ArticleId=20290.
Cotten, M. et al. (2013) "Full-genome deep sequencing and phylogenetic analysis of novel human betacoronavirus," Emerg. Infect. Dis., 19(5):736-742B. doi: http://dx.doi.org/10.3201/eid1905.130057.
International Severe Acute Respiratory & Emerging Infection Consortium (ISARIC), "Treatment of MERS-CoV: Decision Support Tool," Clinical Decision Making Tool for Treatment of MERS-CoV v.1.0, Jun. 18, 2013, 22 pages.
ter Meulen, J. et al. (2006) "Human monoclonal antibody combination against SARS coronavirus: synergy and coverage of escape mutants," PLoS Med 3(7):e237. doi: 10.1371/journal.pmed.0030237.
Bakker, A. B. H. et al. (2008) "First administration to humans of a monoclonal antibody cocktail against rabies virus: safety, tolerability, and neutralizing activity," Vaccine, 26(47):5922-5927.
Dimitrov, D. S. (2010) "Therapeutic antibodies, vaccines and antibodyomes," mAbs, 2(3):347-356. doi: 10.4161/mabs.2.3.11779.
Taube, R. et al. (2008) "Lentivirus display: stable expression of human antibodies on the surface of human cells and virus particles," PLoS ONE 3(9):e3181. doi:10.1371/journal.pone.0003181.
Mirzabekov, T. et al. (2000) "Paramagnetic proteoliposomes containing a pure, native, and oriented seven-transmembrane segment protein, CCR5," Nat Biotechnol. 18(6):649-654.
Xu, C. et al. (2007) "Human anti-CXCR4 antibodies undergo $V_H$ replacement, exhibit functional V-region sulfation, and define CXCR4 antigenic heterogeneity," J. Immunol. 179(4):2408-2418. doi: 10.4049/jimmunol.179.4.2408.
Rockx, B. et al. (2008) "Structural basis for potent cross-neutralizing human monoclonal antibody protection against lethal human and zoonotic severe acute respiratory syndrome coronavirus challenge," J. Virol. 82(7):3220-3235. doi:10.1128/JVI.02377-07.
Bona, Constantin A., Sofia Casares, and Teodor-D. Brumeanu. "Towards development of T-cell vaccines." Immunology today 19.3 (1998): 126-133.
Carrell, et al., "A Novel Procedure for the Synthesis of Libraries ontaining Small Organic Molecules" 1994. Angew. Chem. Int. Ed. Engl. 33: 2059.
Carrell, Thomas, et al. "A solution-phase screening procedure for the isolation of active compounds from library of molecules." Angewandte Chemie International Edition in English 33.20 (1984): 2061-2064.
Casadecall, Nat. Biotechnol. 20:114 (2002).
Casares, Sofia, et al. "Protective immunity elicited by vaccination with DNA encoding for a B cell and a T cell epitope of the A/PR/8/34 influenza virus." Viral immunology10.3 (1997): 129-136.
Cole, S. P. C., D. Kozbor, and J. C. Roder, "The EBV-hybridoma technique and its application to human lung cancer," Monoclonal Antibodies and Cancer Therapy 27 (1985): 77-96.Cote, et al., 1983. Proc Natl Acad Sci USA 80: 2026-2030.
Davidson, Beverly L., et al. "A model system for in vivo gene transfer into the central nervous system using an adenoviral vector." Nature genetics 3.3 (1993): 219 Davies et al. (1990) Annual Rev Biochem 59:439-473.
Devlin, James J., Lucy C. Panganiban, and Patricia E. Devlin, "Random peptide libraries: a source of specific protein binding molecules." Science 249.4967 (1990): 404-406.
DeWitt, et al., 1993. Proc. Natl. Acad. Sci. U.S.A. 90: 6909.
Fischer, Rainer, Richard M. Twyman, and Stefan Schillberg. "Production of antibodies in plants and their use for global health." Vaccine 21.7-8 (2003): 820-825.
Fishwild, Dianne M., et al. "High-avidity human IgGκ monoclonal antibodies from a novel strain of minilocus transgenic mice." Nature biotechnology 14.7 (1998): 845.
Gallop, Mark A., et al. "Applications of combinatorial technologies to drug discovery. 1. Background and peptide combinatorial libraries." Journal of medicinal chemistry 37.9 (1994): 1233-1251.
Garrity, Robert R., et al. "Refocusing neutralizing antibody response by targeted dampening of an immunodominant epitope." The journal of immunology 159.1 (1997): 279-289.
Gerloni, Mara, et al. "Immunity to Plasmodium falciparum malaria sporozoites by somatic transgene immunization." Nature biotechnology 15.9 (1997): 876.
Gerloni, Mara, et al. "Somatic transgene immunization with DNA encoding an immunoglobulin heavy chain." DNA and cell biology 16.5 (1997): 611-625.
Goding, James W. Monoclonal antibodies: principles and practice, Elsevier, 1996.
Hoogenboom, Hennie R., and Greg Winter. "By-passing immunisation: human antibodies from synthetic repertoires of germline VH gene segments rearranged in vitro." Journal of molecular biology 227.2 (1992): 381-388.
Houghten, Richard A., et al. "The use of synthetic peptide combinatorial libraries for the identification bioactive peptides," Biotechniques 13.3 (1992): 412-421.
Killen, J. A., and J. M. Lindstrom. "Specific killing of lymphocytes that cause experimental autoimmune myasthenia gravis by ricin toxin-acetylcholine receptor conjugates." The Journal of Immunology 133.5 (1984): 2549-2553.
Köhler, Georges, and Cesar Milstein. "Continuous cultures of fused cells secreting antibody of predefined specificity." Nature256.5517 (1975): 495.
Kozbor, Danuta, and John C. Roder. "The production of monoclonal antibodies from human lymphocytes." Immunology Today 4.3 (1983): 72-79.
Kozbor, Danuta, et al. "A human hybrid myeloma or production of human monoclonal antibodies." The Journal of Immunology 133.6 (1984): 3001-3005.
La Salle, G. Le Gal, et al. "An adenovirus vector for gene transfer into neurons and glia in the brain," Science 259.5097 (1993): 986-990.
Lam, Kit S. "Mini-review. Application of combinatorial library methods in cancer research and drug discovery." Anti-cancer drug design 12.3 (1997): 145-167.
Lonberg, Nils, and Dennis Huszar. "Human antibodies from transgenic mice." International reviews of immunology 13.1 (1995): 65-93.
Malmqvist, Magnus. "Biospecific interaction analysis using biosensor technology." Nature 361.6408 (1993): 186-187.
Marks et al., Bio/Technology 10, 779-783 (1992).
Morrison, Sherie L. "Immunology-Success in Specification." Nature 368.6474 (1994): 812-813.

(56) References Cited

OTHER PUBLICATIONS

Muldoon, Mark T. "ELISA: Theory and practice. Methods in molecular biology, vol. 42: by John R. Crowther. Totowa, Humana, 1995, $59.95 (xi+ 223 pages), ISBN 0-89603-279-5." (1996): 352-353.
Neuberger, Michael. "Generating high-avidity human Mabs in mice." Nature biotechnology 14.7 (1996): 826.
Parren, Paul WHI, and Dennis R. Burton. "The antiviral activity of antibodies in vitro and in vivo." (2001): 195-262.
Shibata, Riri, et al. "Neutralizing antibody directed against the HIV-1 envelope glycoprotein can completely block HIV-1/SIV chimeric virus infections of macaque monkeys." Nature medicine 5.2 (1999): 204.
Shopes, Bob, "A genetically engineered human. IgG mutant with enhanced cytolytic activity." The Journal of Immunology 148.9 (1992): 2918-2922.
Stevenson, G. T., A. Pindar, and C. J. Slade. "A chimeric antibody with dual Fc regions (bisFabFc) prepared by manipulations at the IgG hinge." Anti-cancer drug design 3.4 (1989): 219-230.
Wilkinson, The Scientist Philadelphia Pa., vol. 14, No. 8 (Apr. 17, 2040), pp. 25-28.
Zanetti, Maurizio. "Antigenized antibodies." Nature 355.6359 (1992):476-477.
Antibodies: A Laboratory Manual, Harlow E, and Lane D, 1988, Cold Spring Harbor Laboratory Press, Cold Spring Harbor, N.Y.
"Conjugate Vaccines", Contributions to Microbiology and Immunology, J. M. Cruse and R. E. Lewis, Jr (eds), Carger Press, New York, (1989).
Fodor, Stephen, et al. "Multiplexed biochemical assays with biological chips." Nature 364 (1993): 555-556.
Bobo, R. Hunt, et al. "Convection-enhanced delivery of macromolecules in the brain." Proceedings of the National Academy of Sciences 91.6 (1994): 2076-2080.
Burton, Dennis R. "Antibodies, viruses and vaccines." Nature Reviews Immunology 2.9 (2002): 706.
Caron, Philip C., et al. "Engineered humanized dimeric forms of IgG are more effective antibodies." Journal of Experimental Medicine 176.4 (1992): 1191-1195.
Cull, Millard G., Jeff F. Miller, and Peter J. Schatz. "Screening for receptor ligands using large libraries of peptides linked to the C terminus of the lac repressor." Proceedings of the National Academy of Sciences 89.5 (1992): 1865-1869.
Cwirla, Steven E., et al. "Peptides on phage: a vast library of peptides for identifying ligands." Proceedings of the National Academy of Sciences 87.16 (1990): 6378-6382.
Eppstein, Deborah A., et al. "Biological activity of liposome-encapsulated murine interferon gamma is mediated by a cell membrane receptor." Proceedings of the National Academy of Sciences 82.11 (1985): 3688-3692.
Erb, Eric, Kim D. Janda, and Sydney Brenner. "Recursive deconvolution of combinatorial chemical libraries." Proceedings of the National Academy of Sciences 91.24 (1994): 11422-11426.
Felici, Franco, et al. "Selection of antibody ligands from a large library of oligopeptides expressed on a multivalent exposition vector." Journal of molecular biology 222.2 (1991): 301-310.
Geller, Alfred I., and Andrew Freese. "Infection of cultured central nervous system neurons with a defective herpes simplex virus 1 vector results in stable expression of *Escherichia coli* beta-galactosidase." Proceedings of the National Academy of Sciences 87.3 (1990): 1149-1153.
Geller, Alfred I., et al. "An HSV-1 Vector Expressing Tyrosine Hydroxylase Causes Production and Release of I-DOPA from Cultured Rat Striatal Cells." Journal of neurochemistry 64.2 (1995): 487-496.
Geller, Alfred I., et al. "Long-term increases in neurotransmitter release from neuronal cells expressing a constitutively active adenylate cyclase from a herpes simplex virus type 1 vector" Proceedings of the National Academy of Sciences 90.16 (1993): 7603-7607.

Hwang, Karl J., K. F. Luk, and Paul L. Beaumier. "Hepatic uptake and degradation of unilamellar sphingomyelin/cholesterol liposomes: a kinetic study." Proceedings of the National Academy of Sciences 77.7 (1980): 4030-4034.
Igarashi, Tatsuhiko, et al. "Human immunodeficiency virus type 1 neutralizing antibodies accelerate clearance of cell-free virions from blood plasma." Nature medicine 5.2 (1999): 211.
Kaplitt, Michael G., et al. "Long-term gene expression and phenotypic correction using adeno-associated virus vectors in the mammalian brain." Nature genetics 8.2 (1994): 148.
Keller, Margaret A., and E. Richard Stiehm. "Passive immunity in prevention and treatment of infectious diseases." Clinical microbiology reviews 13.4 (2000): 602-614.
Ko, K., R. Brodzik, and Z. Steplewski. "Production of antibodies in plants: approaches and perspectives." Plant-produced Microbial Vaccines. Springer, Berlin, Heidelberg, 2009. 55-78.
Lam, Kit S., et al. "A new type of synthetic peptide library for identifying ligand-binding activity." Nature 354.6348 (1991): 82.
Lanza, Paola, et al. "Active immunity against the CD4 receptor by using an antibody antigenized with residues 41-55 of the first extracellular domain." Proceedings of the National Academy of Sciences 90.24 (1993): 11683-11687.
Lonberg, Nils, et al. "Antigen-specific human antibodies from mice comprising four distinct genetic modifications." Nature368.6474 (1994): 856.
Lunde, E., et al. "Troybodies and pepbodies." Biochem Soc Trans. Aug. 2002;30(4):500-6.
Marasco, Wayne A., William A. Haseltine, and SiYi Chen. "Design, intracellular expression, and activity of a human anti-human immunodeficiency virus type 1 gp120 single-chain antibody." Proceedings of the National Academy of Sciences90.16 (1993): 7889-7893.
Marks, James D., et al. "By-passing immunization: human antibodies from V-gene libraries displayed on phage." Journal of molecular biology 222.3 (1991): 581-597.
Martin, Francis J., and Demetrios Papahadjopoulos. "Irreversible coupling of immunoglobulin fragments to preformed vesicles. An improved method for liposome targeting." Journal of Biological Chemistry 257.1 (1982): 286-288.
Morrison, Paul F., et al. "High-flow microinfusion: tissue penetration and pharmacodynamics." American Journal of Physiology-Regulatory, Integrative and Comparative Physiology 266.1 (1994): R292-R305.
Munson, Peter J., and David Rodbard. "Ligand: a versatile computerized approach for characterization of ligand-binding systems." Analytical biochemistry 107.1 (1980): 220-239.
Ramakrishnan, S., and L. L. Houston. "Comparison of the selective cytotoxic effects of immunotoxins containing ricin A chain or pokeweed antiviral protein and anti-Thy 1.1 monoclonal antibodies." Cancer research 44.1 (1984): 201-208.
Scott, Jamie K., and George P. Smith. "Searching for peptide ligands with an epitope library." Science 249.4967 (1990): 386-390.
Steward, M. W., C. M. Stanley, and O. E. Obeid. "A mimotope from a solid-phase peptide library induces a measles virus-neutralizing and protective antibody response." Journal of virology 69.12 (1995): 7668-7673.
Vitetta, Ellen S., et al. "Redesigning nature's poisons to create anti-tumor reagents." Science 238.4830 (1987): 1098-1104.
Yang, Yiping, et al. "Cellular and humoral immune responses to viral antigens create barriers to lung-directed gene therapy with recombinant adenoviruses." Journal of virology 69A (1995): 2004-2015.
You, Zhaoyang, et al. "Targeting dendritic cells to enhance DNA vaccine potency." Cancer research 61.9 (2001): 3704-3711.
Zaghouani, Habib, et al. "Induction of antibodies to the human immunodeficiency virus type 1 by immunization of baboons with immunoglobulin molecules carrying the principal neutralizing determinant of the envelope protein." Proceedings of the National Academy of Sciences 92.2 (1995): 631-635.
Zuckermann, Ronald N., et al. "Discovery of nanomolar ligands for 7-transmembrane G-protein-coupled receptors from a diverse N-(substituted) glycine peptoid library." Journal of medicinal chemistry 37.17 (1994): 2678-2685.

| SEQ ID NO: | VH | FR1 | CDR1 | FR2 | CDR2 | FR3 | CDR3 | FR4 | V Gene | D Gene | J Gene | SHM |
|---|---|---|---|---|---|---|---|---|---|---|---|---|
| 68 | Germ. | QVQLVQSGAEVKKPGSSVKVSCKAS | GGTFSSSYA | ISWVRQAPGQGLEWMGG | IIPIFGTA | NYAQKFQGRVTITADKSTSTAYMELSSLRSEDTAVYYC | | WGQGTTVTVSS | 1-69*06 | | 3*02 | |
| 10 | 3A1 | QVQLVQSGAEVKKPGSSVKVSCKAS | GGTFSSSYA | ISWVRQAPGQGLEWVGR | IIPIFGRA | NYAQKFQGRVTITADKSTSTAYMELSSLRREDTAVYYC | ARDQGI-SANF--KDAFDI | WGQGTTVTVSS | 1-69*06 | 3-10*01 | 3*02 | 5 |
| 18 | 3B12 | QVQLVQSGAEVKKPGSSVKVSCKAS | GGTFSSSYA | ISWVRQAPGQGLEWMGG | IIPIFGTA | NYAQKFQGRVTITADKSTSTAYMELSSLRSEDTAVYYC | ARASYC-STTSCASGAFDI | WGQGTLVTVSS | 1-69*06 | 2-2*01 | 3*02 | 0 |
| 14 | 3B11 | QVQLVQSGAEVKKPGSSVKVSCKAS | GGTFSSSYA | ISWVRQAPGQGLEWMGG | IIPIFGTA | NYAQKFQGRVTITADKSTSTAYMELSSLRSEDTAVYYC | ARVGYC-SSTSCHIGAFDI | WGQGTTVTVSS | 1-69*06 | 2-2*01 | 3*02 | 0 |
| 26 | M14D3 | EVQLVQSGAEVKKPGSSVKVSCKAS | GGTFSSSYA | ISWVRQAPGQGLEWMGG | IIPIFGTA | NYAQKFQGRVTITADKSTSTAYMELSSLRSEDTAVYYC | ASSNYYGGSYYPRSAFDI | WGQGTTVTVSS | 1-69*06 | 3-10*01 | 3*02 | 1 |
| 69 | Germ. | QVQLVQSGAEVKKPGSSVKVSCKAS | GGTFSSSYA | ISWVRQAPGQGLEWMGR | IIPILGIA | NYAQKFQGRVTITADKSTSTAYMELSSLRSEDTAVYYC | | | 1-69*09 | | | |
| 22 | 3C12 | EVQLVQSGAEVKKPGSSVKVSCKAS | GYTFTSYA | IWWVRQAPGQGLEWMGR | IIPILGIA | NYAQKFQGRVTITADKSTSTAYMELSSLRSEDTAVYYC | ARDYYGSGA------RGFDY | WGQGTLVTVSS | 1-69*09 | 3-10*02 | 4*02 | 5 |
| 70 | Germ. | QVQLVESGGGVVQPGRSLRLSCAAS | GFTFSSYG | MHWVRQAPGKGLEWVAV | ISYDGSNK | YYADSVKGRFTISRDNSKNTLYLQMNSLRAEDTAVYYC | | | 3-30*03 | | | |
| 2 | 1E9 | QVQLVLSGGGVVQPGRSLRLSCVAS | EFTFRYG | MHWVRQAPGKGLEWVAA | ISYDGYK | YYADSLKGRFTISRDNSKNTLYLQMNSLRSEDTAVYYC | ARSGDS------DAFDI | WGQGTMVTVSS | 3-30*03 | 4-23*01 | 3*02 | 10 |
| 71 | Germ. | QVQLVQSGAEVKKPGASVKVSCKAS | GYTFTSYA | INAGNGNT | KYSQKFQGRVTITRDTSASTAYMELSSLRSEDTAVYYC | | | | 1-3*01 | | | |
| 6 | 1F8 | EVQLVQSGAEVKKPGSSVKVSCKAS | GYTFYSYA | IWWVRQAPGQRLEWMGW | INANGNT | KYSQKFQGRVTITCDTSASTAYMELSSLRSEDTAVYYC | ARDRWMT------RAFDI | WGQGTMVTVSS | 1-3*01 | 4-17*01 | 3*02 | 9 |

| SEQ ID NO: | VL | FR1 | CDR1 | FR2 | CDR2 | FR3 | CDR3 | FR4 | V Gene | J Gene | SHM |
|---|---|---|---|---|---|---|---|---|---|---|---|
| 72 | Germ. | SYELTQPP-SVSVSPGQTASITCSGD | KL------GDKY | ACWYQQKPGQSPVLVIY | QDS | KRPSGIPERFSGSNSGNTATLTISGTQAMDEADYYC | | | LV3-1*01 | LJ3-1*01 | |
| 4 | 1E9 | SYELTQPP-SVSVSPGQTATCSGD | EL------GDKY | AWYQQKPGQSPVLVIY | QDS | KRPSGIPERFSGSNSGNTATLTISGTQADDEADYYC | QAWDSNSVV-- | FGTGTKVTVL | LV3-1*01 | LJ1*01 | 5 |
| 73 | Germ. | QSVLTQPP-SASGTPGQRVTISCSGS | SSNI------GSNY | VYWYQQLPGTAPKLLIY | RNN | QRPSGVPDRFSGSKSGTSASLAISGLRSEDEADYYC | | | LV1-47*01 | | |
| 8 | 1F8 | QPVLTQPP-SASGTPGQRVTISCSGS | SSNI------GSNY | VWWYQQLPGSAPKLLIS | RNN | QRPSGVPDRFSGSKSGTSASLAISGESEDEADYYC | AAWDDSLRGPV | FGGGTRVTVL | LV1-47*01 | LJ3*02 | 5 |
| 74 | Germ. | EIVMTQSPATLSVSPGERATLSCRAS | QSV------SSN | LAWYQQKPGQAPRLLIY | GAS | TRATGIPARFSGSGSGTEFTLTISSLQSEDFAVYYC | | | KV3-15*01 | | |
| 12 | 3A1 | EIVMTQSPATLSVSPGERATLSCRAS | ESV------GSN | LAWYQQKPGQAPRLLIY | GAS | TRATGIPERFSGSGSGTDFTLTISSLQSEDFAVYYC | QQYNWPLT-- | FGPGTKVEIK | KV3-15*01 | KJ3*01 | 6 |
| 75 | Germ. | DIVMTQSPDSLAVSLGERATINCKSS | QSVLYSSNNKNY | LAWYQQKPGQPPKLLIY | WAS | TRESGVPDRFSGSGSGTDFTLTISSLQAEDVAVYYC | | | KV4-1*01 | | |
| 20 | 3B12 | DIGMTQSPDSLAVSLGERATINCKSS | QSVLYSSNNKNY | LAWYQQKPGQPPKLLIY | WAS | ARESGVPDRFSGSGSGTDFTLTISSLQAEDVAIYYC | QQYYSVPFT-- | FGPGTKVEIK | KV4-1*01 | KJ3*01 | 3 |
| 76 | Germ. | EIVLTQSPGTLSLSPGERATLSCRAS | QSV------SSSY | LAWYQQKPGQAPRLLIY | GAS | SRATGIPDRFSGSGSGTDFTLTISRLEPEDFAVYYC | | | KV3-20*01 | | |
| 16 | 3B11 | ETVLTQSPGTLSLSPGERATLSCRAS | QSV------SSS | IAWYQQKPGQAPRLLIP | RSS | TRATGIPDRFSGSGSGTDFTLTISPLEPEDFAVYYC | QQYSSSPYT-- | FGQGTKLEIK | KV3-20*01 | KJ2*01 | 9 |
| 28 | M14D3 | ETVLTQSPATLSVSPGERA:LSCRAS | QSV------S | LAWYQQKPGQAPRLLIY | GAS | SRATGIPDRFSGSGSGTDFTTISRLESEDFAVYYC | QQYGVSPLT-- | FGGGTKVEIK | KV3-20*01 | KJ4*01 | 7 |
| 77 | Germ. | QAGLTQPP-SVSKGLROTATLTCTGN | SNNV------GNQG | AAWLQQHQGHPPKLLSY | RNN | NRPSGISERLSASRSGNTASLTITGLQPEDEADYYC | | | LV10-54*01 | | |
| 24 | 3C12 | QEGLTQPP-SVSKGLROTATLTCTGN | SNNV------GNQG | AAWLQQHQGHPPKLLSY | TNN | NRPSGISERLSASRSGNTASLAITGLQPEDEADYYC | ASWDSSLSVWV | IGGGTKLTVL | LV10-54*01 | LJ3*02 | 2 |

MIDDLE EAST RESPIRATORY SYNDROME CORONAVIRUS NEUTRALIZING ANTIBODIES AND METHODS OF USE THEREOF

RELATED APPLICATIONS

This application claims priority to, and the benefit of U.S. Provisional Application No. 61/984,243 filed Apr. 25, 2014, the contents of which are incorporated herein by reference in their entireties.

GOVERNMENT INTEREST

This invention was made with government support under R01AI085525 awarded by the National Institutes of Health and W011NF-10-0226 awarded by Defense Advanced Research Projects Agency. The United States government has certain rights in the invention.

FIELD OF THE INVENTION

This invention relates generally to Middle East Respiratory Syndrome coronavirus (MERS-CoV) neutralizing antibodies as well as to methods for use thereof.

INCORPORATION-BY-REFERENCE OF SEQUENCE LISTING

The contents of the text file named "DFCI_085001WO_Seq_List.txt" submitted electronically herewith which was created on Jun. 30, 2015 and is 53.5 KB in size, are incorporated herein by reference in their entirety.

BACKGROUND OF THE INVENTION

Middle East Respiratory Syndrome coronavirus (MERS-CoV), a newly emergent subgroup C betacoronavirus, was first isolated from the Arabian Peninsula in 2012. Similar to the Severe Acute Respiratory Syndrome coronavirus (SARS-CoV) that emerged in China in 2002, MERS-CoV causes severe and often lower respiratory tract infection, occasionally accompanied by renal disease. As of Feb. 28, 2014, 184 cases with 80 deaths have been confirmed in 10 countries in the Middle East, Europe, and North Africa. Although the human-to-human transmission rate is mild to moderate at the moment, the increasing number of person-to-person transmissions raises the concern of a more widespread regional outbreak or even global spread by international travelers, similar to what occurred with SARS-CoV in 2002-2003. Limited information exists on the mechanisms that confer increased human-to-human transmission of MERS-CoV. However, mutational adaptation of the SARS-CoV Spike (S) protein for its receptor, angiotensin-converting enzyme 2 (ACE2) was a positive selection factor after zoonotic transfer to humans.

Phylogenetic analysis indicates that MERS-CoV is closely related to CoVs detected in *Tylonycteris pachypus* and *Pipistrellus abramus* bats in China, *Nyctinomops laticaudatus* bats in Mexico, and *Nycteris* cf. *gambiensis* bats in Ghana and Europe. A ~190 base pair nucleotide fragment that was genetically identical to the RNA-dependent RNA polymerase of MERS-CoV was detected in *Taphozous perforatus* bat specimens in the vicinity of the index case in Saudi Arabia. Two independent serological surveys of livestock found that dromedary camels had a high prevalence of neutralizing antibodies (nAbs) against MERS-CoV. Recently, MERS-CoV has been identified from dromedary camels on a farm associated with 2 human cases, but the transmission patterns remain unclear. More recently, a study detected antibodies (Abs) in all 151 dromedary camel serum samples obtained from the United Arab Emirates in 2003, implying that MERS-CoV or closely related CoVs existed in the United Arab Emirates long before the first human MERS cases. A screen of cell lines derived from livestock and peridomestic small mammals on the Arabian Peninsula revealed that only ungulates such as goats and camels showed efficient replication of MERS-CoV. These findings suggest that bats and camels may play an important role in MERS-CoV transmission and that the range of species that can be infected with MERS-CoV may be even broader than currently known.

The coronavirus S protein is a class I membrane fusion protein that represent the major envelope protein on the surface of CoVs. The S protein presents as a trimer and mediates receptor binding, membrane fusion, and virus entry. S is also the major target for nAbs. It has been reported that MERS-CoV infected patients generated S-protein-specific nAbs. The cellular receptor for MERS-CoV has been identified to be dipeptidyl peptidase 4 (DPP4, CD26), which is conserved across many species. The receptor-binding domain (RBD) of the virus S protein in complex with human DPP4 (hDPP4) has been characterized.

Although MERS-CoV has a lower reproduction number ($R_0$) than SARS-CoV (0.69 vs. 0.80), it has a much higher mortality rate than SARS-CoV (43% vs. 10%). Currently, there are no licensed vaccines or antivirals available for the prevention or treatment of MERS. Combination treatment with interferon-alpha2β and ribavirin can moderate the host response and has been reported to improve clinical outcomes in MERS-CoV-infected rhesus macaques. MERS-CoV S protein vaccines based on modified vaccinia virus Ankara or Venezuelan Equine Encephalitis Replicon Particles and purified RBD can induce virus nAbs in mouse models. However, results of human studies have not been reported. Thus, there remains an urgent medical need for the targeted prophylaxis and treatment of MERS.

Accordingly, there is an urgent need for therapeutics and prophylactic methods for preventing Middle East Respiratory Syndrome coronavirus infection, and diseases and disorders related thereto

SUMMARY OF THE INVENTION

The invention is based upon the discovery of monoclonal antibodies which neutralize the Middle East Respiratory Syndrome coronavirus (MERS-CoV) wherein said monoclonal antibody binds to an epitope in the receptor binding domain (RBD) of the spike protein of a, and neutralizes MERS-CoV.

In various aspects, the monoclonal antibody is a bivalent antibody, a monovalent antibody, a single chain antibody or fragment thereof. Specifically, such monoclonal bind to an epitope on to an epitope in the receptor binding domain (RBD) of the spike protein of MERS-CoV. The epitope is non-linear.

In some embodiments the epitope comprises the amino acid position amino acids 349-590 of the spike protein. More specifically, the epitope comprises at least one amino acid at position 506, 512, 540, 542 or 547 of the spike protein when numbered in accordance with SEQ ID NO: 58

Exemplary monoclonal antibodies include monoclonal antibody 1E9, 1F8, 3B12, 3A1, 3C12, 3B11 or M14D3 or an antibody that binds to the same epitope as 1E9, 1F8, 3B12, 3A1, 3C12, 3B11 or M14D3.

The monoclonal antibodies of the invention can have the binding affinity of monoclonal antibody 1E9, 1F8, 3B12, 3A1, 3C12, 3B11 or M14D3. The monoclonal antibodies of the invention function to inhibit viral and cell membrane fusion. More specifically, the antibody bocks the binding of MERS-CoV spike protein to DPP4 receptor.

The monoclonal antibody has a heavy chain variable amino acid sequence containing SEQ ID NOS: 2, 6, 10, 14, 18, 22, or 26 and/or a light chain variable amino acid sequence containing SEQ ID NOS: 4, 8, 12, 16, 20, 24 or 28.

The monoclonal antibody, has a heavy chain variable nucleic acid sequence containing SEQ ID NOS: 1, 5, 9, 13, 17, 21, 25, or 27 and or a light chain variable nucleic acid sequence containing SEQ ID NOS: 3, 7, 9, 11, 15, 19, 23, or 27.

Also provided by the invention is an monoclonal anti-influenza hemagglutinin protein antibody or fragment thereof, where the antibody has a heavy chain with three CDRs comprising the amino acid sequences EFTFNTYG (SEQ ID NO:29), ISYDGTKK (SEQ ID NO:30), and ARSGDSDAFDI (SEQ ID NO:31) respectively and/or a light chain with three CDRs comprising the amino acid sequences ELGDKF (SEQ ID NO:46), QDS (SEQ ID NO:47), and QAWDSNSYV (SEQ ID NO:48) respectively; a heavy chain with three CDRs comprising the amino acid sequences GGTFGSYA (SEQ ID NO:32), IDAANGNT (SEQ ID NO:33), and ARDRWMTTRAFDI (SEQ ID NO:34) respectively and/or a light chain with three CDRs comprising the amino acid sequences SSNIGSNY (SEQ ID NO:49), RNN (SEQ ID NO:50), and AAWDDSLRGPV (SEQ ID NO:51) respectively; a heavy chain with three CDRs comprising the amino acid sequences GGTFSSYA (SEQ ID NO:35), IIPIFGKA (SEQ ID NO:36), and ARDQGISANFKDAFDI (SEQ ID NO:37) respectively and/or a light chain with three CDRs comprising the amino acid sequences ESVGSN (SEQ ID NO:52), GAS (SEQ ID NO:53), and QQYNNWPLT (SEQ ID NO:54) respectively; a heavy chain with three CDRs comprising the amino acid sequences GGTFSSYA (SEQ ID NO:35), IIPIFGTA (SEQ ID NO:59), and ARVGYCSSTSCHIGAFDI (SEQ ID NO:39) respectively and/or a light chain with three CDRs comprising the amino acid sequences QSVSSS (SEQ ID NO:55), DSS (SEQ ID NO:56), and QQYSSSPYT (SEQ ID NO:57) respectively; a heavy chain with three CDRs comprising the amino acid sequences GGTFSSYA (SEQ ID NO:35), IIPIFGTA (SEQ ID NO:59), and ARASYCSTTSCASGAFDI (SEQ ID NO:40) respectively and/or a light chain with three CDRs comprising the amino acid sequences QSVLYSSNNKNY (SEQ 1D NO:61), WAS (SEQ ID NO:62), and QQYYSVPFT (SEQ ID NO:63) respectively; a heavy chain with three CDRs comprising the amino acid sequences GYTFNVYA (SEQ ID NO:41), IIPILGIA (SEQ ID NO:42), and ARDYYGSGARGFDY (SEQ ID NO:43) respectively and/ or a light chain with three CDRs comprising the amino acid sequences SNNVGNQG (SEQ ID NO:60), TNN (SEQ ID NO:66), and ASWDSSLSVWV (SEQ ID NO:67) respectively; or a heavy chain with three CDRs comprising the amino acid sequences GGTFSSYA (SEQ ID NO:38), IIPIFGIA (SEQ ID NO:44), and ASSNYYGSGSYYPRSAFDI (SEQ ID NO:45) respectively and/or a light chain with three CDRs comprising the amino acid sequences QSISND (SEQ ID NO:64), GAS (SEQ ID NO:53), and QQYGVSPLT (SEQ ID NO:65) respectively.

In another aspect, the invention provides a method of preventing or treating a disease or disorder caused by an Middle East Respiratory Syndrome coronavirus (MERS-CoV) by administering to a person at risk of suffering from said disease or disorder, a therapeutically effective amount of a monoclonal antibody or scFV antibody described herein. The monoclonal antibody or scFV antibody is administered at a dose sufficient to neutralize the MERS-CoV. In embodiments of the invention, the method also includes administering an anti-viral drug, a viral entry inhibitor or a viral attachment inhibitor. The antibody is administered prior to or after exposure to MERS-CoV.

In another aspect, the invention provides a method of detecting the presence of a an MERS-CoV in a sample by contacting the sample with a monoclonal antibody as described herein, and detecting the presence or absence of an antibody-antigen complex, thereby detecting the presence of a MERS-CoV in a sample. The test sample is generally obtained from blood, hair, cheek scraping or swab, saliva, biopsy, urine, feces, sputum, nasal aspiration, or semen.

The invention further provides a method of delaying the onset of one ore more symptoms of MERS-CoV by administering to a person at risk of suffering from said disease or disorder, a therapeutically effective amount of a monoclonal antibody or scFV antibody described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from and are encompassed by the following detailed description and claims.

BRIEF DESCRIPTION OF THE DRAWINGS

FIG. 1. Amino acid sequences of variable regions of anti-MERS-CoV Spike mAbs. Framework regions 1-4 (FR1-4) and complementarity-determining regions 1-3 (CDR1-3) for VH and VL are shown. FR, CDR and germline are defined according to the IMGT database. Hyphens denote gaps. Somatic hypermutations (SHMs) are highlighted in red. Because the first 6 amino acids of rearranged VH and VL segments may be biased due to PCR priming, they were thus not included in SHM analysis and are colored in blue. Germ.: Germline gene.

Figure 13:
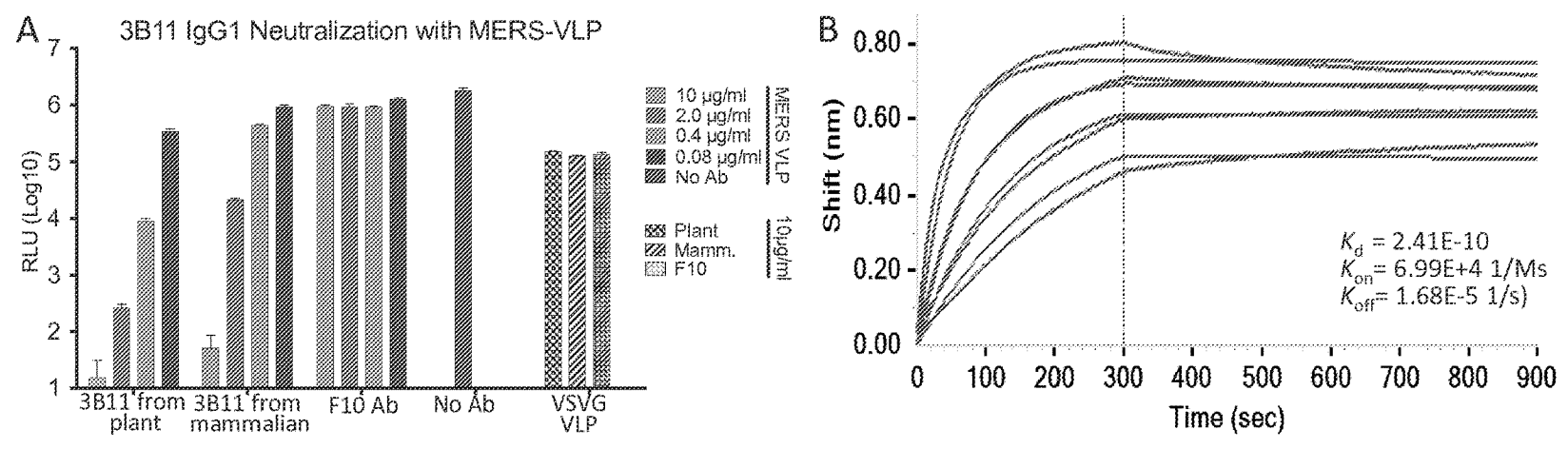

FIG. 13 Neutralization (A) and Kinetics (B) of plant produced 3B11 IgG1 mAb. (A) Serially diluted IgG1s produced from plant or mammalian cells were tested with MERS-VLPs. Anti-influenza HA mAb (F10) was used as a negative Ab control, and VSV-G pseudotyped virus was used as pseudovirus control for neutralization specificity. (B). Kinetic characterization of 3B11 IgG1 mAb produced from plant.

DETAILED DESCRIPTION

Figure 2:
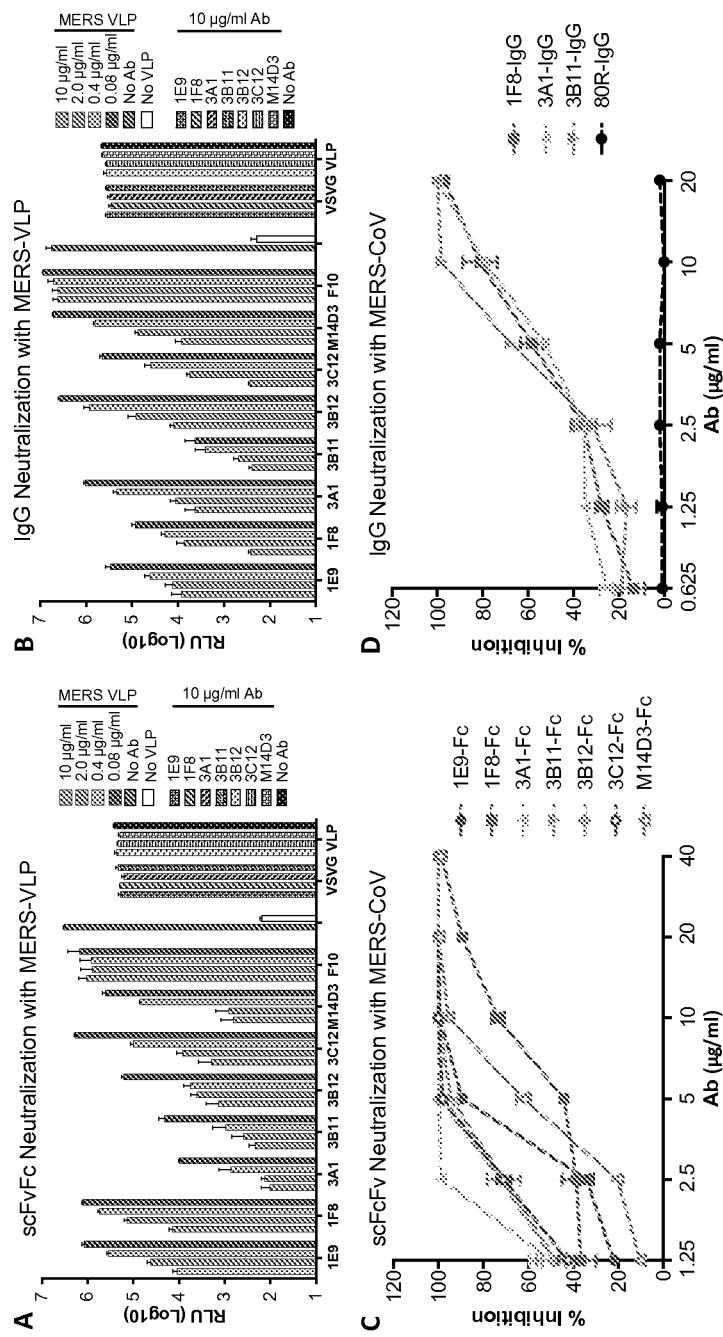
FIG. 2. Neutralization with MERS S pseudotyped lentivirus (A, B) or live virus (C, D). Serially diluted scFvFc (A) and IgG1 (B) were tested with MERS-CoV S pseudotyped lentivirus. For pseudovirus neutralization assay, anti-influenza HA mAb (F10) was used as a negative Ab control and VSV-G pseudotyped virus was used as pseudovirus control for neutralization specificity. Seven scFvFcs (C) and three IgG1s (D) were tested by $PRNT_{50}$ assay with live MERS-CoV. The anti-SARS S mAb 80R was used as a negative Ab control.

The present invention provides antibodies that neutralize infection by Middle East Respiratory Syndrome coronavirus (MERS-CoV).

Specifically, seven anti-MERS-CoV spike nAbs were isolated from a non-immune human Ab-phage library using a novel panning strategy. These nAbs bind to three different epitopes in the RBD-hDPP4 interface with sub-nM to nM affinity and neutralize MERS-CoV infection. At least one major mechanism of action is their capacity to inhibit S protein binding to its DPP4 receptor. The residues within the RBD critical for neutralization were identified through the generation of escape variants and were confirmed by kinetic binding studies. Despite the close proximity of the three epitopes on the RBD interface, escape from one epitope minimally altered other Ab neutralization directed to a different epitope. Importantly, the majority of escape mutations had negative impacts on hDPP4 receptor binding and viral fitness. These results provide insight into the basis and biases of human nAbs against MERS-CoV that may contribute to MERS-CoV clearance and evolution.

Abs typically accumulate 5~20% amino acid changes in their V-segments during the affinity maturation process, which consist of 6~25 amino acid changes in the VH or VL domains (39). NAbs against HIV gp120 often have 19~46% of the amino acid changes in their VH genes alone (40). The seven anti-spike nAbs described here use 3 VH and 6 VL germline genes with 0~10 SHMs. Interestingly, five of seven Abs use the IGHV1-69 germline gene that is preferentially used by many anti-viral nAbs, including those directed against hepatitis C virus (HCV) and influenza viruses (34, 39, 41). IGHV1-69 is the only VH gene that has two hydrophobic residues at the tip of its CDR-H2 loop that can make direct contact with the viral glycoprotein (42). The Abs 3B11 and 3B12 use the VH1-69*06 germline gene without any SHMs and have only 9 or 3 SHMs in their light chains respectively, yet maintain sub-nM binding affinities for S. The hydrophobic core of Patch 2 at the RBD-hDPP4 interface is in the center of these epitopes. We suggest that the IGHV1-69 Abs may replace hDPP4 and make direct contact with this hydrophobic core through their CDR-H2 loops (23). Our finding that zero to only a few SHMs are required for RBD binding further suggests that a potential greater number of IGHV1-69 B cell receptor (BCR) precursors may be able to recognize the RBD and that a prolonged affinity maturation process is not required to develop a potent nAb response. In addition, there are 13 IGHV1-69 alleles and significant copy number variation (CNV) from 0 to 5 copies for any individual due to gene deletions and duplication (43, 44). The IGHV3-30 and IGHV1-3 germline genes respectively used by 1E9 and 1F8 also have multiple alleles and have been reported for other anti-viral Abs (39, 45).

Figure 4:
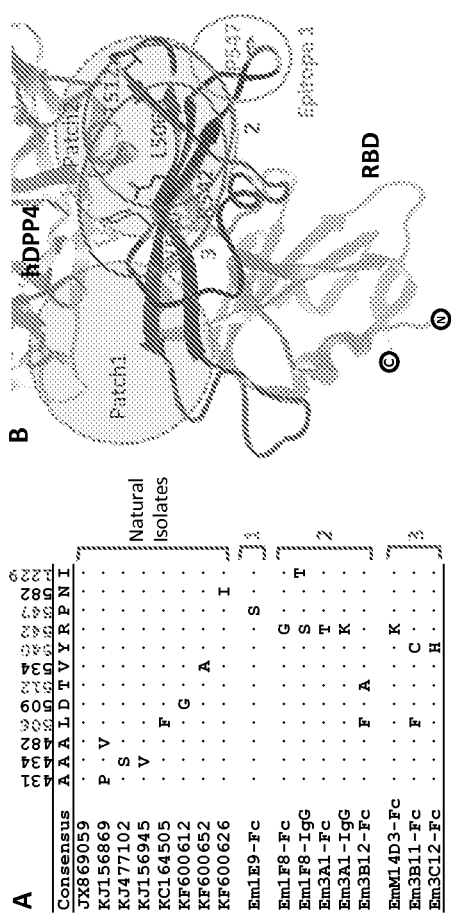
FIG. 4. Escape mutations. (A) Amino acid differences among the RBDs of the S proteins of natural isolates and escape mutants (Em). (B) Diagram of the escape mutations in the RBD. The structure was adapted from PDB ID 4KR0. The receptor-binding motif (RBM) (aa484-567) is colored in purple, and the receptor-binding core is colored in light blue. The hDPP4 is colored grey. Three proposed epitopes are depicted as solid circles: cyan, epitope 1; magenta, epitope 2; and green, epitope 3. Escape mutation residues are colored based on their corresponding epitope locations. Two major binding patches are shown in light green and orange shaded/dotted circles.

Human DPP4 binds to the MERS-CoV RBD with a equilibrium dissociation constant ($K_d$) of approximately 21.4 nM, which is comparable with a previous report 16.7 nM (22). All seven nAbs bind to the RBD with 10- to 450-fold higher affinity than hDPP4. Previous studies have indicated that higher Ab affinity confers broader and higher neutralizing activity (48). Here, we dissect the contributions of binding affinity and epitope specificity toward defining nAb activities. When binding to the same epitope, nAbs with higher binding affinity had higher neutralizing activity. For epitope group 2 Abs, 3A1 scFvFc had a higher affinity than 1F8 and exhibited better neutralization activity (FIG. 2A, Table 2). The same held true for epitope group 3 Abs, 3B11 scFvFc/IgG, which also had a higher affinity and showed better neutralizing activity than 3C12 scFvFc/IgG (FIGS. 2A&B, Table 2). However, when nAbs bind to different epitopes, those nAbs binding to the center of the RBD-hDPP4 interface are more potent. For example, epitope 1 Ab 1E9 has strong binding affinity to the RBD, but it has weak neutralization activity (FIG. 2A, Table 2), perhaps because 1E9 binds to the small η4 helix that is close to but distinct from the RBD-hDPP4 interface. Binding to this position may not completely block hDPP4 binding to the RBD. In contrast, 3C12 has lower binding affinity than 1E9, but it has better neutralization activity than 1E9, as it binds directly at the RBD-hDPP4 interface (FIG. 4B).

The generation of neutralization escape mutants can be a helpful tool for identifying residues critical for neutralization and for investigating virus evolution under immune pressure (37, 49). Like other RNA viruses, CoVs have high mutation rates, especially during cross-species transmission, which is important for virus adaptation to new host receptors (5, 6, 50). Immune pressure is another force selecting virus mutation (37, 49). With the exception of the 3B11 IgG, which appears to have a binding affinity below the neutralization escape threshold (Table 2), all other Abs, including 3B11 scFvFc, underwent neutralization escape. Based on Ab studies against a number of viral pathogens by ourselves and other investigators, we assume that the escape mutants from these nAbs may reflect virus evolution under similar nAb-mediated immune pressure in patients. In vitro escape studies showed that a single amino acid mutation at residues Y540 and R542 could confer virus neutralization escape from four nAbs (1F8, 3A1, 3C12, and M14D3). For the 3B11 and 3B12 Abs, which use the germline gene of IGHV1-69*06, two escape mutations were observed for each nAb, although further investigation indicated that the L506F substitution alone could not abrogate 3B11 and 3B12 nAb binding; in contrast, the respective Y540C and T512A substitutions resulted in the profound loss of nAb binding activity. Natural virus variation with F506 has been reported for England-1 MERS-CoV, which was isolated from the second MERS patient from Qatar (51). It is possible that 3B11- or 3B12-like nAbs were involved in driving the L506F mutation (52). We tested the neutralization of 3B11 and 3B12 scFvFcs on England-1 CoV strain which encodes the L506 F substitution in the S protein. The respective $IC_{50}$ values for 3B11-Fc and 3B12-Fc were 5.48 and 13.8 µg/ml, which demonstrated that 3- or 11-fold higher concentrations were required to neutralize the England-1 MERS-CoV strain compared to the EMC/2012 MERS-CoV strain.

Figure 5:
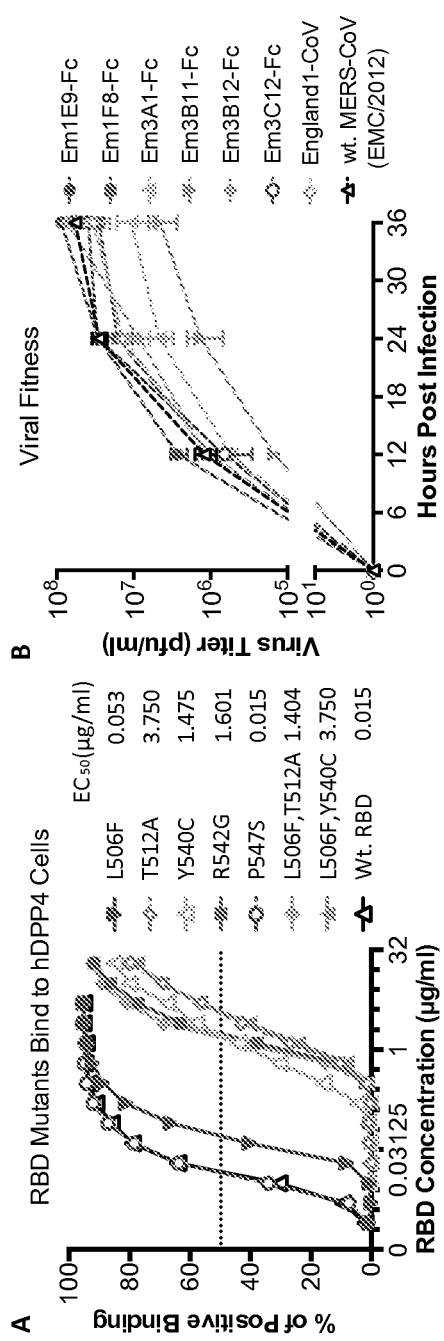
FIG. 5. Characterization of RBD mutants. (A) Analysis of half maximal effective concentrations ($EC_{50}$) for the RBD mutant proteins binding to 293T-hDPP4 cells. Each purified RBD mutant, constructed with an hFc tag, was 2× serially diluted (starting from 5 or 20 μg/ml, 12 dilutions) and then incubated with $1 \times 10^5$ 293 T-hDPP4. The binding of the RBD mutant proteins was monitored with APC-Cy7 labeled anti-hFc Abs by FACS. (B) In vitro growth kinetics of nAb escape mutant MERS-CoVs. Vero cells were infected with 0.1 MOI of escape mutant or wild type MERS-CoV for 1 h in triplicates. Upon removing unbound viruses and replenishing with growth media, culture supernatants were sampled in triplicates at indicated time points and virus titers were determined by plaque assay on Vero cells.

The effects of these escape mutations on hDPP4 binding activity and viral fitness are also significant. Both BLI and FACS assessments of RBD mutants indicated that, with the exception of the P547S substitution that was selected by the epitope 1 Ab 1E9, all other substitutions exhibited either small (L506F) or significantly (T512A, Y540C, R542G) decreases in RBD binding affinity to hDPP4 (Table 4). Viral fitness assays demonstrated that the P547S substitution slightly enhanced viral fitness while the substitutions at positions T512, Y540, and R542 of epitopes 2 and 3 decreased viral fitness. Although we did not generate a viral escape mutant carrying the L506F substitution alone, the decrease in binding affinity for hDPP4 caused by the L506F substitution may contribute to its decreased viral fitness (25)(FIG. 5A, Table 4). These results lead us to propose that the immunodominance of the human nAb response to the RBD-hDPP4 interface can restrict MERS-CoV evolution by driving virus down an escape pathway that predominantly results in a significant cost on viral fitness. In vitro human mAb neutralization studies on SARS-CoV recapitulated the escape mutations that were seen during the SARS outbreak (37). Additionally, decreased virulence of the neutralization escape mutants coincided with reduced affinity of the mutant SARS-S for its ACE2 receptor (49). Given the decreased growth kinetics of these escaped mutants in vitro, we anticipate that the majority of escape mutants selected from similar nAbs in vivo may be attenuated.

In summary, this invention provides potent anti-MERS-CoV S nAbs that bind to three epitopes at the RBD interface and show minimal evidence of cross-epitope resistance. We suggest that MERS-CoV vaccines, particularly those that express S in the context of virus/VLP membranes, as we describe here, may be an effective way to present this vulnerable interface for immune recognition (26, 27). In addition, in view of current recommendations by the International Severe Acute Respiratory and Emerging Infection Consortium (ISARIC) and the increasing recognition that human Abs may have a role in the management of infectious diseases, the therapeutic potential of these nAbs should be considered for the prophylaxis and treatment of MERS (53). While escape from neutralization is a concern with therapeutic Abs, our study provides reagents and a strategy to mitigate this potential problem. Divergent combination immunotherapy (DCI) uses two different nAbs to non-cross-resistant epitopes to decrease the possibility of viral escape while taking advantage of synergistic neutralizing effects (37, 49, 54, 55). By virtue of its high affinity and lack of neutralization escape, the 3B11 IgG should be included in this mAb cocktail. In addition, our immunogenetic results provide the basis for comparisons with more global anti-bodyome studies of circulating B cells from MERS-CoV-infected patients during acute and/or convalescent phases of infection and an opportunity to examine the role that Ig polymorphism may play in shaping the protective Ab repertoire and influencing clinical responses (44, 56).

In another embodiment, the antibodies that neutralize infection by Middle East Respiratory Syndrome coronavirus (MERS-CoV) can be belong to various kinds of antibody classes and isotypes. For example, the neutralizing antibodies can be IgG$_1$, IgG$_2$, IgG$_3$ and/or IgG$_4$ isotype antibodies.

In another embodiment, the neutralizing antibodies can also contain LALA mutations in the Fc region. The LALA double mutants are characterized by the L234A L235A amino acid substitutions.

The humanized antibodies described herein may be produced in mammalian expression systems, such as hybridomas. The humanized antibodies described herein may also be produced by non-mammalian expression systems, for example, by transgenic plants. For example, the antibodies described herein are produced in transformed tobacco plants (*N. benthamiana* and *N. tabaccum*).

The nucleic acid and amino acid sequence of the neutralizing MERS-CoV antibodies are provided below:

TABLE 1A

Antibody 1E9 Variable Region nucleic acid sequences

V$_H$ chain of 1E9
(SEQ ID NO: 1)
CAGGTGCAGCTGGTGCAGTCTGGGGGAGGCGTGGTCCAACCTGGGAGGTC

CCTGAGACTCTCCTGTGTAGCCTCTGAGTTCACCTTCAATACTTATGGCA

TGCACTGGGTCCGCCAGGCTCCAGGCAAGGGACTGGAGTGGGTGGCAGCT

ATTTCATATGATGGAACTAAGAAATTTTATGCAGACTCCCTGAAGGGCCG

ATTCACCATCTCCAGAGACAATTCCAAGAACACGTTGTATCTCCAAATGA

ACAGCCTGAGATCTGAGGACACGGCCGTGTATTACTGTGCGAGAAGTGGT

GACTCCGATGCTTTTGATATCTGGGGCCAAGGGACAATGGTCACCGTCTC

CTCA

V$_L$ chain of 1E9
(SEQ ID NO: 3)
TCCTATGAGCTGACTCAGCCACCCTCAGTGTCCGTGTCCCCAGGACAGAC

AGCCACCATCACCTGCTCTGGAGATGAATTGGGGGATAAATTTGCTTTCT

GGTATCAACAAAAGCCAGGCCAGTCCCCTGTGCTGGTCATCTATCAAGAT

AGTAAGAGGCCCTCAGGGATCCCTGAGCGATTCTCTGGCTCCAACTCTGG

GAACACAGCCACTCTGACCATCAGCGGGACCCAGGCTCTGGATGAGGCTG

ACTATTACTGTCAGGCGTGGGACAGCAACAGTTATGTCTTCGGAACTGGG

ACCAAGGTCACCGTCCTAGGT

TABLE 1B

Antibody 1E9 Variable Region amino acid sequences

V$_H$ chain of 1E9
(SEQ ID NO: 2)
QVQLVQSGGGVVQPGRSLRLSCVASEFTFNTYGMHWVRQAPGKGLEWVAA

ISYDGTKKFYADSLKGRFTISRDNSKNTLYLQMNSLRSEDTAVYYCARSG

DSDAFDIWGQGTMVTVSS

TABLE 1B-continued

Antibody 1E9 Variable Region amino acid sequences

V$_L$ chain of 1E9
(SEQ ID NO: 4)
SYELTQPPSVSVSPGQTATITCSGDELGDKFAFWYQQKPGQSPVLVIYQD

SKRPSGIPERFSGSNSGNTATLTISGTQALDEADYYCQAWDSNSYVFGTG

TKVTVL

TABLE 1C

Antibody 1F8 Variable Region nucleic acid sequences

V$_H$ chain of 1F8
(SEQ ID NO: 5)
GAGGTGCAGCTGGTGCAGTCTGGGGCTGAGGTGAAGGAGCCTGGGTCCTC

GGTGAAGGTCTCCTGCAAGGCTTCTGGGGGCACCTTCGGCAGTTATGCTA

TCAACTGGGTGCGACAGGCCCCTGGACAAAGGCTTGAGTGGATGGGATGG

ATCGACGCTGCCAATGGTAACACAAAATATTCACAGAAGTTCCAGGGCAG

AGTCACCATTACCGGAGACACATCCGCGAGCACAGCCTACATGGAACTGA

GCAGCCTGAGATCTGAAGACACGGCTGTGTATTACTGTGCGAGAGATAGG

TGGATGACTACGCGGGCTTTTGATATCTGGGGCCAAGGGACAATGGTCAC

CGTCTCTTCA

V$_L$ chain of 1F8
(SEQ ID NO: 7)
CAGCCTGTGCTGACTCAGCCACCCTCAGCGTCTGGGACCCCCGGGCAGAG

GGTCACCATCTCTTGTTCTGGAAGCAGCTCCAACATCGGAAGTAATTATG

TTTTCTGGTACCAGCAGCTCCCAGGGATGGCCCCCAAACTCCTCATCTCT

AGGAATAATCAGCGGCCCTCAGGGGTCCCTGACCGATTCTCTGGCTCCAA

GTCTGGCACCTCAGCCTCCCTGGCCATCAGTGGGCCCCAGTCTGAGGATG

AGGCTGATTATTACTGTGCAGCATGGGATGACAGCCTGCGTGGTCCCGTG

TTCGGCGGAGGGACCAGGGTGACCGTCCTAGGT

TABLE 1D

Antibody 1F8 Variable Region amino acid sequences

V$_H$ chain of 1F8
(SEQ ID NO: 6)
EVQLVQSGAEVKEPGSSVKVSCKASGGTFGSYAINWVRQAPGQRLEWMGW

IDAANGNTKYSQKFQGRVTITGDTSASTAYMELSSLRSEDTAVYYCARDR

WMTTRAFDIWGQGTMVTVSS

V$_L$ chain of 1F8
(SEQ ID NO: 8)
QPVLTQPPSASGTPGQRVTISCSGSSSNIGSNYVFWYQQLPGMAPKLLIS

RNNQRPSGVPDRFSGSKSGTSASLAISGPQSEDEADYYCAAKDDSLRGPV

FGGGTRVTVL

TABLE 1E

Antibody 3A1 Variable Region nucleic acid sequences

V<sub>H</sub> chain of 3A1
(SEQ ID NO: 9)
CAGGTGCAGCTGGTGCAGTCTGGGGCTGAGGTGAAGAAGCCTGGGTCCTC
GGTGAAGGTCTCCTGCAAGGCGTCTGGAGGCACTTTCAGCAGCTATGCAG
TCAGCTGGGTGCGACAGGCCCCTGGACAAGGTCTTGAGTGGGTGGGAAGG
ATAATCCCTATTTTTGGTAAGGCAAACTACGCACAGAAGTTCCAGGGCAG
AGTCACGATAACCGCGGACAAATCCACGAGCACAGCCTATATGGAACTGA
GCAGCCTGAGACCTGAAGACACGGCCGTATATTACTGTGCGAGAGATCAG
GGGATTTCGGCCAATTTCAAAGATGCTTTTGATATCTGGGGCCAAGGGAC
CACGGTCACCGTCTCCTCA V<sub>L</sub> chain of 3A1
(SEQ ID NO: 11)
GAAACGACACTCACGCAGTCTCCAGCCACCCTGTCTGTGTCTCCAGGGGA
AAGAGCCACCCTCTCCTGCAGGGCCAGTGAGAGTGTTGGCAGCAACTTAG
CCTGGTACCAGCAGAAACCTGGCCAGGCTCCCAGCCTCCTCATCTATGGT
GCATCCACCAGGGCCACTGGTATCCCAGACAGATTCAGTGGCAGTGGGTC
TGGGACAGACTTCACTCTCACCATCAGCAGCCTGCAGTCTGAAGATTTTG
CAGCTTATTATTGTCAGCAGTATAATAACTGGCCACTCACCTTCGGCCCT
GGGACCAAAGTGGAAATCAAA

TABLE 1F

Antibody 3A1 Variable Region amino acid sequences

V<sub>H</sub> chain of 3A1
(SEQ ID NO: 10)
QVQLVQSGAEVKKPGSSVKVSCKASGGTFSSYAVSWVRQAPGQGLEWVGR
IIPIFGKANYAQKFQGRVTITADKSTSTAYMELSSLRPEDTAVYYCARDQ
GISANFKDAFDIWGQGTTVTVSS V<sub>L</sub> chain of 3A1
(SEQ ID NO: 12)
ETTLTQSPATLSVSPGERATLSCRASESVGSNLAWYQQKPGQAPSLLIYG
ASTRATGIPDRFSGSGSGTDFTLTISSLQSEDFAAYYCQQYNNWPLTFGP
GTKVEIK

TABLE 1G

Antibody 3B11 Variable Region nucleic acid sequences

V<sub>H</sub> chain of 3B11
(SEQ ID NO: 13)
CAGGTGCAGCTGGTGCAGTCTGGGGCTGAGGTGAAGAAGCCTGGGTCCTC
GGTGAAGGTCTCCTGCAAGGCTTCTGGAGGCACCTTCAGCAGCTATGCTA
TCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAG
AGTCACGATTACCGCGGACAAATCCACGAGCACAGCCTACATGGAGCTGA
GCAGCCTGAGATCTGAGGACACGGCCGTGTATTACTGTGCGAGGGTAGGA
TATTGTAGTAGTACCAGCTGTCACATCGGCGCTTTTGATATCTGGGGCCA
AGGGACCACGGTCACCGTCTCCTCA V<sub>L</sub> chain of 3B11
(SEQ ID NO: 15)
GAAACGACACTCACGCAGTCTCCAGGCACCCTGTCTTTGTCTCCAGGGGA
AAGAGCCACCCTCTCCTGCAGGGCCAGTCAGAGTGTTAGCAGCAGCATAG
CCTGGTATCAGCAGAAACCTGGGCAGGCTCCCAGGCTCCTCATGTTTGAT
TCATCCACCAGGGCCACTGGTATCCCAGACAGGTTCAGTGGCAGTGGGTC
TGGGACAGACTTCACTCTCAACATCAGCAGCCTAGAGCCTGAAGATTTTG
CAGTGTATTACTGTCAGCAGTATAGTAGCTCACCTTACACTTTTGGCCAG
GGGACCAAACTGGAGATCAAA

TABLE 1H

Antibody 3B11 Variable Region chain amino acid sequences

V<sub>H</sub> chain of 3B11
(SEQ ID NO: 14)
QVQLVQSGAEVKKPGSSVKVSCKASGGTFSSYAISWVRQAPGQGLEWMGG
IIPIFGTANYAQKFQGRVTITADKSTSTAYMELSSLRSEDTAVYYCARVG
YCSSTSCHIGAFDIWGQGTTVTVSS V<sub>L</sub> chain of 3B11
(SEQ ID NO: 16)
ETTLTQSPGTLSLSPGERATLSCRASQSVSSSIAWYQQKPGQAPRLLMFD
SSTRATGIPDRFSGSGSGTDFTLNISSLEPEDFAVYYCQQYSSSPYTFGQ
GTKLEIK

TABLE 1I

Antibody 3B12 Variable Region nucleic acid sequences

V<sub>H</sub> chain of 3B12
(SEQ ID NO: 17)
CAGGTGCAGCTGGTGCAGTCTGGGGCTGAGGTGAAGAAGCCTGGGTCCTC
GGTGAAGGTCTCCTGCAAGGCTTCTGGAGGCACCTTCAGCAGCTATGCTA
TCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAG
AGTCACGATTACCGCGGACAAATCCACGAGCACAGCCTACATGGAGCTGA
GCAGCCTGAGATCTGAGGACACGGCCGTGTATTACTGTGCGAGAGCCTCA
TATTGTAGTACTACCAGCTGCGCTAGTGGTGCTTTTGATATCTGGGGCCA
AGGCACCCTGGTCACCGTCTCCTCA V<sub>L</sub> chain of 3B12
(SEQ ID NO: 19)
GACATCCAGATGACCCAGTCTCCAGACTCCCTGGCTGTGTCTCTGGGCGA
GAGGGCCACCATCAACTGCAAGTCCAGCCAGAGTGTTTTATACAGCTCCA

TABLE 1I-continued

Antibody 3B12 Variable Region nucleic acid sequences

ACAATAAGAACTACTTAGCTTGGTACCAGCAGAAACCAGGACAGCCTCCT

AAGCTGCTCATTTACTGGGCATCTGCCCGGGAATCCGGGGTCCCTGACCG

ATTCAGTGGCAGCGGGTCTGGGACAGATTTCACTCTCACCATCAGCAGCC

TGCAGCCTGAAGATGTGGCAATTTATTACTGTCAGCAATATTATAGTGTT

CCATTCACTTTCGGCCCTGGGACCAAAGTGGAGATCAAA

TABLE 1J

Antibody 3B12 Variable Region amino acid sequences $V_H$ chain of 3B12
(SEQ ID NO: 18)
QVQLVQSGAEVKKPGSSVKVSCKASGGTFSSYAISWVRQAPGQGLEWMGG

IIPIFGTANYAQKFQGRVTITADKSTSTAYMELSSLASEDTAVYYCARAS

YCSTTSCASGAFDIWGQGTLVTVSS $V_L$ chain of 3B12
(SEQ ID NO: 20)
DIQMTQSPDSLAVSLGERATINCKSSQSVLYSSNNKNYLAWYQQKPGQPP

KLLIYWASARESGVPDRFSGSGSGTDFTLTISSLQPEDVAIYYCQQYYSV

PFTFGPGTKVEIK

TABLE 1K

Antibody 3C12 Variable Region nucleic acid sequences $V_H$ chain of 3C12
(SEQ ID NO: 21)
GAGGTGCAGCTGGTGCAGTCTGGAGCTGAGGTGAAGAAGCCTGGGGCCTC

AGTGAAGGTTTCCTGCAAGGCTTCTGGATACACCTTCAATGTATATGCTA

TCAACTGGGTGCGACAGGCCCCTGGACAAGGGCTTGAGTGGATGGGAAGG

ATCATCCCTATCCTTGGTATAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTGTATTACTGTGCGAGAGATTAC

TATGGTTCGGGAGCTAGGGGCTTTGACTACTGGGGCCAGGGCACCCTGGT

CACCGTCTCCTCA $V_L$ chain of 3C12
(SEQ ID NO: 23)
CAGCCTGGGCTGACTCAGCCACCCTCGGTGTCCAAGGGCTTGAGACAGAC

CGCCACACTCACCTGCACTGGGAACAGCAACAATGTTGGCAACCAAGGAG

CAGCTTGGCTGCAGCAGCACCAGGGCCACCCTCCCAAACTCCTATCCTAC

ACGAATAACAACCGGCCCTCAGGGATCTCAGAGAGATTATCTGCATCCAG

GTCAGGAAACACAGCCTCCCTGGCCATTACTGGACTCCAGCCTGAGGACG

AGGCAGACTATTACTGTGCATCATGGGACAGCAGCCTCAGTGTTTGGGTG

ATCGGCGGAGGGACCAAGTTGACCGTCCTAGGT

TABLE 1L

Antibody 3C12 Variable Region amino acid sequences $V_H$ chain of 3C12
(SEQ ID NO: 22)
EVQLVQSGAEVKKPGASVKVSCKASGYTFNVYAINWVRQAPGQGLEWMGR

IIPILGIANYAQKFQGRVTITADKSTSTAYMELSSLRSEDTAVYYCARDY

YGSGARGFDYWGQGTLVTVSS $V_L$ chain of 3C12
(SEQ ID NO: 24)
QPGLTQPPSVSKGLRQTATLTCTGNSNNVGNQGAAWLQQHQGHPPKLLSY

TNNNRPSGISERLSASRSGNTASLAITGLQPEDEADYYCASWDSSLSVWV

IGGGTKLTVL

TABLE 1M

Antibody M14D3 Variable Region nucleic acid sequences $V_H$ chain of M14D3
(SEQ ID NO: 25)
GAGGTGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAGGG

ATCATCCCTATCTTTGGTATAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTGTATTACTGTGCGAGCTCTAAT

TACTATGGTTCAGGGAGTTATTATCCGCGAAGTGCTTTTGATATCTGGGG

CCAAGGGACCACGGTCACCGTCTCCTCA $V_L$ chain of M14D3
(SEQ ID NO: 27)
GAAACGACACTCACGCAGTCTCCAGCCACCCTGTCTGTGTCTCCAGGGGA

AAGGGCCATCCTCTCCTGCAGGGCCAGTCAGAGTATAAGCAATGACTTAG

CCTGGTACCAGCAGAAACCTGGCCAGGCTCCCAGGCTCCTCATCTATGGT

GCATCCAGCAGGGCCACTGGCATCCCAGACAGGTTCAGTGGCAGTGGGTC

TGGGACGGACTTCACCTTCACCATCAGCAGACTGGAGTCTGAAGATTTTG

CAGTGTATTACTGTCAGCAGTATGGTGTTTCACCTCTCACTTTCGGCGGG

GGGACCAAGGTGGAGATCAAA

TABLE 1N

Antibody M14D3 Variable Region amino acid sequences $V_H$ chain of M14D3
(SEQ ID NO: 26)
EVQLVQSGAEVKKPGSSVKVSCKASGGTFSSYAISWVRQAPGQGLEWMGG

IIPIFGIANYAQKFQGRVTITADKSTSTAYMELSSLRSEDTAVYYCASSN

YYGSGSYYPRSAFDIWGQGTTVTVSS

TABLE 1N-continued

Antibody M14D3 Variable Region amino acid sequences

V$_L$ chain of M14D3
(SEQ ID NO: 28)
ETTLTQSPATLSVSPGERAILSCRASQSISNDLAWYQQKPGQAPRLLIYG

ASSRATGIPDRFSGSGSGTDFTFTISRLESEDFAVYYCQQYGVSPLTFGG

GTKVEIK

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, and chimeric antibodies In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, IgG$_3$, IgG$_4$. Furthermore, in humans, the light chain may be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "epitope" includes any protein determinant capable of specific binding to an immunoglobulin, a scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant (K$_d$) of the interaction, wherein a smaller K$_d$ represents a greater affinity Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" (K$_{on}$) and the "off rate constant" (K$_{off}$) can be determined by calculation of the concentrations and the actual rates of association and dissociation. (See Nature 361:186-87 (1993)). The ratio of K$_{off}$/K$_{on}$ enables the cancellation of all parameters not related to affinity, and is equal to the dissociation constant K$_d$. (See, generally, Davies et al. (1990) Annual Rev Biochem 59:439-473). An antibody of the present invention is said to specifically bind to a MERS-CoV epitope when the equilibrium binding constant (K$_d$) is ≤1 µM, preferably ≤100 nM, more preferably ≤10 nM, and most preferably ≤100 pM to about 1 pM, as measured by assays such as radioligand binding assays or similar assays known to those skilled in the art.

An MERS-CoV protein or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to MERS-CoV. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the MERS-CoV with which it is normally reactive, and then add the human monoclonal antibody being tested to determine if the human monoclonal antibody being tested is inhibited in its ability to bind MERS-CoV e. If the human monoclonal antibody being tested is inhibited then, in all likelihood, it has the same, or functionally equivalent, epitopic specificity as the monoclonal antibody of the invention.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103) Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, humanized antibodies can be produced in transgenic plants, as an an inexpensive production alternative to existing mammalian systems. For example, the transgenic plant may be a tobacco plant, i.e., *Nicotiania benthamiana*, and *Nicotiana tabaccum*. The antibodies are purified from the plant leaves. Stable transformation of the plants can be achieved through the use of *Agrobacterium tumefaciens* or particle bombardment. For example, nucleic acid expression vectors containing at least the heavy and light chain sequences are expressed in bacterial cultures, i.e., *A. tumefaciens* strain BLA4404, via transformation. Infiltration of the plants can be accomplished via injection. Soluble leaf extracts can be prepared by grinding leaf tissue in a mortar and by centrifugation. Isolation and purification of the antibodies can be readily be performed by many of the methods known to the skilled artisan in the art. Other methods for antibody production in plants are described in, for example, Fischer et al., Vaccine, 2003, 21:820-5; and Ko et al, Current Topics in Microbiology and Immunology, Vol. 332, 2009, pp. 55-78. As such, the present invention further provides any cell or plant comprising a vector that encodes the antibody of the present invention, or produces the antibody of the present invention.

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of MERS-CoV in a sample. The antibody can also be used to try to bind to and disrupt MERS-CoV.

In a preferred embodiment, the antibodies of the present invention are full-length antibodies, containing an Fc region similar to wild-type Fc regions that bind to Fc receptors.

Heteroconjugate antibodies are also within the scope of the present invention. Heteroconjugate antibodies are composed of two covalently joined antibodies. It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in neutralizing or preventing viral infection. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)). In a preferred embodiment, the antibody of the present invention has modifications of the Fc region, such that the Fc region does not bind to the Fc receptors. Preferably, the Fc receptor is Fcγ receptor. Particularly preferred are antibodies with modification of the Fc region such that the Fc region does not bind to Fcγ, but still binds to neonatal Fc receptor.

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun 133:1335-2549 (1984); Jansen et al, Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against MERS-CoV

Methods for the screening of antibodies that possess the desired specificity include, but are not limited to, enzyme linked immunosorbent assay (ELISA) and other immunologically mediated techniques known within the art.

Antibodies directed against a MERS-CoV as the spike protein may be used in methods known within the art relating to the localization and/or quantitation of MERS-CoV (e.g., for use in measuring levels of the MERS-CoV protein within appropriate physiological samples, for use in diagnostic methods, for use in imaging the protein, and the like). In a given embodiment, antibodies specific to an MERS-CoV, or derivative, fragment, analog or homolog thereof, that contain the antibody derived antigen binding domain, are utilized as pharmacologically active compounds (referred to hereinafter as "Therapeutics").

An antibody specific for a MERS-CoV can be used to isolate a MERS-CoV polypeptide by standard techniques, such as immunoaffinity, chromatography or immunoprecipitation. Antibodies directed against an MERS-CoV protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention, including polyclonal, monoclonal, humanized and fully human antibodies, may used as therapeutic agents. Such agents will generally be employed to treat or prevent a MERS-CoV-related disease or pathology in a subject. An antibody preparation, preferably one having high specificity and high affinity for its target antigen, is administered to the subject and will generally have an effect due to its binding with the target. Administration of the antibody may abrogate or inhibit or interfere with the internalization of the virus into a cell. In this case, the antibody binds to the target and prevents MERS-CoV binding the DPP4 receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding a MERS-CoV protein or a fragment thereof of the invention, as well as other molecules identified by the screening assays disclosed herein, can be administered for the treatment of a MERS-CoV-related disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

In the embodiments of the present invention, antibody fragments are not preferred, specifically antibody fragments lacking an Fc region. Peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of a MERS-CoV (or a protein or a protein fragment thereof) in a sample. Preferably, the antibody contains a detectable label. Antibodies can be polyclonal, or more preferably, monoclonal. An intact antibody is preferred. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the fusion of a MERS-CoV to the cell membrane. Also provided are methods of identifying compounds useful to treat MERS-CoV infection. The invention also encompasses compounds identified using the screening assays described herein.

For example, the invention provides assays for screening candidate or test compounds which modulate the interaction between the MERS-CoV and the cell membrane. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409.).

In one embodiment, a candidate compound is introduced to an antibody-antigen complex and determining whether the candidate compound disrupts the antibody-antigen complex, wherein a disruption of this complex indicates that the candidate compound modulates the interaction between a MERS-CoV and the cell membrane.

In another embodiment, at least one MERS-CoV protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat a MERS-CoV-related disease or disorder. For example, the at least one MERS-CoV protein may be provided as a MERS-CoV molecule.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a MERS-CoV neutralizing antibody, such as monoclonal antibody 1E9, 1F10, 3B12, 3A1, 3C12, 3B11 or M14D3 or any variant thereof wherein the Fc region is modified such that it has reduced binding or does not bind to the Fc-gamma receptor. Additionally, the antigen may be a MERS-CoV protein, or a portion thereof.

The screening methods disclosed herein may be performed as a cell-based assay or as a cell-free assay. The cell-free assays of the invention are amenable to use of both the soluble form or the membrane-bound form of the proteins and fragments thereof. In the case of cell-free assays comprising the membrane-bound forms of the proteins, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether), N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody or the antigen (e.g. the can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, an assay can be performed in which a MERS-CoV or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with a second, labeled antibody or antibody bound to a coupling agent such as biotin or avidin. This second antibody may be another anti-MERS-CoV antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid and the label bound to the solid phase is measured. These and other immunoassays can be easily performed by those of ordinary skill in the art.

An exemplary method for detecting the presence or absence of a MERS-CoV (in a biological sample involves obtaining a biological sample from a test subject and contacting the biological sample with a labeled monoclonal antibody according to the invention such that the presence of the MERS-CoV is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect an MERS-CoV in a biological sample in vitro as well as in vivo. For example, in vitro techniques for detection of a MERS-CoV include enzyme linked immunosorbent assays (ELISAs), Western blots, immunoprecipitations, and immunofluorescence. Furthermore, in vivo techniques for detection of a MERS-CoV include introducing into a subject a labeled anti-MERS-CoV antibody. For example, the antibody can be labeled with a radioactive marker whose presence and location in a subject can be detected by standard imaging techniques.

In one embodiment, the biological sample contains protein molecules from the test subject. One preferred biological sample is a peripheral blood leukocyte sample isolated by conventional means from a subject.

The invention also encompasses kits for detecting the presence of a MERS-CoV in a biological sample. For example, the kit can comprise: a labeled compound or agent capable of detecting a MERS-CoV (e.g., an anti-MERS-CoV monoclonal antibody) in a biological sample; means for determining the amount of a MERS-CoV in the sample; and means for comparing the amount of a MERS-CoV in the sample with a standard. The compound or agent can be packaged in a suitable container. The kit can further comprise instructions for using the kit to detect a MERS-CoV in a sample.

Passive Immunization

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using neutralizing human monoclonal antibodies could provide an immediate treatment strategy for emergency prophylaxis and treatment of MERS-CoV infection and related diseases and disorders while the alternative and more time-consuming development of vaccines and new drugs in underway.

Subunit vaccines potentially offer significant advantages over conventional immunogens. They avoid the safety hazards inherent in production, distribution, and delivery of conventional killed or attenuated whole-pathogen vaccines. Furthermore, they can be rationally designed to include only confirmed protective epitopes, thereby avoiding suppressive T epitopes (see Steward et al., J. Virol. 69:7668 (1995)) or immunodominant B epitopes that subvert the immune system by inducing futile, non-protective responses (e.g. "decoy" epitopes). (See Garrity et al., J. Immunol. 159:279 (1997)).

Moreover, those skilled in the art will recognize that good correlation exists between the antibody neutralizing activity in vitro and the protection in vivo for many different viruses, challenge routes, and animal models. (See Burton, Natl. Rev. Immunol. 2:706-13 (2002); Parren et al., Adv. Immunol. 77:195-262 (2001)). The data presented herein demonstrate that the mAb-11 human monoclonal antibody and other mAb variants can be further developed and tested in in vivo animal studies to determine its clinical utility as a potent ADE inhibitor for prophylaxis and treatment of MERS-CoV infection and related diseases and disorders.

Antigen-Ig Chimeras in Vaccination

It has been over a decade since the first antibodies were used as scaffolds for the efficient presentation of antigenic determinants to the immune systems. (See Zanetti, Nature 355:476-77 (1992); Zaghouani et al., Proc. Natl. Acad. Sci. USA 92:631-35 (1995)). When a peptide is included as an integral part of an IgG molecule (e.g., the 11A or 256 IgG1 monoclonal antibody described herein), the antigenicity and immunogenicity of the peptide epitopes are greatly enhanced as compared to the free peptide. Such enhancement is possibly due to the antigen-IgG chimeras longer half-life, better presentation and constrained conformation, which mimic their native structures.

Moreover, an added advantage of using an antigen-Ig chimera is that either the variable or the Fc region of the antigen-Ig chimera can be used for targeting professional antigen-presenting cells (APCs). To date, recombinant Igs have been generated in which the complementarity-determining regions (CDRs) of the heavy chain variable gene ($V_H$) are replaced with various antigenic peptides recognized by B or T cells. Such antigen-Ig chimeras have been used to induce both humoral and cellular immune responses. (See Bona et al., Immunol. Today 19:126-33 (1998)).

Chimeras with specific epitopes engrafted into the CDR3 loop have been used to induce humoral responses to either HIV-1 gp120 V3-loop or the first extracellular domain (D1) of human CD4 receptor. (See Lanza et al., Proc. Natl. Acad. Sci. USA 90:11683-87 (1993); Zaghouani et al., Proc. Natl. Acad. Sci. USA 92:631-35 (1995)). The immune sera were able to prevent infection of CD4 SupT1 cells by HIV-1MN (anti-gp120 V3C) or inhibit syncytia formation (anti-CD4-D1). The CDR2 and CDR3 can be replaced with peptide epitopes simultaneously, and the length of peptide inserted can be up to 19 amino acids long.

Alternatively, one group has developed a "troybody" strategy in which peptide antigens are presented in the loops of the Ig constant (C) region and the variable region of the chimera can be used to target IgD on the surface of B-cells or MHC class II molecules on professional APCs including B-cells, dendritic cells (DC) and macrophages. (See Lunde et al., Biochem. Soc. Trans. 30:500-6 (2002)).

An antigen-Ig chimera can also be made by directly fusing the antigen with the Fc portion of an IgG molecule. You et al., Cancer Res. 61:3704-11 (2001) were able to obtain all arms of specific immune response, including very high levels of antibodies to hepatitis B virus core antigen using this method.

DNA Vaccination

DNA vaccines are stable, can provide the antigen an opportunity to be naturally processed, and can induce a longer-lasting response. Although a very attractive immunization strategy, DNA vaccines often have very limited potency to induce immune responses. Poor uptake of injected DNA by professional APCs, such as dendritic cells (DCs), may be the main cause of such limitation. Combined with the antigen-Ig chimera vaccines, a promising new DNA vaccine strategy based on the enhancement of APC antigen presentation has been reported (see Casares, et al., Viral Immunol. 10:129-36 (1997); Gerloni et al., Nat. Biotech. 15:876-81 (1997); Gerloni et al., DNA Cell Biol. 16:611-25 (1997); You et al., Cancer Res. 61:3704-11 (2001)), which takes advantage of the presence of Fc receptors (FcγRs) on the surface of DCs.

It is possible to generate a DNA vaccine encoding an antigen (Ag)-Ig chimera. Upon immunization, Ag-Ig fusion proteins will be expressed and secreted by the cells taking up the DNA molecules. The secreted Ag-Ig fusion proteins, while inducing B-cell responses, can be captured and internalized by interaction of the Fc fragment with FcγRs on DC surface, which will promote efficient antigen presentation and greatly enhance antigen-specific immune responses. Applying the same principle, DNA encoding antigen-Ig chimeras carrying a functional anti-MHC II specific scFv region gene can also target the immunogens to all three types of APCs. The immune responses could be further boosted with use of the same protein antigens generated in vitro (i.e., "prime and boost"), if necessary. Using this strategy, specific cellular and humoral immune responses against infection of MERS-CoV were accomplished through intramuscular (i.m.) injection of a DNA vaccine. (See Casares et al., Viral. Immunol. 10:129-36 (1997)).

Vaccine Compositions

Therapeutic or prophylactic compositions are provided herein, which generally comprise mixtures of one or more monoclonal antibodies or ScFvs and combinations thereof. The prophylactic vaccines can be used to prevent a MERS-CoV infection and the therapeutic vaccines can be used to treat individuals following a MERS-CoV infection. Prophylactic uses include the provision of increased antibody titer to a MERS-CoV in a vaccination subject. In this manner, subjects at high risk of contracting MERS-CoV (i.e., in subtropical regions where viral-carrying mosquitoes thrive) can be provided with passive immunity to a MERS-CoV.

These vaccine compositions can be administered in conjunction with ancillary immunoregulatory agents. For example, cytokines, lymphokines, and chemokines, including, but not limited to, IL-2, modified IL-2 (Cys125→Ser125), GM-CSF, IL-12, γ-interferon, IP-10, MIP1β, and RANTES.

Methods of Immunization

The vaccines of the present invention have superior immunoprotective and immunotherapeutic properties over other anti-viral vaccines.

The invention provides a method of immunization, e.g., inducing an immune response, of a subject. A subject is immunized by administration to the subject a composition containing a membrane fusion protein of a pathogenic spike protein. The fusion protein is coated or embedded in a biologically compatible matrix.

The fusion protein is glycosylated, e.g. contains a carbohydrate moiety. The carbohydrate moiety may be in the form of a monosaccharide, disaccharide(s). oligosaccharide(s), polysaccharide(s), or their derivatives (e.g. sulfo- or phospho-substituted). The carbohydrate is linear or branched. The carbohydrate moiety is N-linked or O-linked to a polypeptide. N-linked glycosylation is to the amide nitrogen of asparagine side chains and O-linked glycosylation is to the hydroxy oxygen of serine and threonine side chains.

The carbohydrate moiety is endogenous to the subject being vaccinated. Alternatively, the carbohydrate moiety is exogenous to the subject being vaccinated. The carbohydrate moiety is a carbohydrate moieties that are not typically expressed on polypeptides of the subject being vaccinated. For example, the carbohydrate moieties are plant-specific carbohydrates. Plant specific carbohydrate moieties include for example N-linked glycan having a core bound α1,3 fucose or a core bound β 1,2 xylose. Alternatively, the carbohydrate moiety are carbohydrate moieties that are expressed on polypeptides or lipids of the subject being vaccinate. For example many host cells have been genetically engineered to produce human proteins with human-like sugar attachments.

The subject is at risk of developing or suffering from a viral infection. For example, the subject has traveled to regions or countries in which other MERS-CoV infections have been reported.

The methods described herein lead to a reduction in the severity or the alleviation of one or more symptoms of a viral infection. Infections are diagnosed and or monitored, typically by a physician using standard methodologies. A subject requiring immunization is identified by methods know in the art. For example subjects are immunized as outlined in the CDC's General Recommendation on Immunization (51(RR02) pp 1-36).

The subject is e.g., any mammal, e.g., a human, a primate, mouse, rat, dog, cat, camel, cow, horse, pig, a fish or a bird.

The treatment is administered prior to diagnosis of the infection. Alternatively, treatment is administered after diagnosis. Efficaciousness of treatment is determined in association with any known method for diagnosing or treating the particular disorder or infection. Alleviation of one or more symptoms of the disorder indicates that the compound confers a clinical benefit.

Methods of Treatment

The invention provides for both prophylactic and therapeutic methods of treating a subject at risk of (or susceptible to) a MERS-CoV-related disease or disorder.

Prophylactic Methods

In one aspect, the invention provides methods for preventing a MERS-CoV-related disease or disorder in a subject by administering to the subject a monoclonal antibody of the invention or an agent identified according to the methods of the invention. For example, monoclonal antibody 1E9, 1F10, 3B12, 3A1, 3C12, 3B11 or M14D3, and any variants thereof, may be administered in therapeutically effective amounts. Optionally, two or more anti-MERS-CoV antibodies are co-administered.

Subjects at risk for a MERS-CoV-related diseases or disorders include patients who have been exposed to the MERS-CoV. For example, the subjects have traveled to regions or countries of the world in which other MERS-CoV infections have been reported and confirmed. Administration of a prophylactic agent can occur prior to the manifestation of symptoms characteristic of the MERS-CoV-related disease or disorder, such that a disease or disorder is prevented or, alternatively, delayed in its progression.

The appropriate agent can be determined based on screening assays described herein. Alternatively, or in addition, the agent to be administered is a monoclonal antibody that neutralizes a MERS-CoV that has been identified according to the methods of the invention. In some embodiments, the antibody of the present invention can be administered with other antibodies or antibody fragments known to neutralize MERS-CoV. Administration of said antibodies can be sequential, concurrent, or alternating.

Therapeutic Methods

Another aspect of the invention pertains to methods of treating a MERS-CoV-related disease or disorder in a patient. In one embodiment, the method involves administering an agent (e.g., an agent identified by a screening assay described herein and/or monoclonal antibody identified according to the methods of the invention), or combination of agents that neutralize the MERS-CoV to a patient suffering from the disease or disorder.

Combinatory Methods

The invention provides treating a MERS-CoV-related disease or disorder, in a patient by administering two or more antibodies wherein the Fc region of said variant does not bind or has reduced binding to the Fc gamma receptor, with other MERS-CoV neutralizing antibodies known in the art, such as mAb11. In another embodiment, the invention provides methods for treating a MERS-CoV-related disease or disorder in a patient by administering an antibody of the present invention, such as 1E9, 1F10, 3B12, 3A1, 3C12, 3B11 or M14D3 as described herein, with any anti-viral agent known in the art. Anti-viral agents can be peptides, nucleic acids, small molecules, inhibitors, or RNAi.

The invention will be further described in the following examples, which do not limit the scope of the invention described in the claims.

EXAMPLES

Example 1 General Methods

Expression and Purification of the MERS-CoV Spike.

Figure 6:
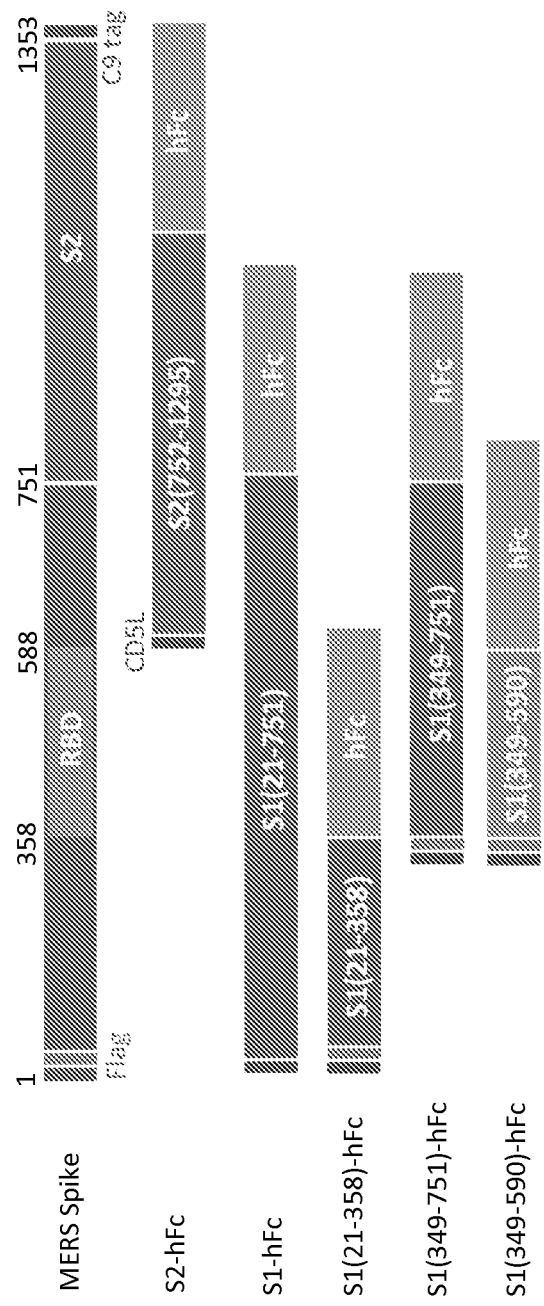
FIG. 6 Schematic representation of the MERS-CoV spike (S) protein and soluble spike constructs used in this study. hFc: the hinge-CH2-CH3 of the human IgG1 heavy chain constant region.

The MERS-CoV S gene (according to GenBank accession number: JX869059) was codon-optimized and synthesized for mammalian cell expression. The full-length spike with a Flag tag (DYKDDDDK) at its N terminus (between the signal peptide and the extracellular domain of the S protein) and a C9 tag (TETSQVAPA) at its C terminus was first cloned into the pcDNA3.1 vector. A series of constructs encoding different fragments of MERS-CoV spike protein were subsequently designed. Plasmids encoding MERS-CoV S protein residues 21-751, 752-1295, 21-358, 349-751, and 349-590 fused with the CD5 signal peptide and the constant region fragment of human IgG1 were named S1-hFc, S2-hFc, S1(21-358)-hFc, S1(349-571)-hFc, and S1(349-590)-hFc (RBD-hFc), respectively (FIG. 6). The latter three constructs also have Flag tags at their N termini. Fc-tagged proteins were expressed from transiently transfected 293T cells and purified with protein A Sepharose (GE Healthcare).

Stable 293T Cells Expressing MERS-CoV Spike or Human DPP4.

Full-length S with an N-terminal Flag tag and a C-terminal C9 tag was cloned into the pHAGE lentiviral vector, which can express both S and ZsGreen via an IRES sequence. Corresponding lentiviral particles pseudotyped with VSV-G envelope proteins were produced from Lenti-X 293T cells as described and were used for 293T cell transduction (57). The cells expressing the MERS S protein were then sorted by flow cytometry with GFP. After 2-3 weeks of propagation, stable 293T cells expressing the MERS S (S-293T) were sorted again with anti-Flag Ab and set aside for future experiments. Human DPP4 was RT-PCR-amplified from human peripheral blood mononuclear cells (PBMCs) and then cloned into a pHAGE vector without a ZsGreen reporter gene. Stable 293T cells expressing hDPP4 (293T-hDPP4) were established following a similar protocol as described above.

Preparation of MERS Spike-PMPLs.

The S-PMPLs were prepared as described elsewhere (58, 59). Briefly, $1 \times 10^8$ 293 T cells expressing the MERS-CoV S were lysed with lysis buffer and then incubated with $5 \times 10^8$ M-280 Tosylated Dynal beads (Dynal Biotech) coated with C9 tag mAb (1D4). The Spike-bound beads were extensively washed and resuspended in 1.25 ml buffer containing 100 mM $(NH_4)_2SO_4$, 20 mM Tris (pH 7.5), 10% glycerol (vol/vol), and 1 mg/ml lipid mixture, consisting of POPC/POPE/DOPA (6:3:1, Avanti Polar Lipids). The protein-liposome mixture was dialyzed to slowly remove the detergent and to allow the formation of proteoliposomes. The dialyzed beads were washed twice with 0.1% BSA/PBS and then resuspended in 0.1% BSA/PBS to $1 \times 10^9$/ml. The protein composition of S-PMPL and control 293T-PMPL cells were then analyzed by SDS-PAGE and Western blot.

Selection of Phage Abs by Panning with S-PMPLs and S-293T Cells.

Two combined human single-chain variable region fragment (scFv) libraries (Mehta I/II) (approximately 27 billion members) constructed from B cells of 57 unimmunized donors were mixed and used for selection of scFvs against MERS-CoV S. 293T cells, 293T-PMPLs, and S-PMPLs were pre-blocked in 2% BSA/2% nonfat milk/PBS for 1 h at room temperature (RT). An aliquot of the mixed phage library ($5 \times 10^{12}$ PFU) was incubated with $3 \times 10^7$ 293 T cells and $3 \times 10^7$ 293 T-PMPLs three times to remove the nonspecific phage clones. Pre-absorbed phage was incubated with $2 \times 10^7$ S-PMPLs in 2 ml of 2% BSA/2% nonfat milk/PBS for 2 h at RT with gentle shaking. Nonspecifically absorbed phages were removed by intensive washing with PBS containing 0.1% Tween 20. Specific bound phages were eluted with 100 mM triethylamine and then neutralized, amplified, and used for the next round of panning. After two rounds of panning with S-PMPL, the eluted phages were incubated directly with S-293T cells, followed by PerCP-Cy5.5-labeled anti-M13 Ab staining. PerCP-Cy5.5 and GFP double positive cells were sorted by FACS and used to infect TG1 cells. Randomly picked single phage-scFv clones were screened for specific binding to S1-hFc and S2-hFc by MSD and ELISA as previously described (35, 59). The variable regions of the heavy (VH) and light (VL) chains of MSD/ELISA-positive clones were sequenced and aligned for the identification of unique Ab clones.

Expression and Purification of scFvFcs and Whole Human IgG1.

The single-chain VH and VL gene fragments (scFvs) of unique positive clones were first cloned into a eukaryotic expression vector, where the scFv is fused in-frame with the human IgG1 hinge-CH2-CH3 domains. For production of whole human IgG1, the VH and VL gene fragments of scFv were separately subcloned into the human IgG1κ expression vector TCAE5 or the IgG1λ expression vector TCAE6. These scFvFcs/IgG1s were transiently transfected into 293F cells and the cell culture supernatants were collected twice every 72 h. The expressed scFvFcs and IgG1 were purified by protein A Sepharose affinity chromatography (GE Healthcare).

S1 Domain Epitope Mapping and Binding Competition.

Recombinant soluble S1(21-358)-hFc, S1(349-751)-hFc, and S1(349-590)-hFc were respectively immobilized to anti-Flag biosensor at 30° C. for 240 seconds. The association of 100 nM scFvFcs 1E9, 1F8, 3A1, 3B11, 3B12, 3C12 and M14D3 to each spike was measured by using an Octet RED96 (ForteBio, Inc.) for 240 seconds at 30° C. by exposing the sensors to 100 nM Ab in 1× kinetic buffer. ScFvFc of F10 was used as a non-binding control.

For the binding competition assay, recombinant soluble S1(349-590)-hFc was bound to an anti-Flag biosensor. The association of each scFvFcs was measured on the Octet RED96 for 300 seconds at 30° C. by exposing the sensors to 100 nM scFvFc in 1× kinetic buffer, after which the degree of additional binding was assessed by exposing the sensors to a second scFvFc (100 nM in 1× kinetic buffer) in the presence of the first scFvFc (100 nM) for 300 seconds at 30° C. F10 was used as a non-binding control.

Affinity Measurement by Octet.

Antibody binding affinity was determined using the same Octet RED96 instrument. Purified S1(349-590)-hFc at 5 µg/ml in 1× kinetic buffer was immobilized onto anti-Flag biosensors and incubated with varying concentrations of Abs in solution. All binding data were collected at 30° C. The experiments included 5 steps: 1) baseline (60 seconds); 2) S1(349-590)-hFc loading onto sensors (300 seconds); 3) second baseline (120 seconds); 4) association of Abs for measurement of $K_{on}$ (300 seconds); and 5) dissociation of Abs for the measurement of $K_{off}$ (600-1200 seconds). Baseline and dissociation steps were conducted in 1× kinetic buffer. Fitting curves were constructed using ForteBio Data Analysis 7.0 software.

Neutralization Assay with MERS-CoV Spike Pseudotyped Lentivirus.

MERS-CoV S pseudotyped lentiviral particles (MERS-VLPs) were produced by co-transfecting Lenti-X 293T cells with pcDNA3.1-Sf (encoding the full-length S of MERS-CoV), pHIV-Luc (encoding the luciferase reporter gene), and pCMV-AR8.2 (encoding HIV gag-pol). In a 96-well plate, 5-fold serially diluted Abs beginning at 10 µg/ml were incubated with an equal volume of pseudovirus at the final volume of 60 µl at room temperature for 1 h, and the mixture was added to the monolayer of 293T-hDPP4 cells cultured in a luminometer plate (PerkinElmer). Anti-influenza HA F10 Ab (scFvFc and IgG1) was used as the control Ab. VSV-G pseudotyped lentivirus was used as the virus control. After incubation overnight, the plate was replenished with 100 µl fresh media in each well and cultured for another 24 h. Luciferase activity was measured by using a luciferase assay kit (Promega, Madison, Wis., USA). Briefly, culture medium was removed and cells were lysed by the addition of 30 µl lysis buffer, and the relative luciferase unites (RLUs) in cell lysates were measured using a POLARstar Omega (BMG Labtech). This assay was performed in triplicate.

Plaque Reduction Neutralization Test ($PRNT_{50}$) with Live MERS-CoV.

MERS-CoV EMC/2012 was cultured on Vero cells. The neutralization assay was conducted using a $PRNT_{50}$ assay as described before (48, 60). Briefly, serial dilutions of the Abs in PBS were incubated with 100 PFU of MERS-CoV for 1 h at 37° C., and the antibody:virus mix was added to the monolayer of Vero cells, along with virus without Ab. After 1 h of incubation, overlay containing media and agarose was added, and plaques formed in each dilution were counted 48-72 h following infection. The percentage neutralization was calculated as [(100−number of plaques with Ab)/number of plaques without Ab)]×100.

Binding Competition Between scFvFcs and DPP4.

Recombinant soluble human DPP4 was purchased from Abcam. A buffer exchange step to PBS was performed using an Amicon Ultra 0.5 ml centrifugal filter (Millipore). Purified S1(349-590)-hFc was loaded onto anti-Flag biosensors and first incubated with 100 nM of each scFvFcs. Additional binding of DPP4 was measured by exposing the sensors to 100 nM DPP4 in the presence of the 100 nM scFvFc. Similarly, anti-Flag biosensors loaded with S1(349-590)-hFc was incubated with 100 nM of DPP4 followed by monitoring the subsequent binding of 100 nM scFvFc to the sensors in the presence of 100 nM DPP4. All measurements were performed on an Octet RED96.

Antibody Inhibition of Spike and MERS-VLP Binding to 293T-hDPP4 Cells.

S1(349-590)-hFc (50 nM) was incubated with scFvFcs (450, 150, 50, or 0 nM) in a 50 µl volume at 4° C. for 1 h. F10 scFvFc was used as the control. Each mixture was added to 293T-hDPP4 cells ($1 \times 10^5$) and incubated at 4° C. for 1 h. Cells were washed three times with PBS containing 0.5% BSA and 0.1% $NaN_3$. For detection of S1(349-590)-hFc binding to 293T-hDPP4 cells, cells were incubated with mouse anti-Flag Ab at 4° C. for 30 min followed by APC-Cy7-labeled goat anti-mouse IgG (Pierce). After extensive washing, samples were analyzed using a BD LSRII.

Similarly, 50 µl MERS-VLP was mixed with scFvFcs (450, 150, 50, or 0 nM) at 4° C. for 1 h. The mixtures were then separately added to 293T-hDPP4 cells. After washing, the binding of MERS-VLPs to 293T-hDPP4 cells was monitored with anti-Flag Ab staining and flow cytometry.

Isolation of the Escape Mutants Under Selective Pressure of nAbs.

MERS-CoV ($1 \times 10^6$ PFU) was incubated with 30 µg of each Ab in a 200 µl volume of PBS for 30 min and was then added to a monolayer of Vero cells. The development of cytopathic effect (CPE) was monitored over 72 h, and progeny viruses were harvested. Three rounds of selections were performed in the presence of 30 µg/ml Abs (except for 3B11 scFvFc), and CPE was noted during each passage. The viruses from final passage were plaque purified in the presence of Ab, and titers were determined as described (48). The S genes from plaque-purified viruses were sequenced to identify mutations that conferred escape from these Abs.

Escape Mutations Effect RBD-Ab Binding and Cross Neutralization.

Seven RBD mutant derivatives of S1(349-590)-hFc were constructed (Table S2) using a site-directed mutagenesis kit (Agilent, CA). The mutant RBD proteins were expressed and purified from transfected 293T cells. Seven scFvFcs' binding affinities to these RBD mutants were measured on an Octet RED96 as described above. Furthermore, Ab neutralization against escape mutants was investigated by $PRNT_{50}$ assay.

Escape Mutations Affect RBD-hDPP4 Binding and Viral Fitness.

The binding affinity of RBD mutants to hDPP4 was first measured using the Octet RED96. Because 5/7 RBD mutants have undetectable binding to hDPP4, the RBD-hDPP4 binding was further investigated by FACS. Each RBD mutants was 2× serially diluted and incubated with 1×10⁵ 293 T-hDPP4 cells in 100 μl FACS buffer. After washing 3 times, cells were stained with APC-Cy7-labeled goat anti-human IgG1. After extensive washing, the samples were analyzed by using a BD LSRII.

Virus growth kinetics were measured in triplicates by inoculating Vero cells with different escape mutants at a multiplicity of infection (MOI) of 0.1 for 1 h, after which unbound virus was washed, media was added back and supernatant was sampled at various time points. Virus titers were determined by plaque assay.

Example 2: Identification of Anti-MERS Spike Phage Abs by Sequential Spike-Containing Paramagnetic Proteoliposome (S-PMPL) and Spike-Expressing 293T Cell (S-293T) Panning Purified S-PMPLs and S-293T cells were used to select Abs from the Mehta I/II non-immune human scFv-phage libraries. After two rounds of selection with S-PMPLs and one subsequent round of selection with S-293T cells, a total of 1344 clones were screened to verify their binding to S1-hFc and S2-hFc (FIG. 6) by enzyme-linked immunosorbent assay (ELISA) or meso-scale discovery (MSD). Seventy-nine clones were positive against S1-hFc, which accounted for all of the positive clones binding to S-293T cells, as confirmed by flow cytometric analysis. Further sequencing indicated that the 79 positive clones represented seven unique anti-S1 scFvs (1E9, 1F8, 3A1, 3B12, 3C12, 3B11, and M14D3). FIG. 1 shows the amino acid sequences of these clones. Three different VH and six different VL germline sequences are represented. Five of seven VH chains belong to one gene family, IGHV1-69 (four 06 alleles and one 09 allele). Remarkably, these VH segments show very low levels of somatic hypermutation (SHM) (mean 4.3±4.2), ranging from zero (3B12, 3B11) to only 5 (3A1, 3C12) amino acid substitutions. 1E9 and 1F8 Abs use IGHV3-30 and IGHV1-3 and have 10 and 9 substitutions respectively. The VH CDR3 lengths for these 7 Abs varies from 11-19 amino acids. The VL genes are more diverse. Four VLs use κ chains, and three use λ, chains. However, they also show a low level of SHM (mean 5.3±2.4).

Example 3: S1 Domain Epitope Mapping and Binding Competition

Figure 7:
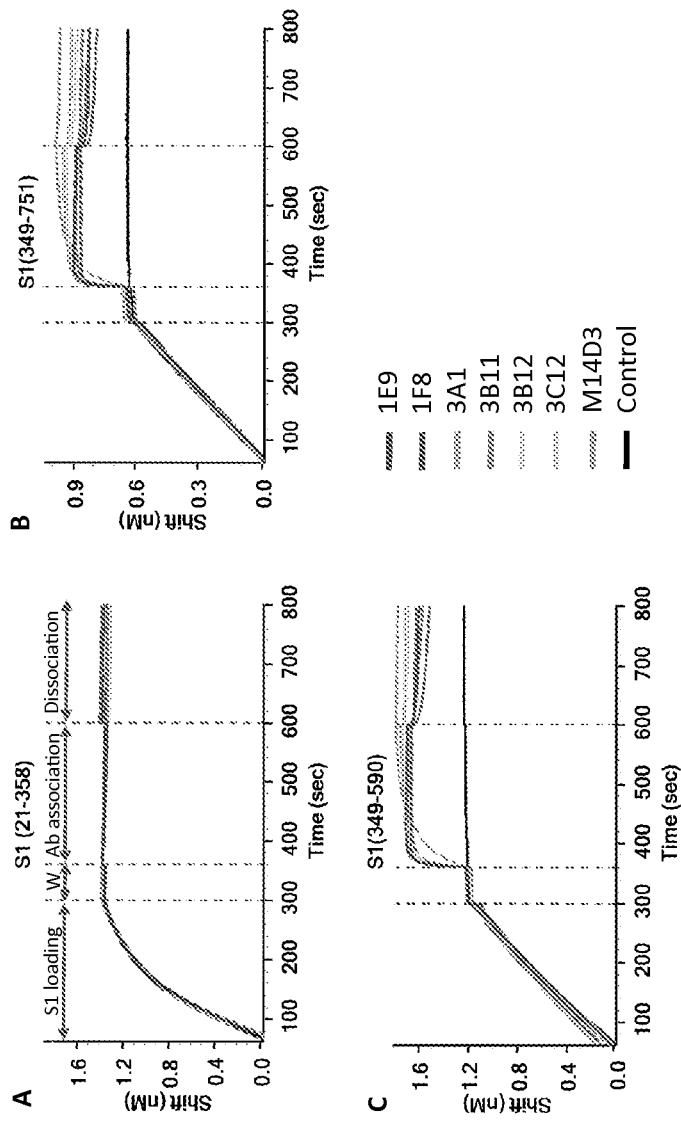
FIG. 7 Epitope mapping with three fragments of S1. Anti-Flag biosensors were immobilized with 10 μg/ml S1(21-358)-hFc (A), S1(349-751)-hFc (B), and S1(349-590)-hFc (C). After washing, each sensor was exposed to 100 nM of each scFvFc. Additional shifting during the Ab loading step indicates its binding to the S1 fragment immobilized on the sensor. F10 was used as a non-binding control.

To more precisely delineate the S1 epitopes of these Abs, the S1 domain was expressed as three fragments: S1(21-358), S1(349-751), and S1(349-590) (FIG. 6). Each fragment was designed with an N-terminal Flag tag and C-terminal human Fc tag. Binding detection with Octet showed that all seven scFvFcs recognized S1(349-751)-hFc and S1(349-590)-hFc but not S1(21-358)-hFc (FIG. 7). These results demonstrate that the epitopes of all seven Abs lie within the 349-590 amino acid fragment of the S protein, which contains the RBD of MERS-CoV RBD (36).

To determine whether these Abs recognize different epitopes, binding competition assays were performed. An anti-Flag biosensor capturing S1(349-590)-hFc was initially saturated with one Ab, and additional binding with another Ab was evaluated. The results indicate that 1E9 can completely block the binding of 1F8 and 3A1 and partially block 3B12 and M14D3 but that it does not affect the additional binding of 3B11 and 3C12 (FIG. 8A). Abs 1F8, 3A1, and 3B12 can block all other Abs' binding to S1(349-590) (FIGS. 8B, C&D). Additionally, 3B11, 3C12, and M14D3 can block the binding of 1F8, 3A1 and 3B12, but not 1E9, to S1(349-590) (FIGS. 8E, F & G). The results indicate that the seven Abs recognize at least 3 distinct epitope groups, although Ab-RBD co-crystallization will be necessary to determine the precise atomic details of the epitopes and the Ab binding orientations. Ab 1E9 recognizes one unique epitope (group 1); 1F8, 3A1, and 3B12 recognize another epitope or overlapping epitopes close to each other (group 2); and 3B11, 3C12, and M14D3 recognize a third distinct epitope or group of epitopes (group 3). In addition, the ability of epitope 2 Abs to block RBD binding of all Abs suggests that epitope 2 is most likely located centrally while epitopes 1 and 3 are flanking, a conclusion that is also supported by neutralization escape data with MERS-CoV (described below).

Figure 9:
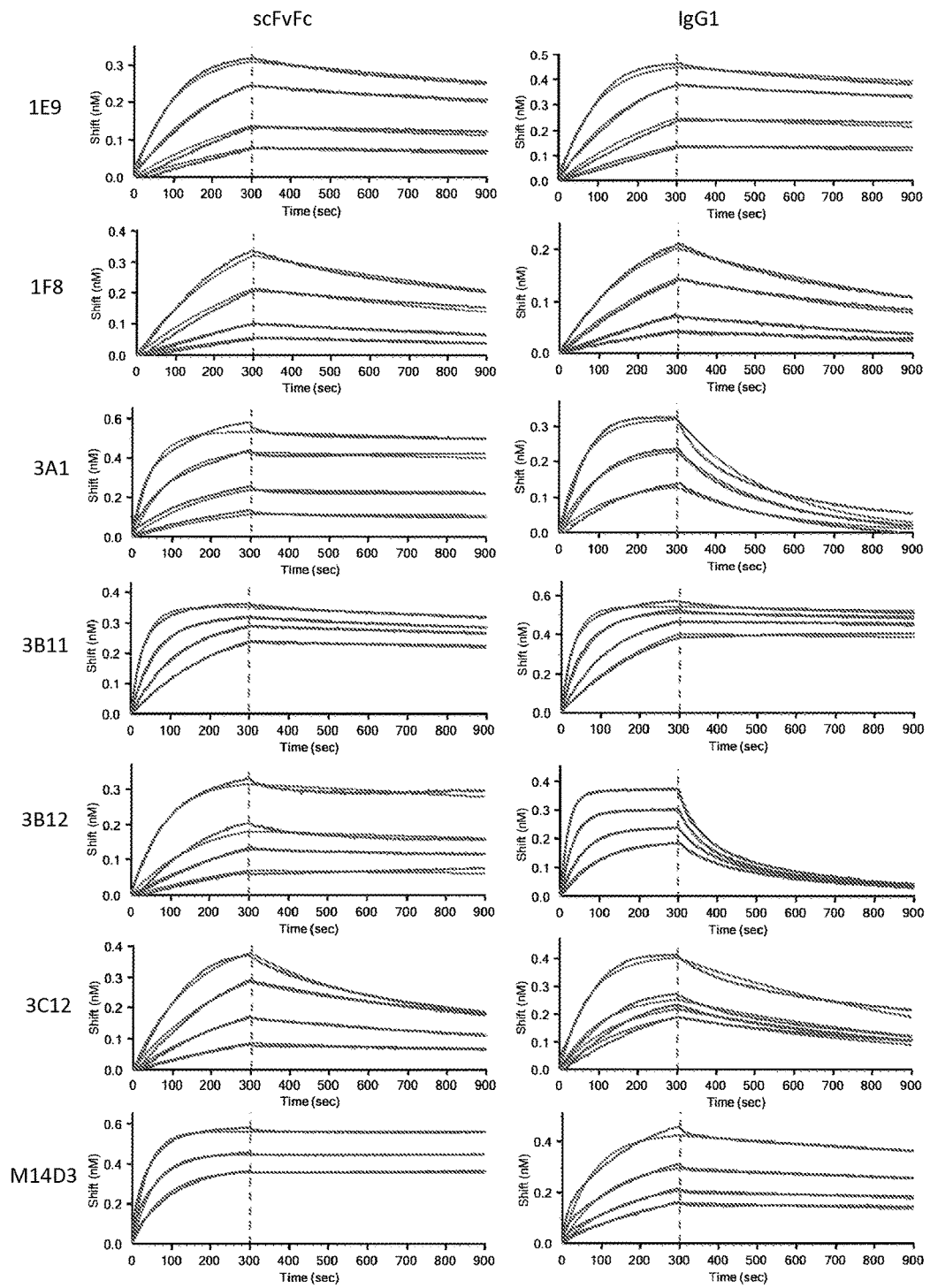
FIG. 9 Kinetic characterization of the binding of anti-S1 scFvFcs and IgGs to S1(349-590)-hFc. Purified S1(349-590)-hFc was immobilized onto anti-Flag biosensors, and various concentrations of each Ab were injected over the sensor surface. Binding kinetics were evaluated using a 1:1 binding model generated in Fortebio Data Analysis 7.0 software, with blue curves representing the experimental trace and red curves representing the best global fits for the data used to calculate the $K_d$, $K_{on}$, and $K_{off}$ (summarized in Table 1).

Example 4: Antibody Binding Affinity and Neutralization Activity of Anti-Spike scFvFcs and IgGs Binding rate constants ($K_d$, $K_{on}$, and $K_{off}$) of each scFvFc and their fully converted IgG1 forms to S1(349-590) were measured by bio-layer interferometry (BLI) using an Octet RED96 (FIG. 9). All Abs had nM to sub-nM binding affinity to S1(349-590) (Table 2). While it is uncharacteristic in our hands to see a significant loss of binding affinity on scFvFc to IgG1 format changes, conversion of 3/7 scFvFcs (3A1, 3B12, M14D3) to IgG1 resulted in ~11-34 fold higher $K_d$ values which were mostly attributable to faster $K_{off}$ rates. For the other four Abs, IgG1 forms had lower $K_d$ values than their scFvFcs and therefore higher binding affinities.

We then tested the neutralization activities of these Abs on hDPP4 expressing 293T cells (293T-hDPP4) with MERS-CoV S pseudotyped lentiviruses (VLPs) carrying a luciferase reporter gene. While all anti-MERS-S1 Abs can specifically neutralize MERS pseudovirus infection at varying efficiencies, 3B11 exhibited the best pseudovirus neutralization activity in both scFvFc and IgG1 formats (FIG. 2A, B). To investigate the possible effect of S density on the neutralization potential of the Abs we compared pseudovirus neutralization to neutralization of live MERS-CoV infection of Vero cells using plaque reduction neutralization tests ($PRNT_{50}$). The results indicated that all scFvFcs strongly neutralized MERS-CoV with varying degrees of efficiency. Abs 3B11, 3A1, 3B12, and 3C12 were very strong neutralizers, with 50% inhibitory concentration ($IC_{50}$) values ranging from 1.25 to 2 μg/ml. The other three scFvFcs, 1E9, M14D3, and 1F8, neutralized the virus with $IC_{50}$ values of 3.21, 4.3, and 6.27 μg/ml, respectively (Table 3). At concentrations ≥20 μg/ml, 6/7 scFvFcs neutralized MERS-CoV completely (FIG. 2C). Three IgG1 Abs were also tested for live virus neutralization; 3B11 had a lower $IC_{50}$ value compared to 1F8 and 3A1 IgGs (Table 3). The anti-SARS S mAb 80R did not neutralize MERS-CoV (FIG. 2D) (35).

For pseudovirus neutralization, 1F8, 1E9, 3B11, and 3C12 IgG1 had similar neutralization activities compared to their scFvFcs in agreement with their similar binding affinities while 3A1, 3B12, and M14D3 IgGs had lower neutralization activities than their scFvFcs, in agreement with their lower binding affinities (FIG. 2B, Table 2). Thus, as expected, virus neutralization potency was positively correlated with nAb binding affinity, with 3B11 being the most potent nAb in both formats.

Example 5: Mechanism(s) of MERS-COV Neutralization

Figure 3:
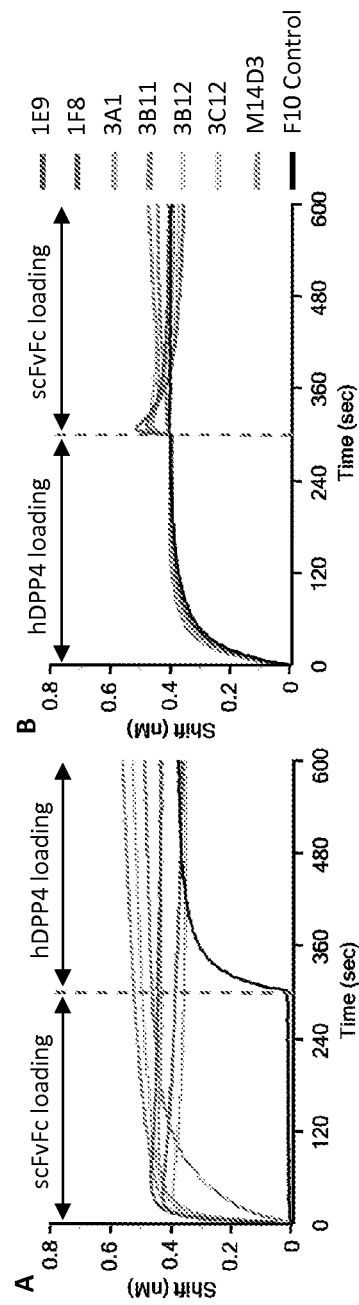
FIG. 3. Competition of binding to the MERS S RBD between anti-S1 Abs and hDPP4. Immobilized S1(349-590)-hFc (RBD-hFc) was saturated with 100 nM of scFvFc (A) or hDPP4 (B), and the RBD sensors were then exposed to hDPP4 (A) or scFvFc (B). The binding properties were monitored on an Octet RED96. F10 was used as a non-binding control.
Figure 8:
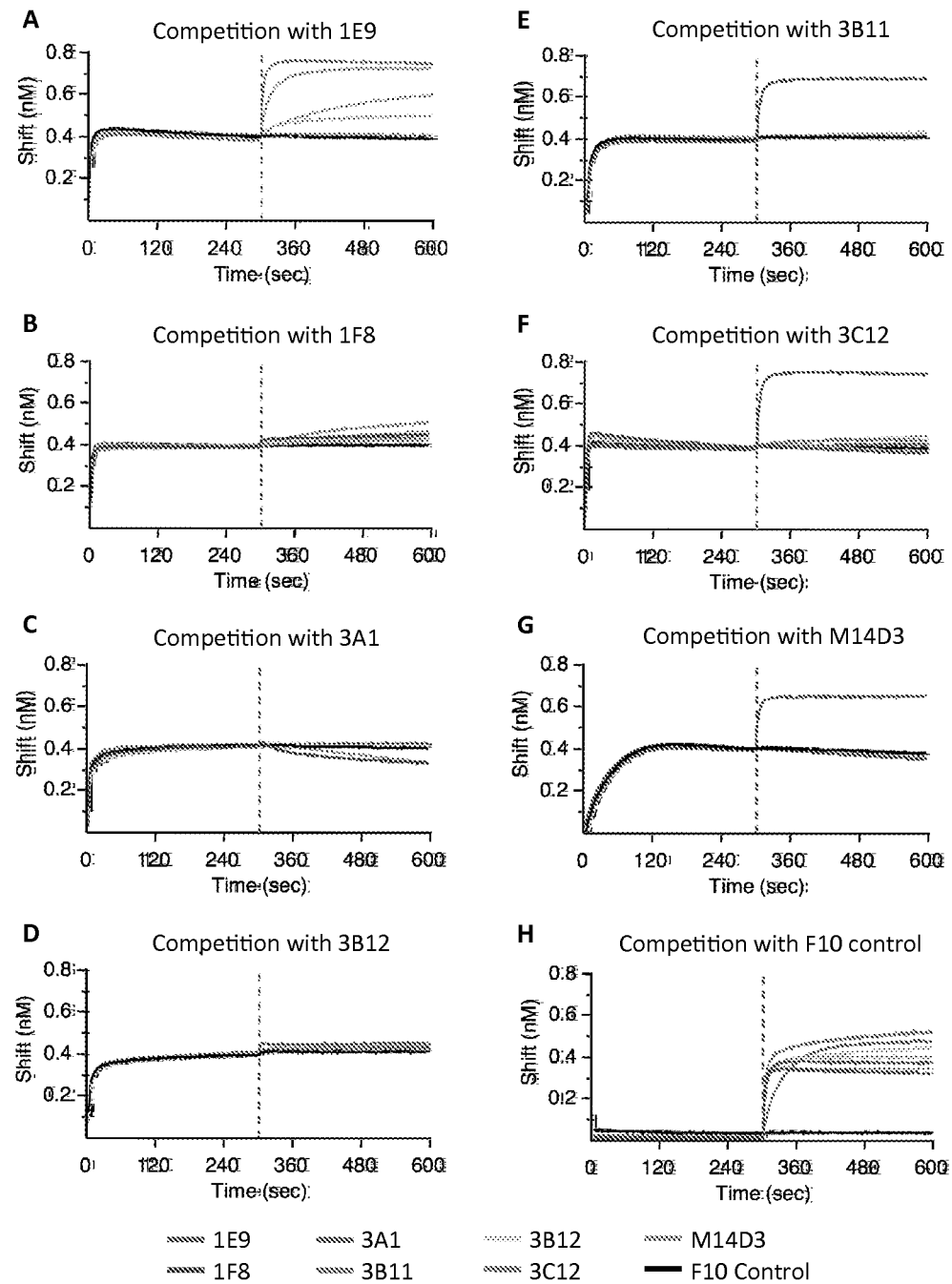
FIG. 8. Competition studies among different anti-S1 scFvFcs to S1 RBD. Immobilized S1(349-590)-hFc was firstly saturated with 100 nM of 1E9 (A), 1F8 (B), 3A1 (C), 3B12 (D), 3B11 (E), 3C12 (F), or M14D3 (G) or the F10 control, which recognizes the influenza A stem domain (H) (34). The capacity of an additional anti-S1 scFvFc binding to the sensors was monitored by measuring further shifts after injecting the second anti-S1 scFvFc (100 nM) in the presence of the first scFvFc (100 nM). The red dotted vertical line represents the 2nd scFvFc loading time. F10 was used as a non-S1 binding control.

We next explored the mechanism(s) of neutralization by investigating whether these Abs could block hDPP4 binding to the RBD and vice versa. Binding competition between hDPP4 and scFvFcs was conducted with Octet similar to detecting the competition between each Ab (FIG. 8). As shown in FIG. 3A, all scFvFcs could block hDPP4 binding to S1(349-590) while preloading of control scFvFc (F10) did not affect hDPP4 binding to S1(349-590). Similarly, hDPP4 could also block all seven scFvFcs from binding to S1(349-590) (FIG. 3B).

Figure 10:
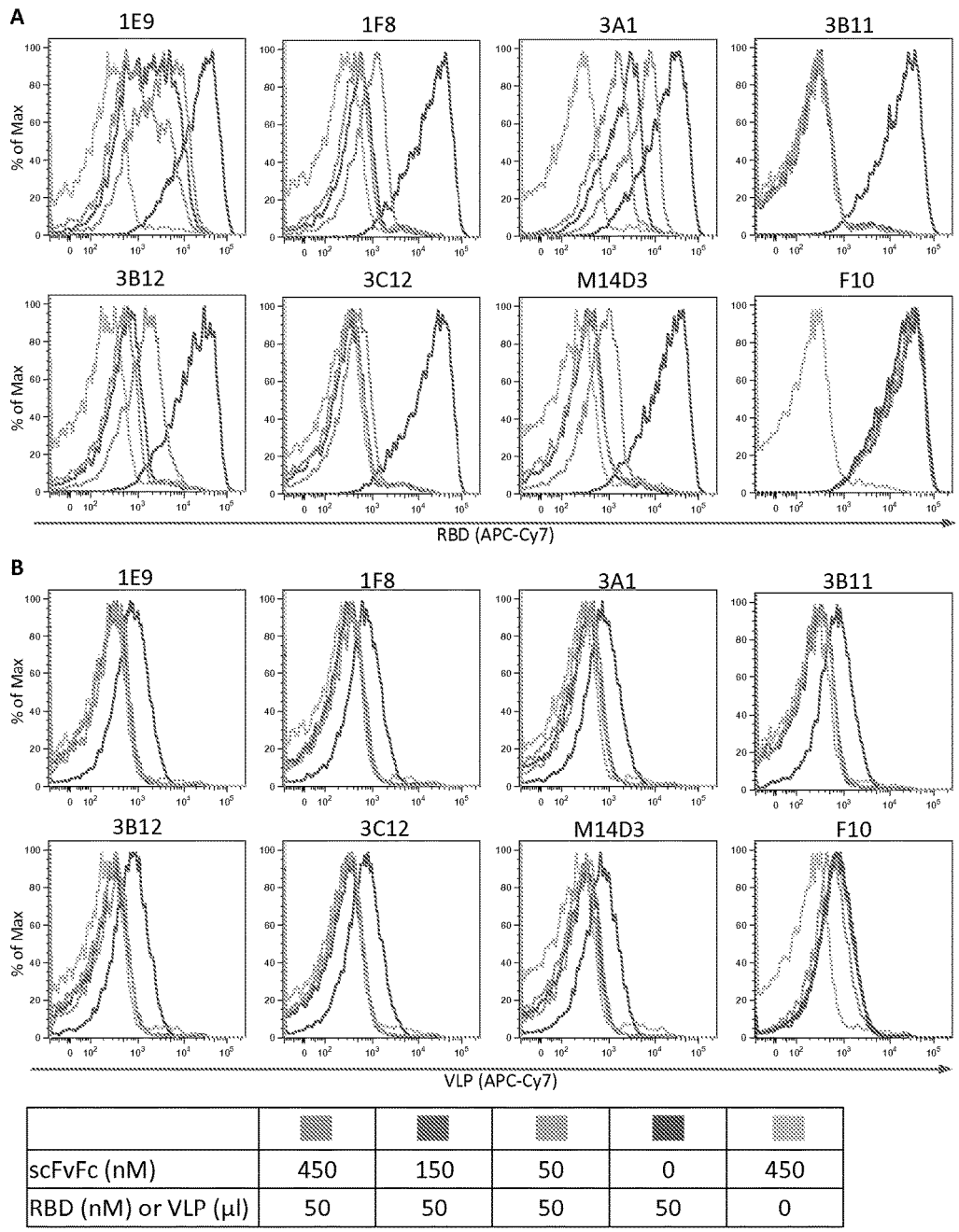
FIG. 10 Inhibition of MERS S1-RBD binding to hDPP4-expressing cells by anti-S1 scFvFcs. scFcFv Abs (0, 50, 150 or 450 nM) were used to block (A) 50 nM of soluble RBD-hFc or (B) 50 nl MERS-VLP binding to the 293T-hDPP4 cells. Binding was analyzed by flow cytometry. Each Ab is specified on top of its histogram and the Ab concentrations are noted in color at the bottom of the Figure.

To investigate whether these Abs can block virus attachment to cells, we next examined whether scFvFcs can inhibit S protein (FIG. 10A) or S-VLP (FIG. 10B) binding to hDPP4-expressing cells. As shown in FIG. 10A, all scFvFcs could inhibit 50 nM S1(349-590)-hFc binding to 293T-hDPP4 cells in a dose-dependent manner, except for 3B11, which gave maximal inhibition at all tested concentrations. The control scFvFc, F10, did not inhibit S1(349-590)-hFc binding to 293T-hDPP4. In addition, FIG. 10B shows that all scFvFcs could inhibit MERS S pseudovirus attachment to hDPP4-expressing cells.

Example 6: Generation of Antibody Escape Mutants

To investigate virus evolution under nAb pressure, we performed escape studies for all 7 scFvFcs and 3 full-length IgG1s. Upon three rounds of selective pressure in the presence of each Ab, escape mutants for all of the scFvFcs and 2 of 3 IgG Abs were generated with the exception that no escape mutant was isolated for 3B11 IgG.

To map the mutations in the S protein that conferred escape to each Ab, all escape mutants were plaque purified, and the S protein coding regions were sequenced. Only one or two amino acid substitutions conferred escape to each Ab (FIG. 4A). Interestingly, all of the escape mutations mapped to the patch 2 region in the receptor-binding motif (RBM, aa484-567) that interfaces with the human hDPP4 (FIG. 4B), except for escape mutant of 1F8 IgG1, which also had a distant substitution (I1229 T) in the S2 domain. Importantly, these escape mutations mirrored the Ab competition studies (FIG. 8) and confirmed the presence of three epitopes. Ab 1F8, 3A1, and 3B12 bind to amino acids in the center of RBM while 1E9 binds to epitope 1, and 3B11, 3C12, and M14D3 bind to another flanking epitope 3.

Example 7: Escape Mutations Affect Abs' Binding and Cross-Neutralization

To investigate the affinities of the anti-S1 Abs binding to RBD mutants, seven RBD mutants were constructed, purified and subjected to Octet analysis. As shown in Table 4, all 7 Abs could bind to the L506F mutant with 0.52- to 7.7-fold affinity changes compared to their binding to the wild type RBD. There was also a modest change of approximately 0.97- to 5.26-fold binding affinity of all Abs to the P547S mutant. In addition, with the exception of 1E9 (epitope 1 Ab), binding affinity fell below the level of Octet detection for all Abs to the other 5 RBD mutants carrying T512A, Y540C, or R542G mutations. Interestingly, 1E9 maintains good binding affinity with both the Y540C mutant and the L506F & Y540C mutant, supporting the idea that 1E9 binds to a distinct epitope 1 that does not overlap with epitope 3.

Figure 11:
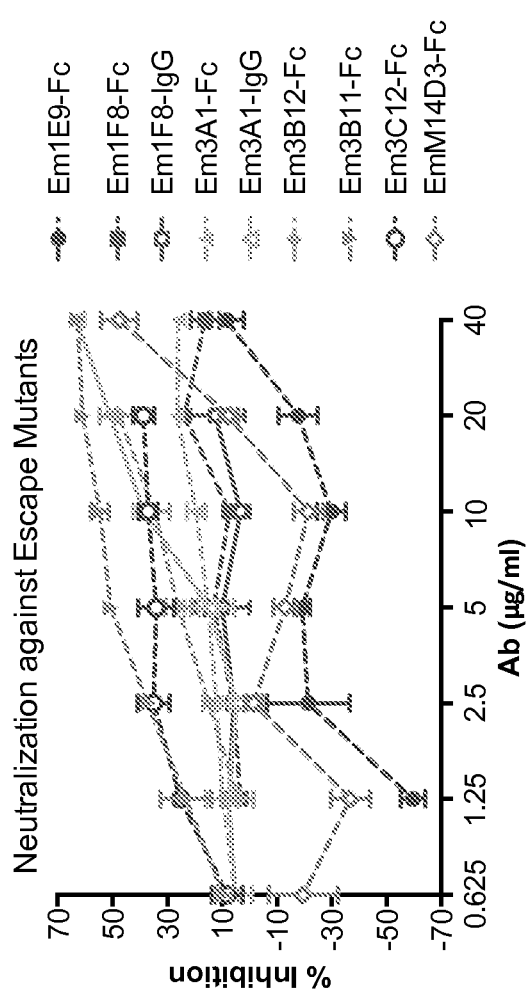
FIG. 11 Plaque reduction neutralization test (PRNT) assay for escape mutant viruses against their selecting antibodies. Abs were diluted in PBS (2× serial dilutions, starting at 40 ug/ml) and were used to block 100 PFU of escape mutant MERS-CoV infection in Vero cells. Virus with no Abs was used as control. Plaques formed in each dilution were counted 48-72 h post-infection.

Additional PRNT assays were performed to assess whether higher concentrations of the selecting Ab could neutralize its escape virus (FIG. 11). All of the escape mutants selected by these nAbs clearly escaped from their parent Abs, and eight of the escape mutants had $IC_{50}$ values ≥20 µg/ml. Only Em3B11-Fc achieved an $IC_{50}$ value of 6.76 µg/ml, a 3.7 fold increase compared to wild type (wt.) virus (Table 3).

Based on the epitope mapping studies and locations of the escape amino acid changes, mutant viruses were assigned to three epitope groups. Cross-neutralization assays ($PRNT_{50}$) were performed to analyze whether Abs of one group could still neutralize escape mutant viruses generated by Abs of another epitope group. $IC_{50}$ values (Table 5) indicated that 1E9-Fc (group 1 Ab) could still neutralize escape viruses generated from group 2 (Em1F8-Fc) and group 3 (Em3B11-Fc, Em3C12-Fc) Abs; 1F8-Fc (group 2 Ab) could neutralize escape viruses generated from the group 1 (Em1E9-Fc) Ab and the group 3 (Em3B11-Fc (Y540C & L506F)) Ab with $IC_{50}$=11.2 µg/ml, but not another group 3 (Em3C12-Fc (Y540H)) Ab with $IC_{50}$>40 µg/ml. Additionally, 3B11-Fc and 3C12-Fc (group 3 Abs) could still neutralize escape viruses from group 1 (Em1E9-Fc) and group 2 (Em1F8-Fc) Abs, although 3C12-Fc neutralizes Em1F8-Fc with an approximate 6-fold higher $IC_{50}$ (11.7 µg/ml). As expected, 1F8-Fc (group 2 Ab) did not neutralize Em3A1-Fc (group 2 escape virus) ($IC_{50}$>40 µg/ml). The 3B11-Fc (group 3 Ab) could neutralize Em3C12-Fc (group 3 escape virus) at a higher Ab concentration ($IC_{50}$=8.94 vs. 1.83 for wt.), and 3C12-Fc (group 3 Ab) could neutralize Em3B11-Fc (group 3 escape virus) at a much higher Ab concentration ($IC_{50}$=13.8 vs. 2.0 for wt.) (Table 5). These results indicate that a majority of these escape viruses generated from one Ab epitope group confer resistance to neutralization within the same Ab epitope group but not to a different Ab epitope group.

Example 8: Effects of Escape Mutations on Viral Fitness

To investigate how the escape mutations affect RBD-hDPP4 interaction and viral fitness, the binding affinities of seven mutated RBDs to hDPP4 were analyzed. As shown in Table 4, L506F and P547S had minimal effects on RBD-hDPP4 affinity while the other three mutations (T512A, Y540C, and R542G) resulted in undetectable binding between the RBD mutants and hDPP4. To further investigate these findings, the RBD mutants were analyzed for hDPP4 binding by FACS, a more sensitive measure that may detect low affinity binding. As shown in FIG. 5A, all seven mutated RBDs can bind to 293T-hDPP4 cells with varying efficacies. The P547S mutation did not change RBD binding to hDPP4 cells. However, the L506F single substitution caused a ~3-fold higher 50% effective concentration ($EC_{50}$) than the wild type RBD, while the other 5 mutants resulted in 10- to 25-fold higher $EC_{50}$ values compared to the wild type RBD.

Six escape mutant viruses were chosen for further investigation of viral fitness (note that the Em1F8-IgG, Em3A1-IgG, and EmM14D3-Fc escape viruses were not evaluated because their substitutions are at R542, the same residue as the chosen Em1F8-Fc and Em3A1-Fc escape viruses). All 6 neutralization escape viruses grew in Vero cells, reaching peak titers of $10^6$~$10^8$ plaque-forming unites (PFU)/ml by 36 h after infection (FIG. 5B). Escape mutants Em3B11-Fc and Em3A1-Fc had 1- to 2-log reductions in titer at 12~36 h after infection, compared with the wild-type virus. Em1F8-Fc, Em3B12-Fc, and Em3C12-Fc had 2- to 5-fold reductions in titer, and the Em1E9-Fc had a slightly increased viral titer. These results suggest that by kinetic and peak titer assessment most of the escape mutations resulted in impaired fitness.

We next compared the contact changes between the RBD and hDPP4 before and after neutralization escape to determine the potential atomic causes of binding affinity changes. L506, W553, and V555 in the RBD and L294 & 1295 in hDPP4 form a hydrophobic core in Patch 2 at the protein-protein interface (23). As shown in FIG. 12A, B and Table S4, the L506F substitution is predicted to result in a net decrease of 4 VDW contacts between RBD and hDPP4; however, the conserved hydrophobic L506F mutation may not appreciably change this hydrophobic core, in contrast to the significant loss of hDPP4 binding and cell entry capacity with an L506A pseudovirus (23). The P547S substitution likely does not change the interaction of the RBD and hDPP4, as it is not in direct contact with hDPP4. In addition, while the orientation of the T512 side chain is not directly in contact with hDPP4, it makes 20 internal contacts within a loop structure that connects β strands 6 and 7 (22). The T512 side chain does form an important hydrogen bond with D509 that may stabilize the loop structure (FIG. 12C). This hydrogen bond is lost with the T512A substitution, in addition to a 25% loss of other internal loop contacts (FIG. 12D). These atomic changes may alter the local conformation of the RBD, resulting in a decrease in hDPP4 binding (Table 6). In addition, while Y540 and R542 on the RBD can form hydrogen bonds with T265 and L294 on hDPP4, respectively (FIG. 12A), Y540C mutation results in a shorter side chain, and the R542G substitution removes the side chain of this residue. These two substitutions may dramatically change the RBD-hDPP4 interaction, which is illustrated in FIGS. 12A&B and Table 6, where Y540C and R542G substitutions resulted in net 4 and 11 VDW contact decreases between the RBD and hDPP4, respectively.

TABLE 2

Kinetic rates and binding affinity of anti-MERS-CoV antibodies

| | scFvFc | | | IgG | | | IgG/scFvFc* | | |
|---|---|---|---|---|---|---|---|---|---|
| Ab | $K_d$ (M) | $K_{on}$ (1/Ms) | $K_{off}$ (1/s) | $K_d$ (M) | $K_{on}$ (1/Ms) | $K_{off}$ (1/s) | $K_d$ | $K_{on}$ | $K_{off}$ |
| 1E9 | 4.13E−10 | 7.91E+05 | 3.26E−04 | 2.61E−10 | 8.75E+05 | 2.28E−04 | 0.63 | 1.11 | 0.70 |
| 1F8 | 1.58E−09 | 6.68E+05 | 1.05E−03 | 1.11E−09 | 6.52E+05 | 7.22E−04 | 0.70 | 0.98 | 0.69 |
| 3B12 | 1.76E−10 | 1.16E+06 | 2.04E−04 | 2.24E−09 | 2.09E+06 | 4.68E−03 | 12.73 | 1.80 | 22.94 |
| 3A1 | 2.25E−10 | 5.04E+05 | 1.13E−04 | 2.43E−09 | 1.68E+06 | 4.08E−03 | 10.80 | 3.33 | 36.11 |
| 3C12 | 2.01E−09 | 4.85E+05 | 9.76E−04 | 4.44E−10 | 2.82E+06 | 1.25E−03 | 0.22 | 5.81 | 1.28 |
| 3B11 | 1.35E−10 | 1.21E+06 | 1.64E−04 | 5.70E−11 | 1.24E+06 | 7.06E−05 | 0.42 | 1.02 | 0.43 |
| M14D3 | 4.74E−11 | 1.58E+05 | 7.51E−06 | 1.59E−09 | 1.61E+05 | 2.56E−04 | 33.54 | 1.02 | 34.09 |

The kinetic constants were obtained by global analysis using a 1:1 binding model using Fortebio Data Analysis 7.0 software.
*Ratio of each rate. $K_d$: dissociation constant, $K_{on}$: association rate, $K_{off}$: dissociation rate.

TABLE 3

Abs' $IC_{50}$ against wild type (wt.) and escape mutant (mt.) virus

| Selecting Ab | Escape Mutation | | $IC_{50}$ (µg/ml) | |
|---|---|---|---|---|
| | Nucleotide | Amino Acid | wt. | mt. |
| 1E9-Fc | C23089U | P547S | 3.21 | >40 |
| 1F8-Fc | A23074G | R542G | 6.27 | >40 |
| 1F8-IgG | G23076C, U25136C | R542S; I1229T | 4.05 | >40 |
| 3A1-Fc | G23075C/U | R542T | 1.46 | >40 |
| 3A1-IgG | G23075A | R542K | 4.50 | 20 |
| 3B12-Fc | A22984G, C22966U | L506F, T512A | 1.25 | >20 |
| M14D3-FC | G23075A | R542K | 4.30 | >40 |
| 3B11-Fc | A23069G, C22966U | L506F, Y540C | 1.83 | 6.76 |
| 3B11-IgG | NA* | NA | 3.50 | NA |
| 3C12-Fc | U23068C | Y540H | 2.00 | >40 |

*NA, not available since no escape mutant was isolated from 3B11-IgG.

TABLE 4

$K_d$ values of RBD mutants binding to the scFvFcs and hDPP4 ($10^{-10}$M)

| RBD mutant | Selecting Ab | 1E9 | 1F8 | 3A1 | 3B12 | 3B11 | 3C12 | M14D3 | hDPP4 |
|---|---|---|---|---|---|---|---|---|---|
| L506F | 3B11, 3B12 | 2.15 | 10.8 | 2.61 | 6.42 | 3.30 | 15.1 | 3.62 | 307 |
| | | (0.52) | (0.68) | (1.16) | (3.65) | (2.44) | (0.75) | (7.7) | (1.43) |
| T512A | 3B12 | — | — | — | — | — | — | — | — |
| Y540C | 3B11, 3C12 | 4.49 | — | — | — | — | — | — | — |
| | | (1.09) | | | | | | | |
| R542G | 1F8, 3A1, M14D3 | — | — | — | — | — | — | — | — |
| P547S | 1E9 | — | 23.7 | 6.27 | 9.26 | 1.70 | 19.5 | 1.68 | 182 |
| | | | (1.5) | (2.79) | (5.26) | (1.26) | (0.97) | (3.57) | (0.85) |

TABLE 4-continued $K_d$ values of RBD mutants binding to the scFvFcs and hDPP4 $(10^{-10}M)$

| RBD mutant | Selecting Ab | 1E9 | 1F8 | 3A1 | 3B12 | 3B11 | 3C12 | M14D3 | hDPP4 |
|---|---|---|---|---|---|---|---|---|---|
| L506F, T512A | 3B12 | — | — | — | — | — | — | — | — |
| L506F, Y540C | 3B11 | 3.80 (0.92) | — | — | — | — | — | — | — |
| Wild type RBD | | 4.13 | 15.8 | 2.25 | 1.76 | 1.35 | 20.1 | 0.47 | 214 |

—: undetectable.
Numbers in brackets are $K_d$ ratios divided by $K_d$ of Ab or hDPP4 binding to wild type RBD

TABLE 5

IC$_{50}$ for neutralization of selected nAb escape mutant viruses (μg/ml)

| Ab | Em1E9-Fc (Group 1) | Em1F8-Fc (Group 2) | Em3B11-Fc (Group 3) | Em3C12-Fc (Group 3) |
|---|---|---|---|---|
| 1E9-Fc | >40 | <0.625 | 0.84 | <0.625 |
| 1F8-Fc | 12.8 | >40 | 11.2 | >40 |
| 3B11-Fc | 1.50 | 0.88 | 6.76 | 8.94 |
| 3C12-Fc | <0.625 | 11.7 | 13.8 | >40 |

TABLE 6

Contact change between 5 key RBD residues and neighboring amino acids before and after mutation (d ≤ 5.0 Å)

| wt. RBD | VDW Contact | mt. RBD | VDW Contact |
|---|---|---|---|
| With hDPP4 | | | |
| L506 | 7 | F506 | 3 |
| T512 | 0 | A512 | 0 |
| Y540 | 7 | C540 | 3 |
| R542 | 11 | G542 | 0 |
| P547 | 0 | S547 | 0 |
| Within RBD | | | |
| T512 | 20 | A512 | 15 |

Figure 12:
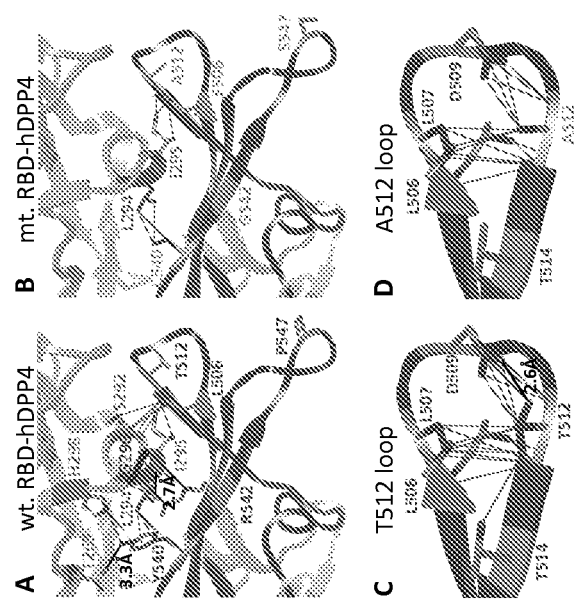
FIG. 12 Structural details of the interfaces between hDPP4 and the MERS S wild type or mutant RBDs. The interface structure was adapted from PDB ID 4KR0, with hDPP4 displayed in gray and the spike RBD represented as the RBM in purple and the receptor-binding core in light blue. Five escape mutation residues are in dictated in green before mutation (A, C) or cyan after mutation (B, D). The hDPP4 residues 265, 292, 294-296, and 298 in contact with the mutations in RBD are labeled. The van der Waals' (VDW) interactions are shown as red lines. Hydrogen bonds at S7A and S7C are shown as black lines.

Detailed contacts are shown in FIG. 12.

TABLE 7

Amino Acid Sequence of the Spike Protein (SPIKE_CVHSA)

Spike protein

SEQ ID NO: 58
MFIFLLFLTLTSGSDLDRCTTFDDVQAPNYTQHTSSMRGVYYPDEIFRSD
TLYLTQDLFLPFYSNVTGFHTINHTFGNPVIPFKDGIYFAATEKSNVVRG
WVFGSTMNNKSQSVIIINNSTNVVIRACNFELCDNPFFAVSKPMGTQTHT
MIFDNAFNCTFEYISDAFSLDVSEKSGNFKHLREFVFKNKDGFLYVYKGY
QPIDVVRDLPSGFNTLKPIFKLPLGINITNFRAILTAFSPAQDIWGTSAA
AYFVGYLKPTTFMLKYDENGTITDAVDCSQNPLAELKCSVKSFEIDKGIY
QTSNFRVVPSGDVVRFPNITNLCPFGEVFNATKFPSVYAWERKKISNCVA
DYSVLYNSTFFSTFKCYGVSATKLNDLCFSNVYADSFVVKGDDVRQIAPG
QTGVIADYNYKLPDDFMGCVLAWNTRNIDATSTGNYNYKYRYLRHGKLRP
FERDISNVPFSPDGKPCTPPALNCYWPLNDYGFYTTTGIGYQPYRVVVLS
FELLNAPATVCGPKLSTDLIKNQCVNFNFNGLTGTGVLTPSSKRFQPFQQ

TABLE 7-continued

Amino Acid Sequence of the Spike Protein (SPIKE_CVHSA)

FGRDVSDFTDSVRDPKTSEILDISPCSFGGVSVITPGTNASSEVAVLYQD
VNCTDVSTAIHADQLTPAWRIYSTGNNVFQTQAGCLIGAEHVDTSYECDI
PIGAGICASYHTVSLLRSTSQKSIVAYTMSLGADSSIAYSNNTIAIPTNF
SISITTEVMPVSMAKTSVDCNMYICGDSTECANLLLQYGSFCTQLNRALS
GIAAEQDRNTREVFAQVKQMYKTPTLKYFGGFNFSQILPDPLKPTKRSFI
EDLLFNKVTLADAGFMKQYGECLGDINARDLICAQKFNGLTVLPPLLTDD
MIAAYTAALVSGTATAGWTFGAGAALQIPFAMQMAYRFNGIGVTQNVLYE
NQKQIANQFNKAISQIQESLTTTSTALGKLQDVVNQNAQALNTLVKQLSS
NFGAISSVLNDILSRLDKVEAEVQIDRLITGRLQSLQTYVTQQLIRAAEI
RASANLAATKMSECVLGQSKRVDFCGKGYHLMSFPQAAPHGVVFLHVTYV
PSQERNFTTAPAICHEGKAYFPREGVFVFNGTSWFITQRNFFSPQIITTD
NTFVSGNCDVVIGIINNTVYDPLQPELDSFKEELDKYFKNHTSPDVDLGD
ISGINASVVNIQKEIDRLNEVAKNLNESLIDLQELGKYEQYIKWPWYVWL
GFIAGLIAIVMVTILLCCMTSCCSCLKGACSCGSCCKFDEDDSEPVLKGV
KLHYT

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Zaki A M, van Boheemen S, Bestebroer T M, Osterhaus A D, & Fouchier R A (2012) Isolation of a novel coronavirus from a man with pneumonia in Saudi Arabia. *N Engl J Med* 367(19):1814-1820.
2. Breban R, Riou J, & Fontanet A (2013) Interhuman transmissibility of Middle East respiratory syndrome coronavirus: estimation of pandemic risk. *Lancet* 382 (9893):694-699.
3. Health Protection Agency UKNCIt (2013) Evidence of person-to-person transmission within a family cluster of novel coronavirus infections, United Kingdom, February 2013. *Euro Surveill* 18(11):20427.
4. Cotten M, et al. (2014) Spread, circulation, and evolution of the middle East respiratory syndrome coronavirus. *MBio* 5(1):e01062-01013.

5. Li W, et al. (2005) Receptor and viral determinants of SARS-coronavirus adaptation to human ACE2. *EMBO J* 24(8):1634-1643.
6. Chinese SMEC (2004) Molecular evolution of the SARS coronavirus during the course of the SARS epidemic in China. *Science* 303(5664):1666-1669.
7. Annan A, et al. (2013) Human betacoronavirus 2c EMC/2012-related viruses in bats, Ghana and Europe. *Emerg Infect Dis* 19(3):456-459.
8. Anthony S J, et al. (2013) Coronaviruses in bats from Mexico. *J Gen Virol* 94(Pt 5):1028-1038.
9. Woo P C, et al. (2006) Molecular diversity of coronaviruses in bats. *Virology* 351(1):180-187.
10. Memish Z A, et al. (2013) Middle East respiratory syndrome coronavirus in bats, Saudi Arabia. *Emerg Infect Dis* 19(11):1819-1823.
11. Perera R A, et al. (2013) Seroepidemiology for MERS coronavirus using microneutralisation and pseudoparticle virus neutralisation assays reveal a high prevalence of antibody in dromedary camels in Egypt, June 2013. *Euro Surveill* 18(36):pii=20574.
12. Reusken C B, et al. (2013) Middle East respiratory syndrome coronavirus neutralising serum antibodies in dromedary camels: a comparative serological study. *Lancet Infect Dis* 13(10):859-866.
13. Haagmans B L, et al. (2014) Middle East respiratory syndrome coronavirus in dromedary camels: an outbreak investigation. *Lancet Infect Dis* 14(2):140-145.
14. Meyer B, et al. (2014) Antibodies against MERS Coronavirus in Dromedary Camels, United Arab Emirates, 2003 and 2013. *Emerg Infect Dis* 20(4):10.3201/eid2004.131746.
15. Alagaili A N, et al. (2014) Middle East respiratory syndrome coronavirus infection in dromedary camels in saudi arabia. *MBio* 5(2):e00884-00814.
16. Eckerle I, et al. (2014) Replicative Capacity of MERS Coronavirus in Livestock Cell Lines. *Emerg Infect Dis* 20(2):276-279.
17. Muller M A, et al. (2012) Human coronavirus EMC does not require the SARS-coronavirus receptor and maintains broad replicative capability in mammalian cell lines. *MBio* 3(6):e00515-00512.
18. Hofmann H, et al. (2004) S protein of severe acute respiratory syndrome-associated coronavirus mediates entry into hepatoma cell lines and is targeted by neutralizing antibodies in infected patients. *J Virol* 78(12):6134-6142.
19. Chan K H, et al. (2013) Cross-reactive antibodies in convalescent SARS patients' sera against the emerging novel human coronavirus EMC (2012) by both immunofluorescent and neutralizing antibody tests. *J Infect* 67(2):130-140.
20. Gierer S, et al. (2013) The spike protein of the emerging betacoronavirus EMC uses a novel coronavirus receptor for entry, can be activated by TMPRSS2, and is targeted by neutralizing antibodies. *J Virol* 87(10):5502-5511.
21. Raj V S, et al. (2013) Dipeptidyl peptidase 4 is a functional receptor for the emerging human coronavirus-EMC. *Nature* 495(7440):251-254.
22. Lu G, et al. (2013) Molecular basis of binding between novel human coronavirus MERS-CoV and its receptor CD26. *Nature* 500(7461):227-231.
23. Wang N, et al. (2013) Structure of MERS-CoV spike receptor-binding domain complexed with human receptor DPP4. *Cell Res* 23(8):986-993.
24. Falzarano D, et al. (2013) Treatment with interferon-alpha2b and ribavirin improves outcome in MERS-CoV-infected rhesus macaques. *Nat Med* 19(10):1313-1317.
25. Agnihothram S, et al. (2013) Evaluation of Serologic and Antigenic Relationships Between Middle Eastern Respiratory Syndrome Coronavirus and Other Coronaviruses to Develop Vaccine Platforms for the Rapid Response to Emerging Coronaviruses. *J Infect Dis,* 10.1093/infdis/jit1609.
26. Du L, et al. (2013) A Truncated Receptor-Binding Domain of MERS-CoV Spike Protein Potently Inhibits MERS-CoV Infection and Induces Strong Neutralizing Antibody Responses: Implication for Developing Therapeutics and Vaccines. *PLoS One* 8(12):e81587.
27. Song F, et al. (2013) Middle East respiratory syndrome coronavirus spike protein delivered by modified vaccinia virus Ankara efficiently induces virus-neutralizing antibodies. *J Virol* 87(21):11950-11954.
28. Marasco W A & Sui J (2007) The growth and potential of human antiviral monoclonal antibody therapeutics. *Nat Biotechnol* 25(12):1421-1434.
29. Gould L H, et al. (2005) Protective and therapeutic capacity of human single-chain Fv-Fc fusion proteins against West Nile virus. *J Virol* 79(23):14606-14613.
30. Kashyap A K, et al. (2008) Combinatorial antibody libraries from survivors of the Turkish H5N1 avian influenza outbreak reveal virus neutralization strategies. *Proc Natl Acad Sci USA* 105(16):5986-5991.
31. Traggiai E, et al. (2004) An efficient method to make human monoclonal antibodies from memory B cells: potent neutralization of SARS coronavirus. *Nat Med* 10(8):871-875.
32. Corti D, et al. (2011) A neutralizing antibody selected from plasma cells that binds to group 1 and group 2 influenza A hemagglutinins. *Science* 333(6044):850-856.
33. Throsby M, et al. (2008) Heterosubtypic neutralizing monoclonal antibodies cross-protective against H5N1 and H1N1 recovered from human IgM+ memory B cells. *PLoS One* 3(12):e3942.
34. Sui J, et al. (2009) Structural and functional bases for broad-spectrum neutralization of avian and human influenza A viruses. *Nat Struct Mol Biol* 16(3):265-273.
35. Sui J, et al. (2004) Potent neutralization of severe acute respiratory syndrome (SARS) coronavirus by a human mAb to S1 protein that blocks receptor association. *Proc Natl Acad Sci USA* 101(8):2536-2541.
36. Mou H, et al. (2013) The receptor binding domain of the new Middle East respiratory syndrome coronavirus maps to a 231-residue region in the spike protein that efficiently elicits neutralizing antibodies. *J Virol* 87(16):9379-9383.
37. Sui J, et al. (2008) Broadening of neutralization activity to directly block a dominant antibody-driven SARS-coronavirus evolution pathway. *PLoS Pathog* 4(11):e1000197.
38. Wrammert J, et al. (2008) Rapid cloning of high-affinity human monoclonal antibodies against influenza virus. *Nature* 453(7195):667-671.
39. Corti D & Lanzavecchia A (2013) Broadly neutralizing antiviral antibodies. *Annu Rev Immunol* 31705-742.
40. Wu X, et al. (2011) Focused evolution of HIV-1 neutralizing antibodies revealed by structures and deep sequencing. *Science* 333(6049):1593-1602.
41. Chan C H, Hadlock K G, Foung S K, & Levy S (2001) V(H)1-69 gene is preferentially used by hepatitis C virus-associated B cell lymphomas and by normal B cells responding to the E2 viral antigen. *Blood* 97(4):1023-1026.

42. Huang C C, et al. (2004) Structural basis of tyrosine sulfation and VH-gene usage in antibodies that recognize the HIV type 1 coreceptor-binding site on gp120. *Proc Natl Acad Sci USA* 101(9):2706-2711.
43. Boyd S D, et al. (2010) Individual variation in the germline Ig gene repertoire inferred from variable region gene rearrangements. *J Immunol* 184(12):6986-6992.
44. Watson C T & Breden F (2012) The immunoglobulin heavy chain locus: genetic variation, missing data, and implications for human disease. *Genes Immun* 13(5):363-373.
45. Farci P, et al. (2010) B cell gene signature with massive intrahepatic production of antibodies to hepatitis B core antigen in hepatitis B virus-associated acute liver failure. *Proc Natl Acad Sci USA* 107(19):8766-8771.
46. Assiri A, et al. (2013) Hospital outbreak of Middle East respiratory syndrome coronavirus. *N Engl J Med* 369(5): 407-416.
47. Memish Z A, Zumla A I, Al-Hakeem R F, Al-Rabeeah A A, & Stephens G M (2013) Family cluster of Middle East respiratory syndrome coronavirus infections. *N Engl J Med* 368(26):2487-2494.
48. Rani M, et al. (2012) Increased antibody affinity confers broad in vitro protection against escape mutants of severe acute respiratory syndrome coronavirus. *J Virol* 86(17): 9113-9121.
49. Rockx B, et al. (2010) Escape from human monoclonal antibody neutralization affects in vitro and in vivo fitness of severe acute respiratory syndrome coronavirus. *J Infect Dis* 201(6):946-955.
50. Cotten M, et al. (2013) Transmission and evolution of the Middle East respiratory syndrome coronavirus in Saudi Arabia: a descriptive genomic study. *Lancet* 382 (9909):1993-2002.
51. Bermingham A, et al. (2012) Severe respiratory illness caused by a novel coronavirus, in a patient transferred to the United Kingdom from the Middle East, September 2012. *Euro Surveill* 17(40):20290.
52. Cotten M, et al. (2013) Full-genome deep sequencing and phylogenetic analysis of novel human betacoronavirus. *Emerg Infect Dis* 19(5):736-742B.
53. Consortium IISAREI (2013) Treatment of MERS-CoV: Decision Support Tool.
54. ter Meulen J, et al. (2006) Human monoclonal antibody combination against SARS coronavirus: synergy and coverage of escape mutants. *PLoS Med* 3(7):e237.
55. Bakker A B, et al. (2008) First administration to humans of a monoclonal antibody cocktail against rabies virus: safety, tolerability, and neutralizing activity. *Vaccine* 26(47):5922-5927.
56. Dimitrov D S (2010) Therapeutic antibodies, vaccines and antibodyomes. *MAbs* 2 (3):347-356.
57. Taube R, et al. (2008) Lentivirus display: stable expression of human antibodies on the surface of human cells and virus particles. *PLoS One* 3(9):e3181.
58. Mirzabekov T, Kontos H, Farzan M, Marasco W, & Sodroski J (2000) Paramagnetic proteoliposomes containing a pure, native, and oriented seven-transmembrane segment protein, CCR5. *Nat Biotechnol* 18(6):649-654.
59. Xu C, Sui J, Tao H, Zhu Q, & Marasco W A (2007) Human anti-CXCR4 antibodies undergo VH replacement, exhibit functional V-region sulfation, and define CXCR4 antigenic heterogeneity. *J Immunol* 179(4):2408-2418.
60. Rockx B, et al. (2008) Structural basis for potent cross-neutralizing human monoclonal antibody protection against lethal human and zoonotic severe acute respiratory syndrome coronavirus challenge. *J Virol* 82(7):3220-3235.

What is claimed is:

1. An isolated monoclonal antibody, wherein said monoclonal antibody binds to an epitope in the receptor binding domain (RBD) of the spike protein of a Middle East Respiratory Syndrome coronavirus (MERS-CoV), and neutralizes MERS-CoV, and wherein the monoclonal antibody comprises a $V_H$ amino acid sequence having SEQ ID NO: 14, and a $V_L$ amino acid sequence having SEQ ID NO: 16.

2. The monoclonal antibody of claim 1, wherein said epitope is non-linear.

3. The monoclonal antibody of claim 1, wherein said epitope comprises a region within amino acids 349-590 of the spike protein when numbered in accordance with SEQ ID NO: 58.

4. The monoclonal antibody of claim 1, wherein the epitope comprises at least one amino acid at position 506, 512, 540, 542 or 547 of the spike protein when numbered in accordance with SEQ ID NO: 58.

5. The monoclonal antibody of claim 1, wherein said monoclonal antibody inhibits viral and cell membrane fusion.

6. The monoclonal antibody of claim 1, wherein said monoclonal antibody competes with the binding of monoclonal antibody 1E9, 1F8, 3B12, 3A1, 3C12, 3B11 or M14D3 to the spike protein.

7. The monoclonal antibody of claim 1, wherein said monoclonal antibody is a fully human antibody.

8. The monoclonal antibody of claim 1, wherein said monoclonal antibody blocks the binding of MERS-CoV spike protein to DPP4 receptor.

9. The monoclonal antibody of claim 1, wherein said monoclonal antibody is produced in a plant.

10. An isolated scFv antibody, wherein said antibody binds to an epitope in the receptor binding domain (RBD) of the spike protein of a Middle East Respiratory Syndrome coronavirus (MERS-CoV), and neutralizes MERS-CoV, and wherein the isolated scFv antibody comprises a $V_H$ amino acid sequence having SEQ ID NO: 14, and a $V_L$ amino acid sequence having SEQ ID NO: 16.

11. The scFv antibody of claim 10, wherein said epitope is non-linear.

12. The scFv antibody of claim 10, wherein said epitope comprises a region within amino acids 349-590 of the spike protein when numbered in accordance with SEQ ID NO: 58.

13. The scFv antibody of claim 10, wherein the epitope comprises at least one amino acid at position 506, 512, 540, 542 or 547 of the spike protein when numbered in accordance with SEQ ID NO: 58.

14. The scFv antibody of claim 10, wherein said scFv antibody inhibits viral and cell membrane fusion.

15. The scFv antibody of claim 10, wherein said scFv antibody competes with the binding of monoclonal antibody 1E9, 1F8, 3B12, 3A1, 3C12, 3B11 or M14D3 to the spike protein.

16. The scFv antibody of claim 10, wherein said monoclonal antibody blocks the binding of MERS-CoV spike protein to DPP4 receptor.

17. A composition comprising the monoclonal antibody of claim 1 and a carrier.

18. An isolated monoclonal antibody, wherein said monoclonal antibody binds to an epitope in the receptor binding domain (RBD) of the spike protein of a Middle East Respiratory Syndrome coronavirus (MERS-CoV), and neutralizes MERS-CoV, and wherein said monoclonal antibody comprises a heavy chain with three CDRs comprising the amino acid sequences GGTFSSYA (SEQ ID NO:35), IIPIFGTA (SEQ ID NO:38), and ARVGYCSSTSCHIGAFDI (SEQ ID NO:39) respectively and a light chain with three CDRs comprising the amino acid sequences QSVSSS (SEQ ID NO:55), DSS (SEQ ID NO:56), and QQYSSSPYT (SEQ ID NO:57) respectively.

19. An isolated scFv antibody, wherein said antibody binds to an epitope in the receptor binding domain (RBD) of the spike protein of a Middle East Respiratory Syndrome coronavirus (MERS-CoV), and neutralizes MERS-CoV, wherein said scFv antibody comprises a heavy chain with three CDRs comprising the amino acid sequences GGTFSSYA (SEQ ID NO:35), IIPIFGTA (SEQ ID NO:38), and ARVGYCSSTSCHIGAFDI (SEQ ID NO:39) respectively and a light chain with three CDRs comprising the amino acid sequences QSVSSS (SEQ ID NO:55), DSS (SEQ ID NO:56), and QQYSSSPYT (SEQ ID NO:57) respectively.

* * * * *

SEQUENCE LISTING

```
<160> NUMBER OF SEQ ID NOS: 94

<210> SEQ ID NO 1
<211> LENGTH: 354
<212> TYPE: DNA
<213> ORGANISM: Artificial Sequence
<220> FEATURE:
<223> OTHER INFORMATION: Synthetic polynucleotide

<400> SEQUENCE: 1
caggtgcagc tggtgcagtc tggggagggc gtggtccaac ctgggaggtc cctgagactc      60
tcctgtgtag cctctgagtt caccttcaat acttatggca tgcactgggt ccgccaggct     120
ccaggcaagg gactggagtg ggtggcagct atttcatatg atggaactaa gaaattttat     180
gcagactccc tgaagggccg attcaccatc tccagagaca attccaagaa cacgttgtat     240
ctccaaatga acagcctgag atctgaggac acggccgtgt attactgtgc gagaagtggt     300
gactccgatg cttttgatat ctggggccaa gggacaatgg tcaccgtctc ctca           354

<210> SEQ ID NO 2
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 2

Gln Val Gln Leu Val Gln Ser Gly Gly Gly Val Val Gln Pro Gly Arg
1               5                   10                  15
```

Ser Leu Arg Leu Ser Cys Val Ala Ser Glu Phe Thr Phe Asn Thr Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Thr Lys Lys Tyr Ala Asp Ser Leu
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Arg Ser Gly Asp Ser Asp Ala Phe Asp Ile Trp Gly Gln Gly Thr
            100                 105                 110

Met Val Thr Val Ser Ser
        115

<210> SEQ ID NO 3
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 3
tcctatgagc tgactcagcc acccctcagtg tccgtgtccc caggacagac agccaccatc      60
acctgctctg gagatgaatt gggggataaa tttgctttct ggtatcaaca aaagccaggc     120
cagtcccctg tgctggtcat ctatcaagat agtaagaggc cctcagggat ccctgagcga     180
ttctctggct ccaactctgg gaacacagcc actctgacca tcagcgggac ccaggctctg     240
gatgaggctg actattactg tcaggcgtgg gacagcaaca gttatgtctt cggaactggg     300
accaaggtca ccgtcctagg t                                                321

<210> SEQ ID NO 4
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 4

Ser Tyr Glu Leu Thr Gln Pro Pro Ser Val Ser Val Ser Pro Gly Gln
1               5                   10                  15

Thr Ala Thr Ile Thr Cys Ser Gly Asp Glu Leu Gly Asp Lys Phe Ala
            20                  25                  30

Phe Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Ser Asn Ser Tyr Val
                85                  90                  95

Phe Gly Thr Gly Thr Lys Val Thr Val Leu
            100                 105

<210> SEQ ID NO 5
<211> LENGTH: 360
<212> TYPE: DNA

<213> ORGANISM: Artificial Sequence
<220> FEATURE:
<223> OTHER INFORMATION: Synthetic polynucleotide

<400> SEQUENCE: 5

```
gaggtgcagc tggtgcagtc tggggctgag gtgaaggagc ctgggtcctc ggtgaaggtc      60
tcctgcaagg cttctggggg caccttcggc agttatgcta tcaactgggt gcgacaggcc     120
cctggacaaa ggcttgagtg gatgggatgg atcgacgctg ccaatggtaa cacaaaatat     180
tcacagaagt tccagggcag agtcaccatt accggagaca catccgcgag cacagcctac     240
atggaactga gcagcctgag atctgaagac acggctgtgt attactgtgc gagagatagg     300
tggatgacta cgcgggcttt tgatatctgg ggccaaggga caatggtcac cgtctcttca     360
```

<210> SEQ ID NO 6
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 6

```
Glu Val Gln Leu Val Gln Ser Gly Ala Glu Val Lys Glu Pro Gly Ser
1               5                   10                  15
Ser Val Lys Val Ser Cys Lys Ala Ser Gly Gly Thr Phe Gly Ser Tyr
            20                  25                  30
Ala Ile Asn Trp Val Arg Gln Ala Pro Gly Gln Arg Leu Glu Trp Met
        35                  40                  45
Gly Trp Ile Asp Ala Ala Asn Gly Asn Thr Lys Tyr Ser Gln Lys Phe
    50                  55                  60
Gln Gly Arg Val Thr Ile Thr Gly Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Arg Trp Met Thr Thr Arg Ala Phe Asp Ile Trp Gly Gln
            100                 105                 110
Gly Thr Met Val Thr Val Ser Ser
        115                 120
```

<210> SEQ ID NO 7
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 7

```
cagcctgtgc tgactcagcc accctcagcg tctgggaccc ccgggcagag ggtcaccatc      60
tcttgttctg gaagcagctc caacatcgga agtaattatg ttttctggta ccagcagctc     120
ccagggatgg cccccaaact cctcatctct aggaataatc agcggccctc aggggtccct     180
gaccgattct ctggctccaa gtctggcacc tcagcctccc tggccatcag tgggccccag     240
tctgaggatg aggctgatta ttactgtgca gcatgggatg acagcctgcg tggtcccgtg     300
ttcggcggag ggaccagggt gaccgtccta ggt                                  333
```

<210> SEQ ID NO 8
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 8

```
Gln Pro Val Leu Thr Gln Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Phe Trp Tyr Gln Gln Leu Pro Gly Met Ala Pro Lys Leu Leu
            35                  40                  45

Ile Ser Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Pro Gln
65                  70                  75                  80

Ser Glu Asp Glu Ala Asp Tyr Tyr Cys Ala Ala Trp Asp Asp Ser Leu
                85                  90                  95

Arg Gly Pro Val Phe Gly Gly Gly Thr Arg Val Thr Val Leu
            100                 105                 110
```

<210> SEQ ID NO 9
<211> LENGTH: 369
<212> TYPE: DNA
<213> ORGANISM: Artificial Sequence
<220> FEATURE:
<223> OTHER INFORMATION: Artificial polynucleotide

<400> SEQUENCE: 9

```
caggtgcagc tggtgcagtc tggggctgag gtgaagaagc ctgggtcctc ggtgaaggtc      60
tcctgcaagg cgtctggagg cactttcagc agctatgcag tcagctgggt gcgacaggcc     120
cctggacaag tcttgagtg gtgggaagg ataatcccta tttttggtaa ggcaaactac       180
gcacagaagt tccagggcag agtcacgata accgcggaca atccacgag cacagcctat      240
atggaactga gcagcctgag acctgaagac acggccgtat attactgtgc gagagatcag     300
gggatttcgg ccaatttcaa agatgctttt gatatctggg gccaagggac cacggtcacc     360
gtctcctca                                                             369
```

<210> SEQ ID NO 10
<211> LENGTH: 123
<212> TYPE: PRT
<213> ORGANISM: Artificial Sequence
<220> FEATURE:
<223> OTHER INFORMATION: Synthetic polynucleotide

<400> SEQUENCE: 10

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Val Ser Trp Val Arg Gln Ala Pro Gly Gln Gly Leu Glu Trp Val
            35                  40                  45

Gly Arg Ile Ile Pro Ile Phe Gly Lys Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Pro Glu Asp Thr Ala Val Tyr Tyr Cys
                85                  90                  95

Ala Arg Asp Gln Gly Ile Ser Ala Asn Phe Lys Asp Ala Phe Asp Ile
```

```
                100             105             110
Trp Gly Gln Gly Thr Thr Val Thr Val Ser Ser
            115                 120

<210> SEQ ID NO 11
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 11
gaaacgacac tcacgcagtc tccagccacc ctgtctgtgt ctccagggga aagagccacc    60
ctctcctgca gggccagtga gagtgttggc agcaacttag cctggtacca gcagaaacct   120
ggccaggctc ccagcctcct catctatggt gcatccacca gggccactgg tatcccagac   180
agattcagtg gcagtgggtc tgggacagac ttcactctca ccatcagcag cctgcagtct   240
gaagattttg cagcttatta ttgtcagcag tataataact ggccactcac cttcggccct   300
gggaccaaag tggaaatcaa a                                             321

<210> SEQ ID NO 12
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 12

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Glu Ser Val Gly Ser Asn
            20                  25                  30

Leu Ala Trp Tyr Gln Gln Lys Pro Gly Gln Ala Pro Ser Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Ala Tyr Tyr Cys Gln Gln Tyr Asn Asn Trp Pro Leu
                85                  90                  95

Thr Phe Gly Pro Gly Thr Lys Val Glu Ile Lys
            100                 105

<210> SEQ ID NO 13
<211> LENGTH: 375
<212> TYPE: DNA
<213> ORGANISM: Artificial Sequence
<220> FEATURE:
<223> OTHER INFORMATION: Synthetic polynucleotide

<400> SEQUENCE: 13
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac   180
gcacagaagt tccagggcag agtcacgatt accgcggaca atccacgag cacagcctac   240 atggagctga gcagcctgag atctgaggac acggccgtgt attactgtgc gagggtagga   300
tattgtagta gtaccagctg tcacatcggc gcttttgata tctggggcca aggaccacg   360
```

```
gtcaccgtct cctca                                                      375
```

<210> SEQ ID NO 14
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Tyr Cys Ser Ser Thr Ser Cys His Ile Gly Ala Phe
            100                 105                 110

Asp Ile Trp Gly Gln Gly Thr Thr Val Thr Val Ser Ser
        115                 120                 125

<210> SEQ ID NO 15
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 15

```
gaaacgacac tcacgcagtc tccaggcacc ctgtctttgt ctccagggga aagagccacc    60
ctctcctgca gggccagtca gagtgttagc agcagcatag cctggtatca gcagaaacct   120
gggcaggctc ccaggctcct catgtttgat tcatccacca gggccactgg tatcccagac   180
aggttcagtg gcagtgggtc tgggacagac ttcactctca acatcagcag cctagagcct   240
gaagattttg cagtgtatta ctgtcagcag tatagtagct caccttacac ttttggccag   300
gggaccaaac tggagatcaa a                                             321
```

<210> SEQ ID NO 16
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 16

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ile Ala Trp Tyr Gln Gln Lys Pro Gly Gln Ala Pro Arg Leu Leu Met
        35                  40                  45

Phe Asp Ser Ser Thr Arg Ala Thr Gly Ile Pro Asp Arg Phe Ser Gly

```
                    50                  55                  60
Ser Gly Ser Gly Thr Asp Phe Thr Leu Asn Ile Ser Ser Leu Glu Pro
 65                  70                  75                  80

Glu Asp Phe Ala Val Tyr Tyr Cys Gln Gln Tyr Ser Ser Pro Tyr
                 85                  90                  95

Thr Phe Gly Gln Gly Thr Lys Leu Glu Ile Lys
            100                 105
```

<210> SEQ ID NO 17
<211> LENGTH: 375
<212> TYPE: DNA
<213> ORGANISM: Artificial Sequence
<220> FEATURE:
<223> OTHER INFORMATION: Synthetic polynucleotide

<400> SEQUENCE: 17

```
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaggg atcatcccta tctttggtac agcaaactac   180
gcacagaagt tccagggcag agtcacgatt accgcggaca atccacgag cacagcctac   240
atggagctga gcagcctgag atctgaggac acggccgtgt attactgtgc gagagcctca   300
tattgtagta ctaccagctg cgctagtggt gcttttgata tctggggcca aggcaccctg   360
gtcaccgtct cctca                                                   375
```

<210> SEQ ID NO 18
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 18

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Ser Tyr Cys Ser Thr Thr Ser Cys Ala Ser Gly Ala Phe
                100                 105                 110

Asp Ile Trp Gly Gln Gly Thr Leu Val Thr Val Ser Ser
            115                 120                 125
```

<210> SEQ ID NO 19
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 19

```
gacatccaga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aagctgctca tttactgggc atctgcccgg   180
gaatccgggg tccctgaccg attcagtggc agcgggtctg ggacagattt cactctcacc   240
atcagcagcc tgcagcctga agatgtggca atttattact gtcagcaata ttatagtgtt   300
ccattcactt tcggccctgg gaccaaagtg gagatcaaa                          339
```

```
<210> SEQ ID NO 20
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 20
```

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Val Ala Ile Tyr Tyr Cys Gln Gln
                85                  90                  95

Tyr Tyr Ser Val Pro Phe Thr Phe Gly Pro Gly Thr Lys Val Glu Ile
            100                 105                 110

Lys

```
<210> SEQ ID NO 21
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 21
```

```
gaggtgcagc tggtgcagtc tggagctgag gtgaagaagc ctggggcctc agtgaaggtt    60
tcctgcaagg cttctggata caccttcaat gtatatgcta tcaactgggt gcgacaggcc   120
cctggacaag gcttgagtg gatgggaagg atcatccta tccttggtat agcaaactac   180
gcacagaagt tccagggcag agtcacgatt accgcggaca atccacgag cacagcctac   240 atggagctga gcagcctgag atctgaggac acggccgtgt attactgtgc gagagattac   300
tatggttcgg gagctagggg ctttgactac tggggccagg gcaccctggt caccgtctcc   360
tca                                                                  363
```

```
<210> SEQ ID NO 22
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 22
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Val Tyr
            20                  25                  30

Ala Ile Asn Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Gly Ala Arg Gly Phe Asp Tyr Trp Gly
            100                 105                 110

Gln Gly Thr Leu Val Thr Val Ser Ser
            115                 120
```

```
<210> SEQ ID NO 23
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 23
cagcctgggc tgactcagcc accctcggtg tccaagggct tgagacagac cgccacactc      60
acctgcactg ggaacagcaa caatgttggc aaccaaggag cagcttggct gcagcagcac     120
cagggccacc ctcccaaact cctatcctac gaataacacc cggccctcag gatctca       180 gagagattat ctgcatccag gtcaggaaac acagcctccc tggccattac tggactccag     240
cctgaggacg aggcagacta ttactgtgca tcatgggaca gcagcctcag tgtttgggtg     300
atcggcggag ggaccaagtt gaccgtccta ggt                                  333
```

```
<210> SEQ ID NO 24
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 24

Gln Pro Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Thr Asn Asn Asn Arg Pro Ser Gly Ile Ser Glu Arg Leu Ser
    50                  55                  60

Ala Ser Arg Ser Gly Asn Thr Ala Ser Leu Ala Ile Thr Gly Leu Gln
65                  70                  75                  80

Pro Glu Asp Glu Ala Asp Tyr Tyr Cys Ala Ser Trp Asp Ser Ser Leu
                85                  90                  95

Ser Val Trp Val Ile Gly Gly Gly Thr Lys Leu Thr Val Leu
            100                 105                 110
```

```
<210> SEQ ID NO 25
```

<211> LENGTH: 378
<212> TYPE: DNA
<213> ORGANISM: Artificial Sequence
<220> FEATURE:
<223> OTHER INFORMATION: Synthetic polynucleotide

<400> SEQUENCE: 25

```
gaggtgcagc tggtgcagtc tggggctgag gtgaagaagc ctgggtcctc ggtgaaggtc      60
tcctgcaagg cttctggagg cacctccagc agctatgcta tcagctgggt gcgacaggcc     120
cctggacaag gcttgagtg gatgggaggg atcatccta tctttggtat agcaaactac       180
gcacagaagt tccagggcag agtcacgatt accgcggaca atccacgag acagcctac       240
atggagctga gcagcctgag atctgaggac acggccgtgt attactgtgc gagctctaat    300
tactatggtt cagggagtta ttatccgcga agtgcttttg atatctgggg ccaagggacc    360
acggtcaccg tctcctca                                                  378
```

<210> SEQ ID NO 26
<211> LENGTH: 126
<212> TYPE: PRT
<213> ORGANISM: Artificial Sequence
<220> FEATURE:
<223> OTHER INFORMATION: Synthetic polypeptide

<400> SEQUENCE: 26

```
Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Asn Tyr Tyr Gly Ser Gly Ser Tyr Tyr Pro Arg Ser Ala
            100                 105                 110

Phe Asp Ile Trp Gly Gln Gly Thr Thr Val Thr Val Ser Ser
        115                 120                 125
```

<210> SEQ ID NO 27
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 27

```
gaaacgacac tcacgcagtc tccagccacc ctgtctgtgt ctccagggga aagggccatc     60
ctctcctgca gggccagtca gagtataagc aatgacttag cctggtacca gcagaaacct    120
ggccaggctc ccaggctcct catctatggt gcatccagca gggccactgg catcccagac    180
aggttcagtg gcagtgggtc tgggacggac ttcaccttca ccatcagcag actggagtct    240
gaagattttg cagtgtatta ctgtcagcag tatggtgttt cacctctcac tttcggcggg    300
gggaccaagg tggagatcaa a                                              321
```

```
<210> SEQ ID NO 28
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 28
```

Glu Thr Thr Leu Thr Gln Ser Pro Ala Thr Leu Ser Val Ser Pro Gly
1               5                   10                  15

Glu Arg Ala Ile Leu Ser Cys Arg Ala Ser Gln Ser Ile Ser Asn Asp
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
50                  55                  60

Ser Gly Ser Gly Thr Asp Phe Thr Phe Thr Ile Ser Arg Leu Glu Ser
65                  70                  75                  80

Glu Asp Phe Ala Val Tyr Tyr Cys Gln Gln Tyr Gly Val Ser Pro Leu
                85                  90                  95

Thr Phe Gly Gly Gly Thr Lys Val Glu Ile Lys
            100                 105

```
<210> SEQ ID NO 29
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 29
```

Glu Phe Thr Phe Asn Thr Tyr Gly
1               5

```
<210> SEQ ID NO 30
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 30
```

Ile Ser Tyr Asp Gly Thr Lys Lys
1               5

```
<210> SEQ ID NO 31
<211> LENGTH: 11
<212> TYPE: PRT
<213> ORGANISM: Artificial Sequence
<220> FEATURE:
<223> OTHER INFORMATION: Synthetic oligopeptide

<400> SEQUENCE: 31
```

Ala Arg Ser Gly Asp Ser Asp Ala Phe Asp Ile
1               5                   10

```
<210> SEQ ID NO 32
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 32
```

Gly Gly Thr Phe Gly Ser Tyr Ala
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 33

Ile Asp Ala Ala Asn Gly Asn Thr
1               5

<210> SEQ ID NO 34
<211> LENGTH: 13
<212> TYPE: PRT
<213> ORGANISM: Artificial Sequence
<220> FEATURE:
<223> OTHER INFORMATION: Synthetic oligopeptide

<400> SEQUENCE: 34

Ala Arg Asp Arg Trp Met Thr Thr Arg Ala Phe Asp Ile
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 35

Gly Gly Thr Phe Ser Ser Tyr Ala
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 36

Ile Ile Pro Ile Phe Gly Lys Ala
1               5

<210> SEQ ID NO 37
<211> LENGTH: 16
<212> TYPE: PRT
<213> ORGANISM: Artificial Sequence
<220> FEATURE:
<223> OTHER INFORMATION: Synthetic oligopeptide

<400> SEQUENCE: 37

Ala Arg Asp Gln Gly Ile Ser Ala Asn Phe Lys Asp Ala Phe Asp Ile
1               5                   10                  15

<210> SEQ ID NO 38
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 38

Gly Gly Thr Phe Ser Ser Tyr Ala

<210> SEQ ID NO 39
<211> LENGTH: 18
<212> TYPE: PRT
<213> ORGANISM: Artificial Sequence
<220> FEATURE:
<223> OTHER INFORMATION: Synthetic oligopeptide

<400> SEQUENCE: 39

Ala Arg Val Gly Tyr Cys Ser Ser Thr Ser Cys His Ile Gly Ala Phe
1               5                   10                  15

Asp Ile

<210> SEQ ID NO 40
<211> LENGTH: 18
<212> TYPE: PRT
<213> ORGANISM: Artificial Sequence
<220> FEATURE:
<223> OTHER INFORMATION: Synthetic oligopeptide

<400> SEQUENCE: 40

Ala Arg Ala Ser Tyr Cys Ser Thr Thr Ser Cys Ala Ser Gly Ala Phe
1               5                   10                  15

Asp Ile

<210> SEQ ID NO 41
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 41

Gly Tyr Thr Phe Asn Val Tyr Ala
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 42

Ile Ile Pro Ile Leu Gly Ile Ala
1               5

<210> SEQ ID NO 43
<211> LENGTH: 14
<212> TYPE: PRT
<213> ORGANISM: Artificial Sequence
<220> FEATURE:
<223> OTHER INFORMATION: Synthetic oligopeptide

<400> SEQUENCE: 43

Ala Arg Asp Tyr Tyr Gly Ser Gly Ala Arg Gly Phe Asp Tyr
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic oligopeptide

```
<400> SEQUENCE: 44

Ile Ile Pro Ile Phe Gly Ile Ala
1               5

<210> SEQ ID NO 45
<211> LENGTH: 19
<212> TYPE: PRT
<213> ORGANISM: Artificial Sequence
<220> FEATURE:
<223> OTHER INFORMATION: Synthetic oligopeptide

<400> SEQUENCE: 45

Ala Ser Ser Asn Tyr Tyr Gly Ser Gly Ser Tyr Tyr Pro Arg Ser Ala
1               5                   10                  15

Phe Asp Ile

<210> SEQ ID NO 46
<211> LENGTH: 6
<212> TYPE: PRT
<213> ORGANISM: Artificial Sequence
<220> FEATURE:
<223> OTHER INFORMATION: Synthetic oligopeptide

<400> SEQUENCE: 46

Glu Leu Gly Asp Lys Phe
1               5

<210> SEQ ID NO 47
<211> LENGTH: 3
<212> TYPE: PRT
<213> ORGANISM: Artificial Sequence
<220> FEATURE:
<223> OTHER INFORMATION: Synthetic oligopeptide

<400> SEQUENCE: 47

Gln Asp Ser
1

<210> SEQ ID NO 48
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 48

Gln Ala Trp Asp Ser Asn Ser Tyr Val
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic oligonucleotide

<400> SEQUENCE: 49

Ser Ser Asn Ile Gly Ser Asn Tyr
1               5

<210> SEQ ID NO 50
<211> LENGTH: 3
<212> TYPE: PRT
<213> ORGANISM: Artificial Sequence
<220> FEATURE:
<223> OTHER INFORMATION: Synthetic oligopeptide
```

```
<400> SEQUENCE: 50

Arg Asn Asn
1

<210> SEQ ID NO 51
<211> LENGTH: 11
<212> TYPE: PRT
<213> ORGANISM: Artificial Sequence
<220> FEATURE:
<223> OTHER INFORMATION: Synthetic oligopeptide

<400> SEQUENCE: 51

Ala Ala Trp Asp Asp Ser Leu Arg Gly Pro Val
1               5                   10

<210> SEQ ID NO 52
<211> LENGTH: 6
<212> TYPE: PRT
<213> ORGANISM: Artificial Sequence
<220> FEATURE:
<223> OTHER INFORMATION: Synthetic oligopeptide

<400> SEQUENCE: 52

Glu Ser Val Gly Ser Asn
1               5

<210> SEQ ID NO 53
<211> LENGTH: 3
<212> TYPE: PRT
<213> ORGANISM: Artificial Sequence
<220> FEATURE:
<223> OTHER INFORMATION: Synthetic oligopeptide

<400> SEQUENCE: 53

Gly Ala Ser
1

<210> SEQ ID NO 54
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 54

Gln Gln Tyr Asn Asn Trp Pro Leu Thr
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic oligopeptide

<400> SEQUENCE: 55

Gln Ser Val Ser Ser Ser
1               5

<210> SEQ ID NO 56
<211> LENGTH: 3
<212> TYPE: PRT
<213> ORGANISM: Artificial Sequence
<220> FEATURE:
<223> OTHER INFORMATION: Synthetic oligopeptide
```

```
<400> SEQUENCE: 56

Asp Ser Ser
1

<210> SEQ ID NO 57
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 57

Gln Gln Tyr Ser Ser Ser Pro Tyr Thr
1               5

<210> SEQ ID NO 58
<211> LENGTH: 1255
<212> TYPE: PRT
<213> ORGANISM: Middle East Respiratory Syndrome coronavirus

<400> SEQUENCE: 58

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
            35                  40                  45

Ser Asp Thr Leu Tyr Leu Thr Gln Asp Leu Phe Leu Pro Phe Tyr Ser
        50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285
```

-continued

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
            355                 360                 365

Val Ser Ala Thr Lys Leu Asn Asp Leu Cys Phe Ser Asn Val Tyr Ala
370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
            435                 440                 445

Arg Pro Phe Glu Arg Asp Ile Ser Asn Val Pro Phe Ser Pro Asp Gly
450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
    690                 695                 700

-continued

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
            725                 730                 735

Gln Tyr Gly Ser Phe Cys Thr Gln Leu Asn Arg Ala Leu Ser Gly Ile
        740                 745                 750

Ala Ala Glu Gln Asp Arg Asn Thr Arg Glu Val Phe Ala Gln Val Lys
    755                 760                 765

Gln Met Tyr Lys Thr Pro Thr Leu Lys Tyr Phe Gly Gly Phe Asn Phe
770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp

```
                    1115                1120                1125

Ser Phe Lys Glu Glu Leu Asp Lys Tyr Phe Lys Asn His Thr Ser
            1130                1135                1140

Pro Asp Val Asp Leu Gly Asp Ile Ser Gly Ile Asn Ala Ser Val
            1145                1150                1155

Val Asn Ile Gln Lys Glu Ile Asp Arg Leu Asn Glu Val Ala Lys
            1160                1165                1170

Asn Leu Asn Glu Ser Leu Ile Asp Leu Gln Glu Leu Gly Lys Tyr
            1175                1180                1185

Glu Gln Tyr Ile Lys Trp Pro Trp Tyr Val Trp Leu Gly Phe Ile
            1190                1195                1200

Ala Gly Leu Ile Ala Ile Val Met Val Thr Ile Leu Leu Cys Cys
            1205                1210                1215

Met Thr Ser Cys Cys Ser Cys Leu Lys Gly Ala Cys Ser Cys Gly
            1220                1225                1230

Ser Cys Cys Lys Phe Asp Glu Asp Asp Ser Glu Pro Val Leu Lys
            1235                1240                1245

Gly Val Lys Leu His Tyr Thr
            1250                1255

<210> SEQ ID NO 59
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 59

Ile Ile Pro Ile Phe Gly Thr Ala
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 60

Ser Asn Asn Val Gly Asn Gln Gly
1               5

<210> SEQ ID NO 61
<211> LENGTH: 12
<212> TYPE: PRT
<213> ORGANISM: Artificial Sequence
<220> FEATURE:
<223> OTHER INFORMATION: Synthetic oligopeptide

<400> SEQUENCE: 61

Gln Ser Val Leu Tyr Ser Ser Asn Asn Lys Asn Tyr
1               5                   10

<210> SEQ ID NO 62
<211> LENGTH: 3
<212> TYPE: PRT
<213> ORGANISM: Artificial Sequence
<220> FEATURE:
<223> OTHER INFORMATION: Synthetic oligopeptide

<400> SEQUENCE: 62

Trp Ala Ser
```

```
<210> SEQ ID NO 63
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 63

Gln Gln Tyr Tyr Ser Val Pro Phe Thr
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic oligopeptide

<400> SEQUENCE: 64

Gln Ser Ile Ser Asn Asp
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 65

Gln Gln Tyr Gly Val Ser Pro Leu Thr
1               5

<210> SEQ ID NO 66
<211> LENGTH: 3
<212> TYPE: PRT
<213> ORGANISM: Artificial Sequence
<220> FEATURE:
<223> OTHER INFORMATION: Synthetic oligopeptide

<400> SEQUENCE: 66

Thr Asn Asn
1

<210> SEQ ID NO 67
<211> LENGTH: 11
<212> TYPE: PRT
<213> ORGANISM: Artificial Sequence
<220> FEATURE:
<223> OTHER INFORMATION: Synthetic oligopeptide

<400> SEQUENCE: 67

Ala Ser Trp Asp Ser Ser Leu Ser Val Trp Val
1               5                   10

<210> SEQ ID NO 68
<211> LENGTH: 96
<212> TYPE: PRT
<213> ORGANISM: Homo sapiens

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                20                  25                  30

Ala Ile Ser Trp Val Arg Gln Ala Pro Gly Gln Gly Leu Glu Trp Met
            35                  40                  45

Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

<210> SEQ ID NO 69
<211> LENGTH: 96
<212> TYPE: PRT
<213> ORGANISM: Homo sapiens

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

<210> SEQ ID NO 70
<211> LENGTH: 96
<212> TYPE: PRT
<213> ORGANISM: Homo sapiens

<400> SEQUENCE: 70

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

<210> SEQ ID NO 71
<211> LENGTH: 96
<212> TYPE: PRT
<213> ORGANISM: Homo sapiens

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30
```

```
Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

<210> SEQ ID NO 72
<211> LENGTH: 87
<212> TYPE: PRT
<213> ORGANISM: Homo sapiens

<400> SEQUENCE: 72

Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys
                85

<210> SEQ ID NO 73
<211> LENGTH: 89
<212> TYPE: PRT
<213> ORGANISM: Homo sapiens

<400> SEQUENCE: 73

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys
                85

<210> SEQ ID NO 74
<211> LENGTH: 88
<212> TYPE: PRT
<213> ORGANISM: Homo sapiens

<400> SEQUENCE: 74

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30
```

Leu Ala Trp Tyr Gln Gln Lys Pro Gly Gln Ala Pro Arg Leu Leu Ile
                35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys
                 85

<210> SEQ ID NO 75
<211> LENGTH: 94
<212> TYPE: PRT
<213> ORGANISM: Homo sapiens

<400> SEQUENCE: 75

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys
                 85                  90

<210> SEQ ID NO 76
<211> LENGTH: 89
<212> TYPE: PRT
<213> ORGANISM: Homo sapiens

<400> SEQUENCE: 76

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys
                 85

<210> SEQ ID NO 77
<211> LENGTH: 89
<212> TYPE: PRT
<213> ORGANISM: Homo sapiens

<400> SEQUENCE: 77

Gln Ala Gly Leu Thr Gln Pro Pro Ser Val Ser Lys Gly Leu Arg Gln
 1               5                  10                  15

Thr Ala Thr Leu Thr Cys Thr Gly Asn Ser Asn Asn Val Gly Asn Gln
                20                  25                  30

Gly Ala Ala Trp Leu Gln Gln His Gln Gly His Pro Pro Lys Leu Leu

```
            35                  40                  45
Ser Tyr Arg Asn Asn Arg Pro Ser Gly Ile Ser Glu Arg Leu Ser
        50                  55                  60
Ala Ser Arg Ser Gly Asn Thr Ala Ser Leu Thr Ile Thr Gly Leu Gln
65                  70                  75                  80
Pro Glu Asp Glu Ala Asp Tyr Tyr Cys
                85
```

<210> SEQ ID NO 78
<211> LENGTH: 12
<212> TYPE: PRT
<213> ORGANISM: Middle East Respiratory Syndrome coronavirus

<400> SEQUENCE: 78

```
Ala Ala Ala Leu Asp Thr Val Tyr Arg Pro Asn Ile
1               5                   10
```

<210> SEQ ID NO 79
<211> LENGTH: 12
<212> TYPE: PRT
<213> ORGANISM: Middle East Respiratory Syndrome coronavirus

<400> SEQUENCE: 79

```
Pro Ala Val Leu Asp Thr Val Tyr Arg Pro Asn Ile
1               5                   10
```

<210> SEQ ID NO 80
<211> LENGTH: 12
<212> TYPE: PRT
<213> ORGANISM: Middle East Respiratory Syndrome coronavirus

<400> SEQUENCE: 80

```
Ala Ser Ala Leu Asp Thr Val Tyr Arg Pro Asn Ile
1               5                   10
```

<210> SEQ ID NO 81
<211> LENGTH: 12
<212> TYPE: PRT
<213> ORGANISM: Middle East Respiratory Syndrome coronavirus

<400> SEQUENCE: 81

```
Ala Val Ala Leu Asp Thr Val Tyr Arg Pro Asn Ile
1               5                   10
```

<210> SEQ ID NO 82
<211> LENGTH: 12
<212> TYPE: PRT
<213> ORGANISM: Middle East Respiratory Syndrome coronavirus

<400> SEQUENCE: 82

```
Ala Ala Ala Phe Asp Thr Val Tyr Arg Pro Asn Ile
1               5                   10
```

<210> SEQ ID NO 83
<211> LENGTH: 12
<212> TYPE: PRT
<213> ORGANISM: Middle East Respiratory Syndrome coronavirus

<400> SEQUENCE: 83

```
Ala Ala Ala Leu Gly Thr Val Tyr Arg Pro Asn Ile
1               5                   10
```

<210> SEQ ID NO 84

```
<211> LENGTH: 12
<212> TYPE: PRT
<213> ORGANISM: Middle East Respiratory Syndrome coronavirus

<400> SEQUENCE: 84

Ala Ala Ala Leu Asp Thr Ala Tyr Arg Pro Asn Ile
1               5                   10

<210> SEQ ID NO 85
<211> LENGTH: 12
<212> TYPE: PRT
<213> ORGANISM: Middle East Respiratory Syndrome coronavirus

<400> SEQUENCE: 85

Ala Ala Ala Leu Asp Thr Val Tyr Arg Pro Ile Ile
1               5                   10

<210> SEQ ID NO 86
<211> LENGTH: 12
<212> TYPE: PRT
<213> ORGANISM: Middle East Respiratory Syndrome coronavirus

<400> SEQUENCE: 86

Ala Ala Ala Leu Asp Thr Val Tyr Arg Ser Asn Ile
1               5                   10

<210> SEQ ID NO 87
<211> LENGTH: 12
<212> TYPE: PRT
<213> ORGANISM: Middle East Respiratory Syndrome coronavirus

<400> SEQUENCE: 87

Ala Ala Ala Leu Asp Thr Val Tyr Gly Pro Asn Ile
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic Oligopeptide

<400> SEQUENCE: 88

Ala Ala Ala Leu Asp Thr Val Tyr Ser Pro Asn Thr
1               5                   10

<210> SEQ ID NO 89
<211> LENGTH: 12
<212> TYPE: PRT
<213> ORGANISM: Middle East Respiratory Syndrome coronavirus

<400> SEQUENCE: 89

Ala Ala Ala Leu Asp Thr Val Tyr Thr Pro Asn Ile
1               5                   10

<210> SEQ ID NO 90
<211> LENGTH: 12
<212> TYPE: PRT
<213> ORGANISM: Middle East Respiratory Syndrome coronavirus

<400> SEQUENCE: 90

Ala Ala Ala Leu Asp Thr Val Tyr Lys Pro Asn Ile
1               5                   10

<210> SEQ ID NO 91
```

```
<211> LENGTH: 12
<212> TYPE: PRT
<213> ORGANISM: Middle East Respiratory Syndrome coronavirus

<400> SEQUENCE: 91

Ala Ala Ala Phe Asp Ala Val Tyr Arg Pro Asn Ile
1               5                   10

<210> SEQ ID NO 92
<211> LENGTH: 12
<212> TYPE: PRT
<213> ORGANISM: Middle East Respiratory Syndrome coronavirus

<400> SEQUENCE: 92

Ala Ala Ala Leu Asp Thr Val Tyr Lys Pro Asn Ile
1               5                   10

<210> SEQ ID NO 93
<211> LENGTH: 12
<212> TYPE: PRT
<213> ORGANISM: Middle East Respiratory Syndrome coronavirus

<400> SEQUENCE: 93

Ala Ala Ala Phe Asp Thr Val Cys Arg Pro Asn Ile
1               5                   10

<210> SEQ ID NO 94
<211> LENGTH: 12
<212> TYPE: PRT
<213> ORGANISM: Middle East Respiratory Syndrome coronavirus

<400> SEQUENCE: 94

Ala Ala Ala Leu Asp Thr Val His Arg Pro Asn Ile
1               5                   10
```

UNITED STATES PATENT AND TRADEMARK OFFICE
CERTIFICATE OF CORRECTION

PATENT NO. : 10,131,704 B2
APPLICATION NO. : 15/306617
DATED : November 20, 2018
INVENTOR(S) : Wayne A. Marasco et al.

It is certified that error appears in the above-identified patent and that said Letters Patent is hereby corrected as shown below:

In the Specification

At Column 1, Line numbers 15-19, change:
"This invention was made with government support under R01AI085525 awarded by the National Institutes of Health and WOIINF-10-0226 awarded by Defense Advanced Research Projects Agency. The United States government has certain rights in the invention."

To:
--This invention was made with government support under grant numbers AI085524 awarded by The National Institutes of Health and W911NF-10-1-0266 awarded by The Defense Advanced Research Projects Agency. The government has certain rights in the invention.--

Signed and Sealed this
Twenty-fourth Day of September, 2019

Andrei Iancu
*Director of the United States Patent and Trademark Office*